US011708415B2

(12) United States Patent
Bruse et al.

(10) Patent No.: US 11,708,415 B2
(45) Date of Patent: Jul. 25, 2023

(54) TREATMENT AND INHIBITION OF INFLAMMATORY LUNG DISEASES IN PATIENTS HAVING RISK ALLELES IN THE GENES ENCODING IL33 AND IL1RL1

(71) Applicant: Regeneron Pharmaceuticals, Inc., Tarrytown, NY (US)

(72) Inventors: Shannon Bruse, Tarrytown, NY (US); Shane McCarthy, Tarrytown, NY (US); Aris Baras, Tarrytown, NY (US); Frederick Dewey, Tarrytown, NY (US); Omri Gottesman, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 3 days.

(21) Appl. No.: 16/599,709

(22) Filed: Oct. 11, 2019

(65) Prior Publication Data

US 2020/0031922 A1 Jan. 30, 2020

Related U.S. Application Data

(63) Continuation of application No. PCT/US2018/023266, filed on Mar. 20, 2018.

(60) Provisional application No. 62/485,077, filed on Apr. 13, 2017.

(51) Int. Cl.

| | |
|---|---|
| ***A61K 39/00*** | (2006.01) |
| ***C07K 16/28*** | (2006.01) |
| ***A61P 11/06*** | (2006.01) |
| ***A61P 11/00*** | (2006.01) |
| ***C12Q 1/6883*** | (2018.01) |
| *C07K 16/24* | (2006.01) |

(52) U.S. Cl.

CPC .......... *C07K 16/2866* (2013.01); *A61P 11/00* (2018.01); *A61P 11/06* (2018.01); *C12Q 1/6883* (2013.01); *A61K 2039/507* (2013.01); *C07K 16/244* (2013.01); *C07K 2317/76* (2013.01); *C12Q 2600/106* (2013.01); *C12Q 2600/112* (2013.01); *C12Q 2600/156* (2013.01)

(58) Field of Classification Search

CPC .................... A61K 39/395; A61K 2039/55527

See application file for complete search history.

(56) References Cited

U.S. PATENT DOCUMENTS

| | | | |
|---|---|---|---|
| 7,186,809 B2 | 3/2007 | Pluenneke | |
| 7,452,980 B2 | 11/2008 | Kingsbury et al. | |
| 7,605,237 B2 | 10/2009 | Stevens et al. | |
| 7,608,693 B2 | 10/2009 | Martin et al. | |
| 7,638,606 B2 | 12/2009 | Carter et al. | |
| 8,092,804 B2 | 1/2012 | Eriksson et al. | |
| 8,187,596 B1 | 5/2012 | Chackerian et al. | |
| 8,444,987 B2 | 5/2013 | Kingsbury et al. | |
| 8,679,487 B2 | 3/2014 | Armitage et al. | |
| 8,877,189 B2 | 11/2014 | Eriksson et al. | |
| 9,290,574 B2 | 3/2016 | Kostic et al. | |
| 9,453,072 B2 | 9/2016 | Murphy et al. | |
| 2010/0160802 A1* | 6/2010 | Gudbjartsson | A61B 5/026 536/24.31 |
| 2013/0253847 A1 | 9/2013 | Gudbjartsson et al. | |
| 2014/0271642 A1 | 9/2014 | Murphy et al. | |
| 2014/0271658 A1* | 9/2014 | Murphy | A61P 11/02 424/142.1 |
| 2015/0320021 A1 | 11/2015 | Wang et al. | |
| 2015/0320022 A1 | 11/2015 | Wang et al. | |
| 2016/0168242 A1 | 6/2016 | Hass et al. | |
| 2016/0168640 A1 | 6/2016 | Khosla et al. | |
| 2017/0096483 A1 | 4/2017 | Orengo et al. | |
| 2018/0155436 A1 | 6/2018 | Orengo et al. | |

FOREIGN PATENT DOCUMENTS

| | | |
|---|---|---|
| EP | 1725261 | 11/2006 |
| EP | 2928916 | 10/2015 |
| WO | 2011031600 | 3/2011 |
| WO | 2012113813 | 8/2012 |
| WO | 2013165894 | 11/2013 |
| WO | 2013173761 | 11/2013 |
| WO | 2014031610 | 2/2014 |
| WO | 2014152195 | 9/2014 |
| WO | 2015099175 | 7/2015 |
| WO | 2015106080 | 7/2015 |
| WO | 2015127229 | 8/2015 |
| WO | 2016077366 | 5/2016 |
| WO | 2016077381 | 5/2016 |
| WO | 2016156440 | 10/2016 |

OTHER PUBLICATIONS

Moffatt et al. (2010), NEJM, vol. 363, pp. 1211-1221. (Year: 2010).*

Corren et al., "A randomized, controlled, phase 2 study of AMG 317, an IL-4Ralpha antagonist, in patients with asthma", Am J Respir Crit Care Med, 2010, 181(8), pp. 788-796.

Grotenboer et al., "Decoding asthma: Translating genetic variation in IL33 and IL1RL1 into disease pathophysiology", Journal of Allergy and Clinical Immunology, 2013, 131(3), pp. 856-865.

Meyers et al., "The Genetics of Asthma: Towards a Personalised Approach to Diagnosis and Treatment", The Lancet, 2014, 2(5), pp. 405-415.

Ramasamy et al., "Genome-Wide Association Studies of Asthma in Population-Based Cohorts Confirm Known and Suggested Loci and Identify an Additional Association near HLA", Plos One, 2012, 7(9), pp. e44008.

Tulah et al., "Defining the contribution of SNPs identified in asthma GWAS to clinical variables in asthmatic children", BMC Medical Genetics, Biomed Central, 2013, 14(1), pp. 100.

(Continued)

*Primary Examiner* — Prema M Mertz

(74) *Attorney, Agent, or Firm* — Armstrong Teasdale LLP

(57) ABSTRACT

IL33 antagonists alone or in combination with IL-4R antagonists can be used to treat or inhibit eosinophilic asthma, eosinophilic COPD, eosinophilic ACOS, and nasal polyps in a subject having one or more risk alleles in the intronic IL1RL1 variant rs1420101, in the IL33 variant rs1342326, in both, or in variants in linkage disequilibrium thereof.

18 Claims, 24 Drawing Sheets

Specification includes a Sequence Listing.

(56) References Cited

OTHER PUBLICATIONS

International Search Report and Written Opinion for PCT Application PCT/2018/023266.
Chung et al., "Targeting the interleukin pathway in the treatment of asthma", Lancet, 2015, 386, pp. 1086-1094.
Tomkinson et al., "A Murine IL-4 Receptor Antagonist That Inhibits IL-4-and IL-13-Induced Responses Prevents Antigen-Induced Airway Eosinophilia and Airway Hyperresponsiveness", J Immunol, 2001, 166, pp. 5792-5800.
Kim et al., "Factors associated with plasma IL-33 levels in patients with chronic obstructive pulmonary disease", International Journal of COPD, 2017, 12, pp. 395-402.

* cited by examiner

A

A) Asthma

| Gene | SNP | Group | NumCases (AAF) | NumCtrls (AAF) | OR (95% CI) | P-value |
|---|---|---|---|---|---|---|
| IL33 | rs1342326 | GSA | 3911 (0.16) | 20814 (0.16) | 1.11 (1.04-1.19) | 1.1e-03 |
| | | OMNI | 8913 (0.17) | 37193 (0.16) | 1.08 (1.03-1.12) | 1.2e-03 |
| | | Meta | 12824 (0.18) | 58007 (0.16) | 1.09 (1.05-1.13) | 6.0e-06 |
| IL1RL1 | rs1420101 | GSA | 3911 (0.38) | 20815 (0.37) | 1.07 (1.02-1.13) | 5.6e-03 |
| | | OMNI | 8909 (0.38) | 37207 (0.36) | 1.07 (1.04-1.11) | 4.3e-05 |
| | | Meta | 12820 (0.38) | 58022 (0.37) | 1.07 (1.04-1.1) | 8.2e-07 |
| IL33 | rs146597587 | xGEN | 3974 (0.002) | 21150 (0.0033) | 0.59 (0.35-1) | 4.9e-02 |
| | | VCRome | 9292 (0.0027) | 38804 (0.003) | 0.92 (0.68-1.25) | 6.0e-01 |
| | | Meta | 13266 (0.0025) | 59954 (0.0031) | 0.82 (0.63-1.07) | 1.5e-01 |

B) High Eosinophil Asthma

| Gene | SNP | Group | NumCases (AAF) | NumCtrls (AAF) | OR (95% CI) | P-value |
|---|---|---|---|---|---|---|
| IL33 | rs1342326 | GSA | 1417 (0.18) | 20814 (0.16) | 1.12 (1.01-1.23) | 3.2e-02 |
| | | OMNI | 3503 (0.18) | 37193 (0.16) | 1.12 (1.05-1.19) | 6.5e-04 |
| | | Meta | 4920 (0.18) | 58007 (0.16) | 1.12 (1.06-1.18) | 5.6e-05 |
| IL1RL1 | rs1420101 | GSA | 1416 (0.41) | 20815 (0.37) | 1.17 (1.08-1.27) | 6.4e-05 |
| | | OMNI | 3497 (0.4) | 37207 (0.36) | 1.15 (1.1-1.21) | 3.3e-08 |
| | | Meta | 4913 (0.4) | 58022 (0.37) | 1.16 (1.11-1.21) | 9.6e-12 |
| IL33 | rs146597587 | xGEN | 1458 (0.0031) | 21150 (0.0033) | 0.89 (0.45-1.76) | 7.4e-01 |
| | | VCRome | 3619 (0.0017) | 36804 (0.003) | 0.55 (0.31-0.99) | 4.8e-02 |
| | | Meta | 5077 (0.0021) | 59954 (0.0031) | 0.68 (0.44-1.06) | 8.6e-02 |

C) Low Eosinophil Asthma

| Gene | SNP | Group | NumCases (AAF) | NumCtrls (AAF) | OR (95% CI) | P-value |
|---|---|---|---|---|---|---|
| | | GSA | 1767 (0.18) | 20814 (0.16) | 1.08 (0.98-1.18) | 1.1e-01 |
| IL33 | rs1342326 | OMNI | 4430 (0.16) | 37193 (0.16) | 1.01 (0.96-1.08) | 6.3e-01 |
| | | Meta | 6197 (0.17) | 58007 (0.16) | 1.03 (0.98-1.09) | 2.0e-01 |
| | | GSA | 1767 (0.37) | 20815 (0.37) | 1.02 (0.95-1.1) | 5.1e-01 |
| IL1RL1 | rs1420101 | OMNI | 4433 (0.37) | 37207 (0.36) | 1.01 (0.97-1.06) | 6.0e-01 |
| | | Meta | 6200 (0.37) | 58022 (0.37) | 1.02 (0.98-1.06) | 4.2e-01 |
| | | xGEN | 1774 (0.0011) | 21150 (0.0033) | 0.33 (0.12-0.9) | 3.0e-02 |
| IL33 | rs146597587 | VCRome | 4624 (0.0037) | 38804 (0.003) | 1.23 (0.86-1.78) | 2.6e-01 |
| | | Meta | 6398 (0.003) | 59954 (0.0031) | 1.06 (0.75-1.49) | 7.5e-01 |

A) COPD

| Gene | SNP | Group | NumCases (AAF) | NumCtrls (AAF) | OR (95% CI) | P-value |
|---|---|---|---|---|---|---|
| | | GSA | 2214 (0.16) | 20814 (0.16) | 1.02 (0.93-1.11) | 7.0e-01 |
| IL33 | rs1342326 | OMNI | 7313 (0.17) | 37193 (0.16) | 1.05 (0.99-1.1) | 8.2e-02 |
| | | Meta | 9527 (0.17) | 58007 (0.16) | 1.04 (0.99-1.09) | 8.9e-02 |
| | | GSA | 2214 (0.38) | 20615 (0.37) | 1.03 (0.96-1.1) | 4.2e-01 |
| IL1RL1 | rs1420101 | OMNI | 7302 (0.37) | 37207 (0.36) | 1.04 (1-1.08) | 5.5e-02 |
| | | Meta | 9516 (0.37) | 58022 (0.37) | 1.04 (1-1.07) | 3.9e-02 |
| | | xGEN | 2227 (0.0036) | 21150 (0.0033) | 0.89 (0.51-1.56) | 6.8e-01 |
| IL33 | rs146597587 | VCRome | 7552 (0.0032) | 38804 (0.003) | 1.03 (0.73-1.45) | 8.7e-01 |
| | | Meta | 9779 (0.0033) | 59954 (0.0031) | 0.99 (0.74-1.33) | 9.4e-01 |

B) High Eosinophil COPD

| Gene | SNP | Group | NumCases (AAF) | NumCtrls (AAF) | OR (95% CI) | P-value |
|---|---|---|---|---|---|---|
| IL33 | rs1342326 | GSA | 903 (0.17) | 20814 (0.16) | 1.06 (0.93-1.21) | 3.8e-01 |
| | | OMNI | 3167 (0.18) | 37193 (0.16) | 1.12 (1.05-1.21) | 1.5e-03 |
| | | Meta | 4070 (0.17) | 58007 (0.16) | 1.11 (1.04-1.18) | 1.3e-03 |
| IL1RL1 | rs1420101 | GSA | 903 (0.39) | 20815 (0.37) | 1.1 (0.99-1.22) | 7.3e-02 |
| | | OMNI | 3163 (0.39) | 37207 (0.36) | 1.13 (1.07-1.19) | 2.3e-05 |
| | | Meta | 4066 (0.39) | 58022 (0.37) | 1.12 (1.07-1.18) | 4.6e-06 |
| IL33 | rs146597587 | xGEN | 911 (0.0055) | 21150 (0.0033) | 1.36 (0.69-2.7) | 3.8e-01 |
| | | VCRome | 3265 (0.002) | 38804 (0.003) | 0.59 (0.33-1.06) | 7.9e-02 |
| | | Meta | 4176 (0.0028) | 59954 (0.0031) | 0.84 (0.54-1.31) | 4.5e-01 |

C) Low Eosinophil COPD

| Gene | SNP | Group | NumCases (AAF) | NumCtrls (AAF) | OR (95% CI) | P-value |
|---|---|---|---|---|---|---|
| | | GSA | 1015 (0.16) | 20814 (0.16) | 0.96 (0.85-1.1) | 5.6e-01 |
| IL33 | rs1342326 | OMNI | 3361 (0.16) | 37193 (0.16) | 0.99 (0.92-1.06) | 7.5e-01 |
| | | Meta | 4376 (0.16) | 58007 (0.16) | 0.98 (0.92-1.05) | 5.8e-01 |
| | | GSA | 1015 (0.37) | 20815 (0.37) | 0.98 (0.89-1.08) | 6.4e-01 |
| IL1RL1 | rs1420101 | OMNI | 3356 (0.35) | 37207 (0.36) | 0.96 (0.91-1.02) | 1.6e-01 |
| | | Meta | 4371 (0.36) | 58022 (0.37) | 0.97 (0.92-1.01) | 1.5e-01 |
| | | xGEN | 1012 (0.0025) | 21150 (0.0033) | 0.63 (0.25-1.59) | 3.3e-01 |
| IL33 | rs146597587 | VCRome | 3475 (0.0045) | 36804 (0.003) | 1.44 (0.96-2.16) | 8.2e-02 |
| | | Meta | 4487 (0.004) | 59954 (0.0031) | 1.26 (0.87-1.82) | 2.3e-01 |

B) High Eosinophil ACOS

| Gene | SNP | Group | NumCases (AAF) | NumCtrls (AAF) | OR (95% CI) | P-value |
|---|---|---|---|---|---|---|
| | | GSA | 300 (0.18) | 20814 (0.16) | 1.11 (0.89-1.37) | 3.5e-01 |
| IL33 | rs1342326 | OMNI | 1073 (0.18) | 37193 (0.16) | 1.12 (1-1.25) | 6.0e-02 |
| | | Meta | 1373 (0.18) | 58007 (0.16) | 1.11 (1.01-1.23) | 3.6e-02 |
| | | GSA | 300 (0.41) | 20815 (0.37) | 1.17 (0.99-1.38) | 6.7e-02 |
| IL1RL1 | rs1420101 | OMNI | 1072 (0.4) | 37207 (0.36) | 1.17 (1.07-1.28) | 7.5e-04 |
| | | Meta | 1372 (0.4) | 58022 (0.37) | 1.17 (1.08-1.26) | 1.2e-04 |
| | | xGEN | 303 (0.0033) | 21150 (0.0033) | 0.84 (0.2-3.46) | 8.1e-01 |
| IL33 | rs146597587 | VCRome | 1107 (0.0018) | 38804 (0.003) | 0.56 (0.21-1.58) | 2.9e-01 |
| | | Meta | 1410 (0.0021) | 59954 (0.0031) | 0.66 (0.29-1.49) | 3.1e-01 |

C) Low Eosinophil ACOS

| Gene | SNP | Group | NumCases (AAF) | NumCtrls (AAF) | OR (95% CI) | P-value |
|---|---|---|---|---|---|---|
| | | GSA | 293 (0.18) | 20814 (0.16) | 1.12 (0.9-1.39) | 3.0e-01 |
| IL33 | rs1342326 | OMNI | 1022 (0.17) | 37193 (0.16) | 1.03 (0.91-1.16) | 6.2e-01 |
| | | Meta | 1315 (0.17) | 58007 (0.16) | 1.05 (0.95-1.17) | 3.4e-01 |
| | | GSA | 293 (0.34) | 20815 (0.37) | 0.88 (0.74-1.05) | 1.7e-01 |
| IL1RL1 | rs1420101 | OMNI | 1021 (0.35) | 37207 (0.36) | 0.97 (0.88-1.06) | 4.8e-01 |
| | | Meta | 1314 (0.35) | 58022 (0.37) | 0.95 (0.87-1.03) | 1.9e-01 |
| | | xGEN | 296 (0) | 21150 (0.0033) | 0 (0-1.64082072573846e+259) | 9.7e-01 |
| IL33 | rs146597587 | VCRome | 1060 (0.0047) | 38804 (0.003) | 1.57 (0.82-3) | 1.8e-01 |
| | | Meta | 1356 (0.0037) | 59954 (0.0031) | NA (0.82-3) | 2.2e-01 |

A) Asthma

| Group | Sum | NumCases (AAF) | NumCtrls (AAF) | OR (95% CI) | P-value |
|---|---|---|---|---|---|
| | 0 | 3325 | 16442 | | |
| | 1 | 5547 (0.63) | 25108 (0.6) | 1.09 (1.04-1.15) | 3.51e-04 |
| Meta | 2 | 3157 (0.49) | 13409 (0.45) | 1.17 (1.1-1.23) | 3.10e-08 |
| | 3 | 732 (0.18) | 2806 (0.15) | 1.28 (1.17-1.41) | 6.99e-08 |
| | 4 | 52 (0.02) | 219 (0.01) | 1.18 (0.87-1.61) | 2.89e-01 |
| | Trend | 12813 | 57984 | | 3.27e-12 |

B) COPD

C) ACOS

A) Asthma
High
| Group | Sum | NumCases (AAF) | NumCtrls (AAF) | OR (95% CI) | P-value |
|---|---|---|---|---|---|
| | 0 | 1192 | 18442 | | |
| | 1 | 2131 (0.64) | 25106 (0.6) | 1.17 (1.08-1.26) | 4.18e-05 |
| Meta | 2 | 1238 (0.51) | 13409 (0.45) | 1.28 (1.17-1.39) | 9.75e-09 |
| | 3 | 329 (0.22) | 2606 (0.15) | 1.61 (1.42-1.84) | 6.33e-13 |
| | 4 | 22 (0.02) | 219 (0.01) | 1.39 (0.89-2.17) | 1.51e-01 |
| | Trend | 4912 | 57964 | | 1.37e-15 |
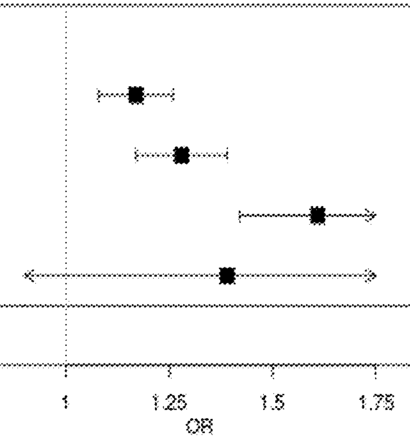
Low
| Group | Sum | NumCases (AAF) | NumCtrls (AAF) | OR (95% CI) | P-value |
|---|---|---|---|---|---|
| | 0 | 1683 | 18442 | | |
| | 1 | 2713 (0.62) | 25106 (0.6) | 1.05 (0.99-1.12) | 1.16e-01 |
| Meta | 2 | 1477 (0.47) | 13409 (0.45) | 1.08 (1-1.16) | 4.91e-02 |
| | 3 | 299 (0.15) | 2606 (0.15) | 1.04 (0.91-1.19) | 5.88e-01 |
| | 4 | 23 (0.01) | 219 (0.01) | 1.03 (0.66-1.59) | 9.09e-01 |
| | Trend | 6195 | 57964 | | 7.94e-02 |
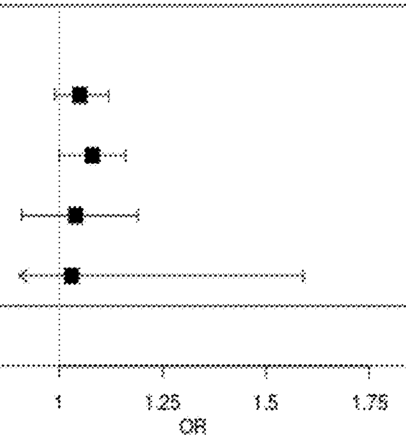
Figure 7

B) COPD

C) ACOS

High

| Group | Sum | NumCases (AAF) | NumCtrls (AAF) | OR (95% CI) | P-value |
|---|---|---|---|---|---|
| | 0 | 342 | 16442 | | |
| | 1 | 585 (0.63) | 25108 (0.6) | 1.11 (0.97-1.27) | 1.37e-01 |
| Meta | 2 | 341 (0.5) | 13409 (0.45) | 1.22 (1.05-1.43) | 9.83e-03 |
| | 3 | 97 (0.22) | 2806 (0.15) | 1.7 (1.34-2.14) | 1.09e-05 |
| | 4 | 6 (0.02) | 219 (0.01) | 1.38 (0.6-3.2) | 4.45e-01 |
| | Trend | 1371 | 57984 | | 1.80e-05 |

Low

| Group | Sum | NumCases (AAF) | NumCtrls (AAF) | OR (95% CI) | P-value |
|---|---|---|---|---|---|
| | 0 | 368 | 16442 | | |
| | 1 | 582 (0.51) | 25108 (0.6) | 1.03 (0.9-1.17) | 7.12e-01 |
| Meta | 2 | 312 (0.46) | 13408 (0.45) | 1.04 (0.89-1.22) | 5.67e-01 |
| | 3 | 45 (0.11) | 2806 (0.15) | 0.78 (0.55-1.03) | 8.13e-02 |
| | 4 | 7 (0.02) | 219 (0.01) | 1.62 (0.74-3.51) | 2.26e-01 |
| | Trend | 1314 | 57984 | | 8.38e-01 |

A

| VCRome | Asthma | COPD | ACOS | Controls |
|---|---|---|---|---|
| Number of CasesCases | 9293 | 7556 | 2336 | 38810 |
| Median Age Yrs (IQR) | 57.6 (43-69.1) | 70 (61-78.7) | 67.3 (57.9-76.625) | 60.7 (47-72) |
| Number of Females (%) | 6835 (0.74) | 3632 (0.48) | 1458 (0.62) | 22662 (0.58) |
| BMI kg/m2, (IQR) | 32.27 (27.12-38.2575) | 29.99 (25.62-35.18) | 31.92 (27.1-37.53) | 30.1 (26.055-35.24) |
| Height, in (IQR) | 65 (62.5-67.5) | 66 (63-69) | 65 (62-68) | 66 (63-69) |
| Current Smoker | 1583 (0.17) | 2171 (0.29) | 570 (0.24) | 5177 (0.13) |
| Former Smoker | 3655 (0.39) | 4541 (0.6) | 1308 (0.56) | 14201 (0.37) |
| Number with Eosinophil Counts | 8244 (0.89) | 6743 (0.89) | 2168 (0.93) | 30467 (0.79) |
| Median Eos Count (IQR) | 0.18 (0.115-0.26) | 0.19 (0.125-0.27) | 0.2 (0.13-0.28) | 0.15 (0.1-0.22) |

B

| xGEN | Asthma | COPD | ACOS | Controls |
|---|---|---|---|---|
| Number of CasesCases | 3974 | 2227 | 657 | 21151 |
| Median Age Yrs (IQR) | 49.1 (34.2-62.3) | 64.8 (56.65-73.35) | 61.7 (52.8-71.6) | 53.5 (38.5-65.3) |
| Number of Females (%) | 2968 (0.75) | 1237 (0.56) | 449 (0.68) | 12886 (0.61) |
| BMI kg/m2, (IQR) | 31.07 (26.09-36.81) | 29.27 (25.2-34.8425) | 31.235 (26.57-37.14) | 29.3 (25.33-34.28) |
| Height, in (IQR) | 65 (63-67.99) | 66 (63-69) | 65 (62.48-68) | 66 (63-69) |
| Current Smoker | 843 (0.21) | 798 (0.36) | 211 (0.32) | 3658 (0.17) |
| Former Smoker | 1309 (0.33) | 1186 (0.53) | 325 (0.49) | 6619 (0.31) |
| Number with Eosinophil Counts | 3232 (0.81) | 1923 (0.86) | 599 (0.91) | 14571 (0.69) |
| Median Eos Count (IQR) | 0.18 (0.115-0.265) | 0.19 (0.12-0.27) | 0.2 (0.125-0.28) | 0.15 (0.1-0.22) |

| OMNI | Asthma | COPD | ACOS | Controls |
|---|---|---|---|---|
| Number of CasesCases | 8922 | 7322 | 2258 | 37244 |
| Median Age Yrs (IQR) | 57.8 (43.3-69.3) | 70.1 (61.1-78.9) | 67.45 (58.025-76.8) | 60.9 (47.2-72.2) |
| Number of Females (%) | 6552 (0.73) | 3503 (0.48) | 1406 (0.62) | 21677 (0.58) |
| BMI kg/m2, (IQR) | 32.285 (27.12-38.26) | 29.99 (25.62625-35.15) | 31.93 (26.985-37.49) | 30.1 (26.07-35.22) |
| Height, in (IQR) | 65 (62.5-67.5) | 66 (63-69) | 65 (62-68) | 66 (63-69) |
| Current Smoker | 1516 (0.17) | 2093 (0.29) | 549 (0.24) | 4939 (0.13) |
| Former Smoker | 3522 (0.39) | 4412 (0.6) | 1269 (0.56) | 13658 (0.37) |
| Number with Eosinophil Counts | 7941 (0.89) | 6536 (0.89) | 2097 (0.93) | 29299 (0.79) |
| Median Eos Count (IQR) | 0.18 (0.115-0.26) | 0.19 (0.125-0.27) | 0.2 (0.13-0.28) | 0.15 (0.1-0.22) |

D

| GSA | Asthma | COPD | ACOS | Controls |
|---|---|---|---|---|
| Number of CasesCases | 3912 | 2214 | 651 | 20816 |
| Median Age Yrs (IQR) | 49.6 (34.1-62.5) | 64.8 (56.7-73.4) | 61.7 (52.9-71.9) | 53.6 (38.6-65.4) |
| Number of Females (%) | 2915 (0.75) | 1218 (0.55) | 445 (0.68) | 12664 (0.61) |
| BMI kg/m2, (IQR) | 31.08 (26.14-36.8075) | 29.26 (25.18-34.84) | 31.17 (26.57-37.13) | 29.34 (25.36-34.28) |
| Height, in (IQR) | 65 (63-68) | 66 (63-69) | 65 (62.44-68) | 66 (63-69) |
| Current Smoker | 820 (0.21) | 782 (0.35) | 209 (0.32) | 3571 (0.17) |
| Former Smoker | 1291 (0.33) | 1190 (0.54) | 324 (0.5) | 6518 (0.31) |
| Number with Eosinophil Counts | 3184 (0.81) | 1918 (0.87) | 593 (0.91) | 14430 (0.69) |
| Median Eos Count (IQR) | 0.18 (0.115-0.265) | 0.19 (0.12-0.27) | 0.2 (0.125-0.28) | 0.15 (0.1-0.22) |

Figure 8 (cont.)

A) Allergic Rhinitis

B) Nasal Polyps
| Gene | SNP | Group | NumCases (AAF) | NumCtrls (AAF) | OR (95% CI) | P-value |
|---|---|---|---|---|---|---|
| | | GSA | 183 (0.23) | 22878 (0.17) | 1.59 (1.2-2.01) | 9.0e-04 |
| IL33 | rs1342326 | OMNI | 360 (0.22) | 43939 (0.16) | 1.45 (1.22-1.73) | 3.5e-05 |
| | | Meta | 523 (0.22) | 66517 (0.16) | 1.48 (1.28-1.72) | 1.2e-07 |
| | | GSA | 163 (0.43) | 22880 (0.37) | 1.29 (1.03-1.61) | 2.5e-02 |
| IL1RL1 | rs1420101 | OMNI | 360 (0.39) | 43941 (0.37) | 1.12 (0.97-1.31) | 1.3e-01 |
| | | Meta | 523 (0.4) | 66821 (0.37) | 1.17 (1.04-1.33) | 1.2e-02 |
| | | xGEN | 164 (0.0061) | 23272 (0.0032) | 1.51 (0.44-7.4) | 4.1e-01 |
| IL33 | rs146597587 | VCRome | 371 (0.0027) | 45779 (0.0029) | 0.95 (0.23-3.82) | 9.4e-01 |
| | | Meta | 535 (0.0037) | 69051 (0.003) | 1.3 (0.48-3.52) | 6.0e-01 |
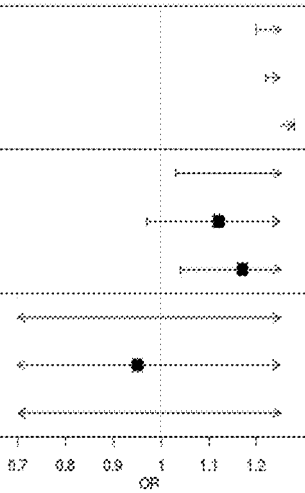
| Group | Sum | NumCases (AAF) | NumCtrls (AAF) | OR (95% CI) | P-value |
|---|---|---|---|---|---|
| | 0 | 116 | 18722 | | |
| | 1 | 206 (0.63) | 29007 (0.61) | 1.12 (0.89-1.4) | 3.37e-01 |
| Meta | 2 | 150 (0.56) | 15496 (0.45) | 1.54 (1.21-1.97) | 4.99e-04 |
| | 3 | 45 (0.25) | 3317 (0.15) | 2.24 (1.58-3.17) | 5.49e-06 |
| | 4 | 4 (0.03) | 243 (0.01) | 2.79 (1.01-7.7) | 4.50e-02 |
| | Trend | 522 | 66767 | | 2.48e-07 |
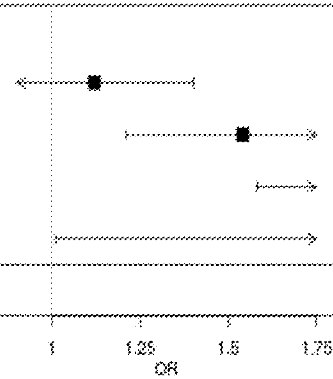
Figure 9 (cont.)

TREATMENT AND INHIBITION OF INFLAMMATORY LUNG DISEASES IN PATIENTS HAVING RISK ALLELES IN THE GENES ENCODING IL33 AND IL1RL1

FIELD

This disclosure relates generally to the field of precision medicine. More particularly, the disclosure relates to the detection of risk alleles in genes encoding IL33 and IL1RL1, which risk alleles can be used to stratify inflammatory lung disease patients as having a high risk of developing one or more of these conditions and their eosinophilic subtypes.

BACKGROUND

Various publications, including patents, published applications, accession numbers, technical articles and scholarly articles are cited throughout the specification. Each of these cited publications is incorporated by reference, in its entirety and for all purposes, in this document.

Asthma and Chronic Obstructive Pulmonary Disease (COPD) are highly prevalent obstructive lung diseases with substantial unmet clinical need and significant diagnostic overlap, and there is increasing interest in the intersection of these conditions, termed asthma-COPD overlap syndrome (ACOS). There is a long-standing debate as to whether the two diseases have a shared etiology (the so-called "Dutch Hypothesis") or have independent mechanistic causes (the so-called "British Hypothesis"). Despite recent progress in elucidating genetic contribution to common complex disease risk, including obstructive lung diseases, there is no well-established genetic finding linking asthma to COPD.

Genome-wide association studies (GWAS) have identified common genetic variants at interleukin-33 (IL33) and/or IL1RL1 that are associated with asthma. IL33, a pro-inflammatory cytokine and member of the interleukin-1 (IL-1) cytokine family, is expressed in subsets of cells in barrier tissues, including the lung epithelium. IL33 signals via a heterodimeric receptor complex composed of the IL33-specific receptor IL1RL1 (also known as ST2 or IL33R) and the IL-1RAcP co-receptor, common to several receptors of the IL-1 family.

In damaged tissues, previously sequestered IL33 is passively released into the extracellular compartment by necrotic cells and functions as an endogenous "danger signal" (alarmin) that activates inflammatory and repair pathways. Cigarette smoke induces IL33 expression in lung epithelial cells in mice, and IL33 expression is elevated in the bronchial epithelium of both asthma and COPD patients. In disease states in which inflammatory infiltrate and inflammatory cytokines are already present, the pool of IL33-responsive cells is increased and IL33 signaling further amplifies immune responses, resulting in pathologic inflammation and exaggerated immune responses, potentially driving chronic inflammatory diseases such as COPD.

There is also an asthma-COPD overlap syndrome (ACOS), characterized by symptoms common to both asthma and COPD. Nevertheless, clinical challenges remain in the capacity to diagnose ACOS, given the difficulty in separating asthma from COPD owing to the overlapping features in common.

Treatment challenges for asthma, COPD, and ACOS also remain, with resistance to corticosteroids (the standard of care) fairly commonplace. As well, other treatments such as IL-5 therapy has not worked well for the eosinophilic subsets of asthma and COPD.

Accordingly, there remains a need in the art to distinguish among asthma, COPD, and ACOS, as well as to more accurately identify patients who have the eosinophilic subsets of these disorders. Proper diagnoses can better direct a therapeutic regimen and improve patient outcomes.

SUMMARY

In a first aspect of the disclosure, a method for treating or inhibiting eosinophilic asthma comprises administering an IL33 antagonist or administering an IL33 antagonist and an IL-4R antagonist to a subject having one or more risk alleles associated with eosinophilic asthma in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof. Administration of an IL33 antagonist and/or an IL-4R antagonist is such that eosinophilic asthma is treated or inhibited in the subject.

In a second aspect of the disclosure, a method for treating or inhibiting eosinophilic Chronic Obstructive Pulmonary Disease (COPD) comprises administering an IL33 antagonist or administering an IL33 antagonist and an IL-4R antagonist to a subject having one or more risk alleles associated with eosinophilic COPD in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof. Administration of an IL33 antagonist and/or an IL-4R antagonist is such that eosinophilic COPD is treated or inhibited in the subject.

In a third aspect of the disclosure, a method for treating or inhibiting eosinophilic asthma-Chronic Obstructive Pulmonary Disease (COPD) overlap syndrome (ACOS), comprising administering an IL33 antagonist or administering an IL33 antagonist and an IL-4R antagonist to a subject having one or more risk alleles associated with eosinophilic asthma in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof. Administration of an IL33 antagonist and/or an IL-4R antagonist is such that eosinophilic COPD is treated or inhibited in the subject.

In a fourth aspect of the disclosure, a method for treating or inhibiting nasal polyps comprises administering an IL33 antagonist or administering an IL33 antagonist and an IL-4R antagonist to a subject having one or more risk alleles associated with nasal polyps in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof. Administration of an IL33 antagonist and/or an IL-4R antagonist is such that nasal polyps are treated or inhibited in the subject.

In a fifth aspect of the disclosure, a method for assessing risk of development of eosinophilic asthma, eosinophilic Chronic Obstructive Pulmonary Disease (COPD), or eosinophilic asthma COPD overlap syndrome (ACOS) comprises the steps of:

(A) detecting one or more risk alleles associated with eosinophilic asthma, eosinophilic COPD, or eosinophilic ACOS in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof in a sample obtained from a subject;

(B) (i) assigning a risk score of 1 to the subject when the subject has a risk allele in the intronic IL1RL1 variant rs1420101 (SEQ ID NO: 357) or variant in linkage disequilibrium thereof in one of the chromosome 2 homologs or a risk allele in the IL33 variant rs1342326 (SEQ ID NO: 358) or variant in linkage disequilibrium thereof in one of the chromosome 9 homologs, (B) (ii) assigning a risk score of 2 to the subject when the subject has a risk allele in the intronic IL1RL1 variant rs1420101 (SEQ ID NO: 357) or variant in linkage disequilibrium thereof in both of the chromosome 2 homologs, when the subject has a risk allele in the IL33 variant rs1342326 (SEQ ID NO: 358) or variant in linkage disequilibrium thereof in both of the chromosome 9 homologs, or when the subject has a risk allele in the intronic IL1RL1 variant rs1420101 (SEQ ID NO: 357) or variant in linkage disequilibrium thereof in one of the chromosome 2 homologs and a risk allele in the IL33 variant rs1342326 (SEQ ID NO: 358) or variant in linkage disequilibrium thereof in one of the chromosome 9 homologs, (B) (iii) assigning a risk score of 3 to the subject when the subject has a risk allele in the intronic IL1RL1 variant rs1420101 (SEQ ID NO: 357) or variant in linkage disequilibrium thereof in both of the chromosome 2 homologs and a risk allele in the IL33 variant rs1342326 (SEQ ID NO: 358) or variant in linkage disequilibrium thereof in one of the chromosome 9 homologs, or when the subject has a risk allele in the intronic IL1RL1 variant rs1420101 (SEQ ID NO: 357) or variant in linkage disequilibrium thereof in one of the chromosome 2 homologs and a risk allele in the IL33 variant rs1342326 (SEQ ID NO: 358) or variant in linkage disequilibrium thereof in both of the chromosome 9 homologs, or (B) (iv) assigning a risk score of 4 to the subject when the subject has a risk allele in the intronic IL1RL1 variant rs1420101 (SEQ ID NO: 357) or variant in linkage disequilibrium thereof in both of the chromosome 2 homologs and a risk allele in the IL33 variant rs1342326 (SEQ ID NO: 358) or variant in linkage disequilibrium thereof in both of the chromosome 9 homologs; and (C) categorizing the subject's risk of development of eosinophilic asthma, eosinophilic COPD, or eosinophilic ACOS, wherein a risk score of 1 indicates that the subject has a risk of developing the high-eosinophilic subset of eosinophilic asthma, high-eosinophilic subset of eosinophilic COPD, or high-eosinophilic subset of eosinophilic ACOS, a risk score of 2 indicates that the subject has an elevated risk of developing the high-eosinophilic subset of eosinophilic asthma, high-eosinophilic subset of eosinophilic COPD, or high-eosinophilic subset of eosinophilic ACOS, a risk score of 3 indicates that the subject has a high risk of developing the high-eosinophilic subset of eosinophilic asthma, high-eosinophilic subset of eosinophilic COPD, or high-eosinophilic subset of eosinophilic ACOS, and a risk score of 4 indicates that the subject has a very high risk of developing the high-eosinophilic subset of eosinophilic asthma, high-eosinophilic subset of eosinophilic COPD, or high-eosinophilic subset of eosinophilic ACOS. The method may further comprise treating or inhibiting one or more of the eosinophilic asthma, eosinophilic COPD, or eosinophilic ACOS, including the high eosinophilic subset thereof, in the subject by administering to the subject an IL33 antagonist or an IL33 antagonist and an IL-4R antagonist.

In a sixth aspect of the disclosure, an IL33 antagonist or a combination of an IL33 antagonist and an IL-4R antagonist is for use in the treatment or inhibition of, or in the manufacture of a medicament for the treatment or inhibition of any one of eosinophilic asthma, eosinophilic Chronic Obstructive Pulmonary Disease (COPD), eosinophilic asthma-Chronic Obstructive Pulmonary Disease overlap syndrome (ACOS), high-eosinophil eosinophilic asthma, high-eosinophil eosinophilic COPD, high-eosinophil eosinophilic ACOS, or nasal polyps when a patient thereof has one or more risk alleles associated with eosinophilic asthma, eosinophilic COPD, or eosinophilic ACOS in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof.

According to any one of these aspects, the subject may have at least one risk allele associated with eosinophilic asthma in the intronic IL1RL1 variant rs1420101 (SEQ ID NO: 357) or variant in linkage disequilibrium thereof, may have two risk alleles associated with eosinophilic asthma in the intronic IL1RL1 variant rs1420101 (SEQ ID NO: 357) or variant in linkage disequilibrium thereof, may have at least one risk allele associated with eosinophilic asthma in the IL33 variant rs1342326 (SEQ ID NO: 358) or variant in linkage disequilibrium thereof, or may have two risk alleles associated with eosinophilic asthma in the IL33 variant rs1342326 (SEQ ID NO: 358) or variant in linkage disequilibrium thereof, and may have further at least one risk allele associated with eosinophilic asthma in the IL33 variant rs1342326 (SEQ ID NO: 358) or variant in linkage disequilibrium thereof, and/or may further have two risk alleles associated with eosinophilic asthma in the IL33 variant rs1342326 (SEQ ID NO: 358) or variant in linkage disequilibrium thereof.

According to any one of these aspects, the method may comprise or the use may be for administering an IL33 antagonist to the subject or the method may comprise or the use may be for administering an IL33 antagonist and an IL-4R antagonist to the subject. The IL33 antagonist may comprise an IL33 trap or an antibody that specifically binds to IL33. The IL-4R antagonist may comprise an antibody that specifically binds to IL-4R.

According to any of these aspects, the IL33 trap may comprise a first IL33 binding domain comprising an IL33 binding portion of IL1RL1 and a second IL33 binding domain comprising an extracellular portion of IL-1RAcP. According to any of these aspects, the antibody or antigen-binding fragment thereof that specifically binds to IL33 may comprise the H1, H2, and H3 domains of SEQ ID NO: 274 and the L1, L2, and L3 domains of SEQ ID NO: 282. According to any of these aspects, the antibody or antigen-binding fragment thereof that specifically binds to IL-4R may comprise the H1, H2, and H3 domains of SEQ ID NO: 337 and the L1, L2, and L3 domains of SEQ ID NO: 338.

BRIEF DESCRIPTION OF THE DRAWINGS

FIG. 8 (Panels A, B, C, and D) shows the clinical characteristics of study participants stratified by capture reagent (Panel A) VCRome and (Panel B) xGEN, and chip platform (Panel C) OMNI and (Panel D) GSA.

DETAILED DESCRIPTION

Figure 1:
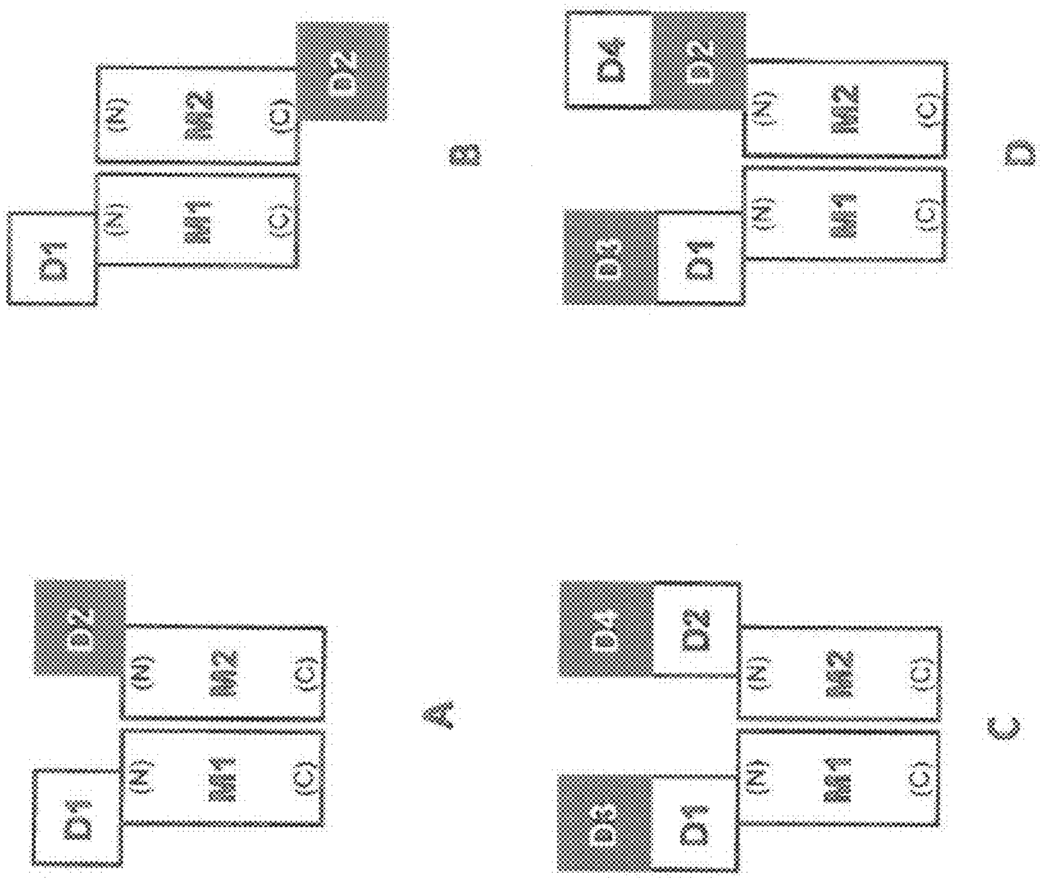
FIG. 1 (Panels A, B, C, and D) shows four exemplary arrangements of the individual components of the IL33 antagonists relative to one another. Panel A shows an arrangement in which a first IL33-binding domain (D1) is attached to the N-terminus of a first multimerizing domain (M1), and a second IL33-binding domain (D2) is attached to the N-terminus of a second multimerizing domain (M2). D1 is shown as a white box and D2 is shown as a black box to indicate that D1 and D2 are derived from different IL33 binding proteins. Panel B shows an arrangement in which a first IL33-binding domain (D1) is attached to the N-terminus of a first multimerizing domain (M1), and a second IL33-binding domain (D2) is attached to the C-terminus of a second multimerizing domain (M2). D1 is shown as a white box and D2 is shown as a black box to indicate that D1 and D2 are derived from different IL33 binding proteins. Panels C and D show arrangements comprising four IL33-binding domains, D1, D2, D3 and D4. In these arrangements, D3-D1-M1 and D4-D2-M2 are attached in tandem, wherein D3 is attached to the N-terminus of D1, and D1 is attached to the N-terminus of M1; and D4 is attached to the N-terminus of D2, and D2 is attached to the N-terminus of M2. In Panel C, D3 and D4 are identical or substantially identical to one another, and D1 and D2 are identical or substantially identical to one another. In Panel D, D1 and D4 are identical or substantially identical to one another, and D3 and D2 are identical or substantially identical to one another.

Various terms relating to aspects of disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The terms "subject" and "patient" are used interchangeably and include any animal. Mammals are preferred, including companion (e.g., cat, dog) and farm mammals (e.g., pig, horse, cow), as well as rodents, including mice, rabbits, and rats, guinea pigs, and other rodents. Non-human primates are more preferred, and human beings are highly preferred.

The term "isolated" means removed and/or altered from the natural environment by the hand of a human being.

A "risk allele" includes alternative polymorphisms at a particular position that associate with a risk of developing a disease, disorder, or condition.

"Linkage disequilibrium" refers to a nonrandom association of alleles at two or more loci.

It has been observed in accordance with the disclosure that single nucleotide polymorphisms in IL1R1 rs1420101 (SEQ ID NO: 357) and IL33 rs1342326 (SEQ ID NO: 358) associate with increased risk of asthma, as well as high-eosinophil subsets of asthma, COPD, and ACOS. In addition, it was observed that individuals carrying a larger burden of these risk alleles across both loci have an attendant larger disease risk and, heterozygous carriers of rare pLOF variants in IL33 had lower median lifetime eosinophil counts and trends reflecting decreased risk of asthma, as well as trends reflecting decreased risks high-eosinophil subsets of asthma, COPD, and ACOS. It is believed that IL33 pathway genetic variants have not been previously associated with COPD and, it is further believed that there have not been any reported genetic links between asthma and COPD or genetic links between the IL33 pathway the risk of high-eosinophil subsets of asthma, COPD and ACOS. Furthermore, it was observed that single nucleotide polymorphisms in IL1R1 rs1420101 and IL33 rs1342326, considered individually and in aggregate, associate with increased risk of nasal polyps and allergic rhinitis. These data indicate a role for interleukin-33 blockade in the treatment of high-eosinophil forms of obstructive lung diseases such as asthma, COPD, and ACOS, as well as other upper airways diseases such as nasal polyps and their high-eosinophil subsets. Accordingly, the disclosure features methods for identifying risk, diagnosing, treating, and inhibiting asthma, COPD, and ACOS, especially the high-eosinophil subsets thereof.

In a first aspect, the disclosure features methods for assessing risk of development of an inflammatory lung disease. The inflammatory lung disease may be one or more of asthma, COPD, ACOS, or nasal polyps. The asthma may be eosinophilic asthma or high-eosinophil eosinophilic asthma. The COPD may be eosinophilic COPD or high-eosinophil eosinophilic COPD. The ACOS may be eosinophilic ACOS or high-eosinophil eosinophilic ACOS. In general, the methods comprise detecting one or more risk alleles associated with risk of development of such inflammatory lung diseases.

In some embodiments, the methods comprise detecting one or more risk alleles associated with eosinophilic asthma, eosinophilic COPD, eosinophilic ACOS, or nasal polyps in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof in a sample obtained from a subject, then assigning a risk score of 1 to the subject when the subject has a risk allele in the intronic IL1RL1 variant rs1420101 (SEQ ID NO: 357) or variant in linkage disequilibrium thereof in one of the chromosome 2 homologs or a risk allele in the IL33 variant rs1342326 (SEQ ID NO: 358) or variant in linkage disequilibrium thereof in one of the chromosome 9 homologs, assigning a risk score of 2 to the subject when the subject has a risk allele in the intronic IL1RL1 variant rs1420101 (SEQ ID NO: 357) or variant in linkage disequilibrium thereof in both of the chromosome 2 homologs, when the subject has a risk allele in the IL33 variant rs1342326 (SEQ ID NO: 358) or variant in linkage disequilibrium thereof in both of the chromosome 9 homologs, or when the subject has a risk allele in the intronic IL1RL1 variant rs1420101 (SEQ ID NO: 357) or variant in linkage disequilibrium thereof in one of the chromosome 2 homologs and a risk allele in the IL33 variant rs1342326 (SEQ ID NO: 358) or variant in linkage disequilibrium thereof in one of the chromosome 9 homologs, assigning a risk score of 3 to the subject when the subject has a risk allele in the intronic IL1RL1 variant rs1420101 (SEQ ID NO: 357) or variant in linkage disequilibrium thereof in both of the chromosome 2 homologs and a risk allele in the IL33 variant rs1342326 (SEQ ID NO: 358) or variant in linkage disequilibrium thereof in one of the chromosome 9 homologs, or when the subject has a risk allele in the intronic IL1RL1 variant rs1420101 (SEQ ID NO: 357) or variant in linkage disequilibrium thereof in one of the chromosome 2 homologs and a risk allele in the IL33 variant rs1342326 (SEQ ID NO: 358) or variant in linkage disequilibrium thereof in both of the chromosome 9 homologs, or assigning a risk score of 4 to the subject when the subject has a risk allele in the intronic IL1RL1 variant rs1420101 (SEQ ID NO: 357) or variant in linkage disequilibrium thereof in both of the chromosome 2 homologs and a risk allele in the IL33 variant rs1342326 (SEQ ID NO: 358) or variant in linkage disequilibrium thereof in both of the chromosome 9 homologs.

In some embodiments, the risk allele in the IL33 variant rs1342326 comprises a single nucleotide polymorphism (SNP). In some detailed embodiments, the IL33 variant comprises the SNP 9:6190076:A:C. (Human Genome GRCh38) The variant rs1342326 comprises the following nucleic acid sequence: CCAATCTTTTCTCATGAAGACACCA[G/T]CATGACCTCTTATTCTTA TTTATAT (SEQ ID NO: 358).

In some embodiments, the risk allele in the IL1RL1 variant rs1420101 comprises an SNP. In some detailed embodiments, the IL1RL1 variant comprises the SNP 2:102341256:C:T (Human Genome GRCh38). The variant rs1342326 comprises the following nucleic acid sequence: TATACCATCACAAAGCCTCTCATTA[A/G]ACTTTGAATCCAATGAGTATTACTA (SEQ ID NO: 357).

Detection may be according to any suitable methodology. The risk alleles may be detected, for example, by way of sequencing, genotyping, imputation, probing with complementary nucleic acid probes.

The methods may further comprise categorizing the subject's risk of development of eosinophilic asthma, eosinophilic COPD, or eosinophilic ACOS, wherein a risk score of 1 indicates that the subject has a risk of developing the high-eosinophil subset of eosinophilic asthma, high-eosinophil subset of eosinophilic COPD, or high-eosinophil subset of eosinophilic ACOS, a risk score of 2 indicates that the subject has an elevated risk of developing the high-eosinophil subset of eosinophilic asthma, high-eosinophil subset of eosinophilic COPD, or high-eosinophil subset of eosinophilic ACOS, a risk score of 3 indicates that the subject has a high risk of developing the high-eosinophil subset of eosinophilic asthma, high-eosinophil subset of eosinophilic COPD, or high-eosinophil subset of eosinophilic ACOS, and a risk score of 4 indicates that the subject has a very high risk of developing the high-eosinophil subset of eosinophilic asthma, high-eosinophil subset of eosinophilic COPD, or high-eosinophil subset of eosinophilic ACOS. In this scale, an elevated risk is greater than a risk but lesser than a high risk, and a very high risk is greater than a high risk. Thus, in terms of patient risk of developing disease, risk<elevated risk<high risk<very high risk, or risk score of 1<risk score of 2<risk score of 3<risk score of 4.

The methods may further comprise obtaining a sample from the subject. In general, the sample may comprise any sample from which the risk alleles may be detected. The sample may comprise a tissue sample or sputum. A tissue sample may include peripheral blood, airway or lung tissue.

The methods may further comprise identifying the subject as a candidate for treatment with an IL33 antagonist or a combination of an IL33 antagonist and an IL-4R antagonist. Based on the categorization of the subject's risk as a risk score of 1, risk score of 2, risk score of 3, or risk score of 4, the subject may benefit from a therapeutic regimen that inhibits eosinophilic asthma, eosinophilic COPD, eosinophilic ACOS, or the high eosinophil subsets thereof, or nasal polyps. An inhibitory therapeutic regimen may comprise adjustments in type, dose, dosing frequency, etc. for the IL33 antagonist, as well as whether or not to combine with an IL-4R antagonist and, if so, the type, dose, and dosing frequency, etc. for the IL-4R antagonist, for example, depending on the level of risk.

The methods may further comprise detecting increased levels in eosinophil counts from blood or sputum isolated from the subject. Increased levels are those that are considered above normal levels or above levels typically observed in subjects that have the non-eosinophilic subset of asthma, COPD, or ACOS. The methods may further comprise isolating the blood or sputum from the subject for this purpose.

The methods may further comprise administering an IL33 antagonist or administering an IL33 antagonist and an IL-4R antagonist to the subject. Such administration may be according to an amount effective to inhibit eosinophilic asthma, eosinophilic COPD, or eosinophilic ACOS, or the high-eosinophil subset thereof. In some embodiments, the IL33 antagonist may comprise an IL33 trap. In some embodiments, the IL33 antagonist may comprise an antibody that specifically binds to IL33 or antigen-binding fragment thereof. Suitable IL33 antagonists are described herein. In some embodiments, the IL-4R antagonist may comprise an antibody that specifically binds to IL-4R or antigen-binding fragment thereof. Suitable IL-4R antagonists are described herein.

In a second aspect, the disclosure features methods for treating or inhibiting eosinophilic asthma in a subject in need thereof. The eosinophilic asthma may be the low-eosinophil subset of eosinophilic asthma or may be the high eosinophil subset of eosinophilic asthma.

In some embodiments, the methods comprise administering an IL33 antagonist or administering an IL33 antagonist and an IL-4R antagonist to a subject having one or more risk alleles associated with eosinophilic asthma in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof, such that eosinophilic asthma is treated or inhibited in the subject.

In some embodiments, the IL33 antagonist may comprise an IL33 trap. In some embodiments, the IL33 antagonist may comprise an antibody that specifically binds to IL33 or antigen-binding fragment thereof. Suitable IL33 antagonists are described herein. In some embodiments, the IL-4R antagonist may comprise an antibody that specifically binds to IL-4R or antigen-binding fragment thereof. Suitable IL-4R antagonists are described herein.

In a third aspect, the disclosure features methods for treating or inhibiting eosinophilic COPD in a subject in need thereof. The eosinophilic COPD may be the low-eosinophil subset of eosinophilic COPD or may be the high eosinophil subset of eosinophilic COPD.

In some embodiments, the methods comprise administering an IL33 antagonist or administering an IL33 antagonist and an IL-4R antagonist to a subject having one or more risk alleles associated with eosinophilic COPD in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof, such that eosinophilic COPD is treated or inhibited in the subject.

In some embodiments, the IL33 antagonist may comprise an IL33 trap. In some embodiments, the IL33 antagonist may comprise an antibody that specifically binds to IL33 or antigen-binding fragment thereof. Suitable IL33 antagonists are described herein. In some embodiments, the IL-4R antagonist may comprise an antibody that specifically binds to IL-4R or antigen-binding fragment thereof. Suitable IL-4R antagonists are described herein.

In a fourth aspect, the disclosure features methods for treating or inhibiting eosinophilic ACOS in a subject in need thereof. The eosinophilic ACOS may be the low-eosinophil subset of eosinophilic ACOS or may be the high eosinophil subset of eosinophilic ACOS.

In some embodiments, the methods comprise administering an IL33 antagonist or administering an IL33 antagonist and an IL-4R antagonist to a subject having one or more risk alleles associated with eosinophilic ACOS in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof, such that eosinophilic ACOS is treated or inhibited in the subject.

In some embodiments, the IL33 antagonist may comprise an IL33 trap. In some embodiments, the IL33 antagonist may comprise an antibody that specifically binds to IL33 or antigen-binding fragment thereof. Suitable IL33 antagonists are described herein. In some embodiments, the IL-4R antagonist may comprise an antibody that specifically binds to IL-4R or antigen-binding fragment thereof. Suitable IL-4R antagonists are described herein.

In any of the methods described or exemplified herein, an IL33 antagonist may be administered as part of a therapeutic regimen. An IL33 antagonist may comprise any agent that inhibits the interaction of IL33 with one or more of its binding partners and, in so doing, inhibit IL33-mediated signaling. For example, an IL33 antagonist may bind to and/or interact with IL33, or with the IL33 receptor referred to as "suppression of tumorigenicity" (aka ST2), or with the IL33 co-receptor Interleukin-1 Receptor Accessory Protein (IL-1RAcP), or with a complex of any of the following: IL33/ST2, or ST2/IL-1RAcP.

Non-limiting examples of categories of IL33 antagonists include small molecule IL33 inhibitors, or receptor antagonists, or nucleic acids that hybridize under stringent conditions to nucleic acid sequences encoding either IL33, or an IL33 receptor or co-receptor (e.g., short interfering RNAs (siRNA) or clustered regularly interspaced short palindromic repeat RNAs (CRISPR-RNA or crRNA), including single guide RNAs (sgRNAs) having a crRNA and tracrRNA sequence. Other IL33 antagonists include proteins comprising a ligand-binding portion of an IL33 receptor (e.g., ST2), IL33-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, and anti-IL33 aptamers or portions thereof.

In preferred embodiments, an IL33 antagonist comprises an antibody that specifically binds to human IL33 (IL33 antibodies), or antigen-binding fragments thereof. The amino acid sequence identifiers for exemplary anti-IL33 antibodies for use in the methods described herein are shown in Table 1. Anti-IL33 antibodies may comprise any antibody described in U.S. Pat. No. 9,453,072, which is incorporated by reference in its entirety.

TABLE 1

| IL33 Antibodies Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1M9559N | 2 | 4 | 6 | 8 | 10 | 12 | 14 | 16 |
| H1M9566N | 18 | 20 | 22 | 24 | 26 | 28 | 30 | 32 |
| H1M9568N | 34 | 36 | 38 | 40 | 42 | 44 | 46 | 48 |
| H4H9629P | 50 | 52 | 54 | 56 | 58 | 60 | 62 | 64 |
| H4H9633P | 66 | 68 | 70 | 72 | 74 | 76 | 78 | 80 |
| H4H9640P | 82 | 84 | 86 | 88 | 90 | 92 | 94 | 96 |
| H4H9659P | 98 | 100 | 102 | 104 | 106 | 108 | 110 | 112 |
| H4H9660P | 114 | 116 | 118 | 120 | 122 | 124 | 126 | 128 |
| H4H9662P | 130 | 132 | 134 | 136 | 138 | 140 | 142 | 144 |
| H4H9663P | 146 | 148 | 150 | 152 | 154 | 156 | 158 | 160 |
| H4H9664P | 162 | 164 | 166 | 168 | 170 | 172 | 174 | 176 |
| H4H9665P | 178 | 180 | 182 | 184 | 186 | 188 | 190 | 192 |
| H4H9666P | 194 | 196 | 198 | 200 | 202 | 204 | 206 | 208 |
| H4H9667P | 210 | 212 | 214 | 216 | 218 | 220 | 222 | 224 |
| H4H9670P | 226 | 228 | 230 | 232 | 234 | 236 | 238 | 240 |
| H4H9671P | 242 | 244 | 246 | 248 | 250 | 252 | 254 | 256 |
| H4H9672P | 258 | 260 | 262 | 264 | 266 | 268 | 270 | 272 |
| H4H9675P | 274 | 276 | 278 | 280 | 282 | 284 | 286 | 288 |
| H4H9676P | 290 | 292 | 294 | 296 | 298 | 300 | 302 | 304 |
| H1M9565N | 308 | 310 | 312 | 314 | 316 | 318 | 320 | 322 |

In some embodiments, the IL33 antagonist comprises an anti-IL33 antibody, or antigen-binding fragment thereof, comprising a heavy chain variable region (HCVR), light chain variable region (LCVR), and/or complementarity determining regions (CDRs) of the amino acid sequences of the anti-IL33 antibodies as set forth in U.S. Pat. No. 9,453,072 and in Table 1 herein. In some embodiments, the IL33 antagonist comprises the heavy chain complementarity determining regions (CDR; e.g., H1, H2, H3) of the heavy chain variable region comprising the amino acid sequence of SEQ ID NO: 274 and the light chain CDRs (e.g., L1, L2, L3) of the light chain variable region comprising the amino acid sequence of SEQ ID NO: 282. In some embodiments, the H1 comprises the amino acid sequence of SEQ ID NO: 276, the H2 comprises the amino acid sequence of SEQ ID NO: 278, and the H3 comprises the amino acid sequence of SEQ ID NO: 280. In some embodiments, the L1 comprises the amino acid sequence of SEQ ID NO: 284, the L2 comprises the amino acid sequence of SEQ ID NO: 286, and the L3 comprises the amino acid sequence of SEQ ID NO: 288. In yet other embodiments, the anti-IL33 antibody or antigen-binding fragment thereof comprises an HCVR comprising SEQ ID NO: 274 and an LCVR comprising SEQ ID NO: 282.

In some embodiments, the IL33 antibodies or antigen-binding fragments thereof comprise three heavy chain CDRs (HCDR1, HCDR2 and HCDR3) contained within a heavy chain variable region (HCVR) amino acid sequence selected from the group consisting of SEQ ID NO: 2, 18, 34, 50, 66, 82, 98, 114, 130, 146, 162, 178, 194, 210, 226, 242, 258, 274, 290, and 308; and comprises three light chain CDRs (LCDR1, LCDR2 and LCDR3) contained within a light chain variable region (LCVR) amino acid sequence selected from the group consisting of SEQ ID NOs: 10, 26, 42, 58, 74, 90, 106, 122, 138, 154, 170, 186, 202, 218, 234, 250, 266, 282, 298, and 316.

In some embodiments, the anti-IL33 antibodies, or antigen-binding fragments thereof comprise a HCVR and LCVR (HCVR/LCVR) sequence pair of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, or 308/316.

In some embodiments, the anti-IL33 antibodies, or antigen-binding fragments thereof comprise a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, and 310, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, and 312, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, and 318, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, and 320, or a substantially similar sequence thereof having at least 90%, at least 95%, at least 98% or at least 99% sequence identity.

In some preferred embodiments, the anti-IL33 antibodies or antigen-binding fragments thereof comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M9559N); 20-22-24-28-30-32 (e.g., H1M9566N); 36-38-40-44-46-48 (e.g., H1M9568N); 52-54-56-60-62-64 (e.g. H4H9629P); 68-70-72-76-78-80 (e.g., H4H9633P); 84-86-88-92-94-96 (e.g. H4H9640P); 100-102-104-108-110-112 (e.g., H4H9659P); 116-118-120-124-126-128 (e.g., H4H9660P); 132-134-136-140-142-144 (e.g., H4H9662P); 148-150-152-156-158-160 (e.g., H4H9663P); 164-166-168-

172-174-176 (e.g., H4H9664P); 180-182-184-188-190-192 (e.g., H4H9665P); 196-198-200-204-206-208 (e.g., H4H9666P); 212-214-216-220-222-224 (e.g., H4H9667P); 228-230-232-236-238-240 (e.g., H4H9670P); 244-246-248-252-254-256 (e.g., H4H9671P); 260-262-264-268-270-272 (e.g., H4H9672P); 276-278-280-284-286-288 (e.g., H4H9675P); 292-294-296-300-302-304 (e.g., H4H9676P); and 310-312-314-318-320-322 (H1M9565N).

In some embodiments, the anti-IL33 antibodies, or antigen-binding fragments thereof, comprise the heavy and light chain CDR domains contained within heavy and light chain variable region (HCVR/LCVR) sequences of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, or 308/316. The boundaries of CDRs may be according to the Kabat definition, the Chothia definition, or the AbM definition.

Other anti-IL33 antibodies and antigen-binding fragments thereof that may be used in the methods described herein are disclosed in European Publ. No. EP 1725261, PCT Publ. Nos. WO 2011/031600, WO 2015/099175, WO 2015/106080 (ANB020), WO 2016/077381, WO 2016/077366, or WO2016/156440, U.S. Pat. No. 8,187,596, and U.S. Publ. No. 2016/0168242, which are each incorporated herein by reference in their entirety.

In alternative preferred embodiments, an IL33 antagonist comprises an IL33 trap. IL33 traps comprise at least one IL33 binding domain, which comprises an IL33 binding portion of an IL33 receptor protein, designated ST2. In some embodiments, an IL33 trap further comprises an extracellular portion of an IL33 co-receptor, designated IL-1 receptor accessory protein, or IL-1RAcP. The IL33 trap may also comprise at least one multimerizing component, which functions to connect the various components of the trap with one another. The various components of the IL33 traps are described below and shown in FIG. 1. IL33 traps may comprise any trap described in U.S. Publ. No. 2014/0271642 and PCT Publ. No. WO 2014/152195, which are each incorporated herein by reference in their entirety.

The IL33 trap may comprise a first IL33 binding domain (D1) attached to a multimerizing domain (M). In some embodiments, the IL33 trap comprises a second IL33 binding domain (D2) attached to D1 and/or M. In some preferred embodiments, D1 comprises an IL33-binding portion of an ST2 protein. In some preferred embodiments, D2 comprises an extracellular portion of an IL-1RAcP protein.

The individual components of the IL33 traps may be arranged relative to one another in a variety of ways that result in functional antagonist molecules capable of binding IL33. For example, D1 and/or D2 may be attached to the N-terminus of M. In some embodiments, D1 and/or D2 is attached to the C-terminus of M. In other embodiments, D1 is attached to the N-terminus of D2, and D2 is attached to the N-terminus of M, resulting in an in-line fusion, from N- to C-terminus, of an antagonist molecule represented by the formula D1-D2-M. Other orientations of the individual components are disclosed elsewhere herein in FIG. 1.

The IL33 traps comprise at least one IL33 binding domain (sometimes referred to herein by the designation "D," or "D1," "D2," etc.). In some embodiments, the IL33 binding domain comprises an IL33-binding portion of an ST2 protein. An IL33-binding portion of an ST2 protein can comprise or consist of all or part of the extracellular domain of an ST2 protein. In preferred embodiments, an ST2 protein is a human ST2 protein, including the ST2 protein of amino acids 1-556 of accession number NP_057316.3 (SEQ ID NO: 352). In some alternative embodiments, the ST2 protein comprises an ST2 protein from a non-human species (e.g., mouse ST2, non-human primate ST2, etc.). An preferred IL33-binding portion of an ST2 protein is set forth herein as the amino acid sequence of SEQ ID NO: 328 (corresponding to the extracellular domain of human ST2 [K19-5328 of NCBI Accession No. NP_057316.3]). Other examples of an IL33-binding portion of an ST2 protein is set forth herein as the amino acid sequence of SEQ ID NO: 329 (corresponding to the extracellular domain of mouse ST2 [S27-R332 of NCBI Accession No. P14719]).

In some embodiments, the IL33 binding domain of the trap comprises an extracellular portion of an IL-1RAcP protein. In certain embodiments, an IL-1RAcP protein comprises a human IL-1RAcP protein, including an IL-1RAcP protein having the amino acid sequence of SEQ ID NO: 353. In some alternative embodiments, the IL-1RAcP protein comprises an IL-1RAcP protein from a non-human species (e.g., mouse IL-1RAcP, non-human primate IL-1RAcP, etc.). An exemplary extracellular portion of an IL-1RAcP protein is set forth herein as the amino acid sequence of SEQ ID NO: 330 (corresponding to the extracellular domain of human IL-1RAcP [S21-E359 of NCBI Accession No. Q9NPH3]). Another example of an extracellular portion of an IL-1RAcP protein is set forth herein as the amino acid sequence of SEQ ID NO: 331 (corresponding to the extracellular domain of mouse IL-1RAcP [S21-E359 of NCBI Accession No. Q61730]).

Non-limiting examples of IL33 traps for use in the methods are shown in Table 2, and include the IL33 traps designated "hST2-hFc," "hST2-mFc," "hST2-hIL1RAcP-mFc," "hST2-hIL1RAcP-hFc" and "mST2-mIL1RAcP-mFc." These correspond to SEQ ID NOs: 323, 324, 325, 326 and 327, respectively. IL33 receptor based traps may comprise an amino acid sequence that is at least about 80%, 85%, 90%, 91%, 92%, 93%, 94%, 95%, 96%, 97%, 98% or 99% identical to any of the exemplary IL33 receptor based traps set forth herein (e.g., SEQ ID NOs: 323, 324, 325, 326 and 327). IL33 traps may comprise D1 and/or D2 components having an amino acid sequence that is at least about 80%, 85%, 90%, 91%, 92%, 93%, 94%, 95%, 96%, 97%, 98% or 99% identical to any of the exemplary IL33 binding domain component amino acid sequences set forth herein (e.g., SEQ ID NOs: 328, 329, 330 and 331).

Five different exemplary IL33 traps were constructed. The first IL33 antagonist (hST2-hFc, SEQ ID NO: 323) includes the soluble extracellular region of human ST2 (SEQ ID NO: 328) fused at its C-terminus to the N-terminus of a human IgG1 Fc region (SEQ ID NO:332). The second IL33 antagonist (hST2-mFc, SEQ ID NO:324) consists of the soluble extracellular region of human ST2 (SEQ ID NO:328) fused at its C-terminus to the N-terminus of a mouse IgG2a Fc region (SEQ ID NO:333). The third IL33 antagonist (hST2-hIL1RAcP-mFc, SEQ ID NO: 325) consists of an in-line fusion having human ST2 (SEQ ID NO:328) at its N-terminus, followed by the extracellular region of human IL-1RAcP (SEQ ID NO:330), followed by a mouse IgG2a Fc (SEQ ID NO:333) at its C-terminus. The fourth IL33 antagonist (mST2-mIL1RAcP-mFc, SEQ ID NO: 326) consists of an in-line fusion having mouse ST2 (SEQ ID NO:329) at its N-terminus, followed by the extracellular region of mouse IL-1RAcP (SEQ ID NO:331), followed by a mouse IgG2a Fc (SEQ ID NO:333) at its C-terminus. The fifth IL33 antagonist (hST2-hIL1RAcP-hFc, SEQ ID NO:327) consists of an in line fusion having human ST2 of SEQ ID NO: 328 at its N-terminus, followed by the extracellular region of human IL-1RAcP (SEQ ID NO: 330) followed by a human IgG1 Fc (SEQ ID NO: 332) at its C terminus. See, Table 2.

TABLE 2

Summary of IL33 Antagonists and the Component Parts

| IL33 Antagonist | Amino Acid Sequence of Full Antagonist Molecule | D1 Component | D2 Component | M Component |
|---|---|---|---|---|
| hST2-hFc | SEQ ID NO: 323 | human ST2 extracellular (SEQ ID NO: 328) | Absent | human IgG1 Fc (SEQ ID NO: 332) |
| hST2-mFc | SEQ ID NO: 324 | human ST2 extracellular (SEQ ID NO: 328) | Absent | mouse IgG2a Fc (SEQ ID NO: 333) |
| hST2-hIL1RAcP-mFc | SEQ ID NO: 325 | human ST2 extracellular (SEQ ID NO: 328) | human IL-1RAcP extracellular (SEQ ID NO: 330) | mouse IgG2a Fc (SEQ ID NO: 333) |
| mST2-mIL1RAcP-mFc | SEQ ID NO: 326 | mouse ST2 extracellular (SEQ ID NO: 329) | mouse IL-1RAcP extracellular (SEQ ID NO: 331) | mouse IgG2a Fc (SEQ ID NO: 333) |
| hST2-hIL1RAcP-hFc | SEQ ID NO: 327 | human ST2 extracellular (SEQ ID NO: 328) | human IL-1RAcP extracellular (SEQ ID NO: 330) | human IgG1 Fc (SEQ ID NO: 332) |

The IL33 traps may comprise at least one multimerizing domain (sometimes referred to herein by the abbreviation "M," "M1," "M2," etc.). In general terms, the multimerizing domain(s) function to connect the various components of the IL33 antagonists (e.g., the IL33-binding domain(s)) with one another. A multimerizing domain may comprise any macromolecule that has the ability to associate (covalently or non-covalently) with a second macromolecule of the same or similar structure or constitution. For example, a multimerizing domain may comprise a polypeptide comprising an immunoglobulin CH3 domain. A non-limiting example of a multimerizing domain is an Fc portion of an immunoglobulin, e.g., an Fc domain of an IgG selected from the isotypes IgG1, IgG2, IgG3, and IgG4, as well as any allotype within each isotype group.

Non-limiting exemplary multimerizing domains that can be used in the IL33 traps include human IgG1 Fc (SEQ ID NO: 332) or mouse IgG2a Fc (SEQ ID NO: 333). IL33 traps may comprise M components having an amino acid sequence that is at least about 80%, 85%, 90%, 91%, 92%, 93%, 94%, 95%, 96%, 97%, 98% or 99% identical to any of the exemplary M component amino acid sequences set forth herein (e.g., SEQ ID NOs: 332 or 333).

In some embodiments, the IL33 traps comprise two multimerizing domains, M1 and M2, wherein M1 and M2 are identical to one another. For example, M1 can be an Fc domain having a particular amino acid sequence, and M2 is an Fc domain with the same amino acid sequence as M1. The individual components of the IL33 antagonists (e.g., D1, D2, M, etc.) can be arranged relative to one another in a variety of ways. Non-limiting examples of all of the above noted arrangements, including an example of an IL33 trap comprising two multimerizing domains (M1 and M2) and four IL33 binding domains (D1, D2, D3 and D4,) are illustrated schematically in FIG. 1.

The individual components of the IL33 traps (e.g., D1, D2, M1, M2, etc.) may be attached to one another directly (e.g., D1 and/or D2 may be directly attached to M, etc.); alternatively, the individual components may be attached to one another via a linker component (e.g., D1 and/or D2 may be attached to M via a linker oriented between the individual components; D1 may be attached to D2 via a linker; etc.).

Polypeptides that bind IL33 and/or its receptor (ST2 and/or IL-1 RAcP) and block ligand-receptor interaction are considered as IL33 antagonists and are disclosed in PCT Publ. No. WO 2014/152195, which is incorporated by reference in its entirety. The biological characteristics of the IL33 traps are described in U.S. Publ. No. 2014/0271642, which is incorporated by reference herein in their entirety.

Other agents that may act as IL33 antagonists and which may be used in the methods include immunoadhesins, peptibodies, and soluble ST2, or derivatives thereof; anti-IL33 receptor antibodies (e.g., anti-ST2 antibodies, for example, AMG-282 (Amgen) or STLM15 (Janssen) or any of the anti-ST2 antibodies described in PCT Publ. Nos. WO 2012/113813, WO 2013/173761, and WO 2013/165894, as well as U.S. Pat. Nos. 8,444,987 and 7,452,980, which are each incorporated herein by reference in their entirety. Other IL33 antagonists include ST2-Fc proteins, such as those described in PCT Publ. Nos. WO 2013/173761 and WO 2013/165894, which are each incorporated herein by reference in their entirety.

In any of the methods described or exemplified herein, an IL-4R antagonist may be administered as part of a therapeutic regimen. The IL-4R antagonist is preferably administered in combination with the IL33 antagonist, though the IL-4R antagonist need not be administered at the same time as the IL33 antagonist. An IL-4R antagonist may comprise any agent that binds to or interacts with IL-4Ra or an IL-4R ligand, and inhibits or attenuates the normal biological signaling function of a type 1 and/or a type 2 IL-4 receptor. The IL-4R may comprise the amino acid sequence of SEQ ID NO: 347, or a biologically active fragment thereof. A type 1 IL-4 receptor is a dimeric receptor comprising an IL-4Ra chain and a γc chain. A type 2 IL-4 receptor is a dimeric receptor comprising an IL-4Ra chain and an IL-13Rα1 chain. Type 1 IL-4 receptors interact with and are stimulated by IL-4, while type 2 IL-4 receptors interact with and are stimulated by both IL-4 and IL-13. Thus, the IL-4R antagonists used in the methods may function by blocking IL-4-mediated signaling, IL-13-mediated signaling, or both IL-4- and IL-13-mediated signaling. The IL-4R antagonists may thus inhibit or prevent the interaction of IL-4 and/or IL-13 with a type 1 or type 2 receptor.

Non-limiting examples of categories of IL-4R antagonists include small molecule IL-4R antagonists, nucleic acid-based inhibitors of IL-4R expression or activity (e.g., siRNA or antisense), peptide-based molecules that specifically interact with IL-4R (e.g., peptibodies), "receptor-bodies" (e.g., engineered molecules comprising the ligand-binding domain of an IL-4R component), IL-4R-binding scaffold molecules (e.g., DARPins, HEAT repeat proteins, ARM repeat proteins, tetratricopeptide repeat proteins, fibronectin-based scaffold constructs, and other scaffolds based on naturally occurring repeat proteins, and anti-IL-4R aptamers or portions thereof.

In preferred embodiments, an IL-4R antagonist comprises an antibody that specifically binds to human IL-4R. Antibodies are typically referred to herein according to the following nomenclature: Fc prefix (e.g. "H1M," or "H4H"), followed by a numerical identifier (e.g., "9559," "9566," or "9629" as shown in Table 1), followed by a "P," or "N"

suffix. According to this nomenclature, an antibody may be referred to herein as, e.g., "H1M9559N," "H1M9566N," "H4H9629P," etc. The H1M and H4H prefixes on the antibody designations used herein indicate the particular Fc region isotype of the antibody. For example, an "H1M" antibody has a mouse IgG1 Fc, whereas an "H4H" antibody has a human IgG4 Fc. An antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties are expected to be identical or substantially similar regardless of the nature of the Fc In preferred embodiments, the anti-IL-4R antibody is dupilumab. See U.S. Pat. Nos. 7,605,237, 7,608,693, and 9,290,574, which are incorporated by reference.

Human anti-IL-4R antibodies can be generated as described in U.S. Pat. No. 7,608,693. One exemplary IL-4R antibody is a mouse antibody specific for mouse IL-4R, and has the following amino acid sequences: a heavy chain variable region (HCVR) comprising SEQ ID NO: 335 and a light chain variable domain (LCVR) comprising SEQ ID NO: 336. The human anti-IL-4R antibody, referred to as dupilumab, specifically binds to human IL-4Rα and comprises a heavy chain variable region (HCVR) comprising SEQ ID NO: 337 and a light chain variable region (LCVR) comprising SEQ ID NO: 338, a heavy chain complementarity determining region 1 (HCDR1) comprising SEQ ID NO: 339, a HCDR2 comprising SEQ ID NO: 340, a HCDR3 comprising SEQ ID NO: 341, a light chain complementarity determining region 1 (LCDR1) comprising SEQ ID NO: 342, a LCDR2 comprising SEQ ID NO: 343 and a LCDR3 comprising SEQ ID NO: 344. The full-length heavy chain of dupilumab is shown as SEQ ID NO: 345 and the full length light chain is shown as SEQ ID NO: 346.

In some embodiments, the IL-4R antagonist comprises an anti-IL-4Ra antibody, or antigen-binding fragment thereof comprising a heavy chain variable region (HCVR), light chain variable region (LCVR), and/or complementarity determining regions (CDRs) comprising any of the amino acid sequences of the anti-IL-4R antibodies as set forth in U.S. Pat. Nos. 7,605,237 and 7,608,693. In some embodiments, the IL-4R antagonist comprises an anti-IL-4R antibody having the binding characteristics of the reference antibody referred to herein as dupilumab (U.S. Pat. Nos. 7,605,237 and 7,608,693). In some embodiments, the anti-IL-4Rα antibody or antigen-binding fragment thereof comprises the heavy chain complementarity determining regions (HCDRs) of a heavy chain variable region (HCVR) comprising the amino acid sequence of SEQ ID NO: 337 and the light chain complementarity determining regions (LCDRs) of a light chain variable region (LCVR) comprising the amino acid sequence of SEQ ID NO: 338. In some embodiments, the anti-IL-4Ra antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 339; the HCDR2 comprises the amino acid sequence of SEQ ID NO: 340; the HCDR3 comprises the amino acid sequence of SEQ ID NO: 341; the LCDR1 comprises the amino acid sequence of SEQ ID NO: 342; the LCDR2 comprises the amino acid sequence of SEQ ID NO: 343; and the LCDR3 comprises the amino acid sequence of SEQ ID NO: 344. In yet other embodiments, the anti-IL-4R antibody or antigen-binding fragment thereof comprises an HCVR comprising SEQ ID NO: 337 and an LCVR comprising SEQ ID NO: 338. In yet other embodiments, the anti-IL-4R antibody or antigen-binding fragment thereof comprises an HCVR comprising SEQ ID NO: 335 and an LCVR comprising SEQ ID NO: 336. In some embodiments, the anti-IL-4R antibody or antigen-binding fragment thereof comprises a heavy chain (HC) amino acid sequence as set forth in SEQ ID NO: 345 and a light chain (LC) amino acid sequence as set forth in SEQ ID NO: 346.

In some embodiments, the IL-4R antibody or antigen-binding fragment thereof comprises the heavy chain complementarity determining regions (HCDRs) of a heavy chain variable region (HCVR) comprising the amino acid sequence of SEQ ID NO:335 or SEQ ID NO: 337 and the light chain complementarity determining regions (LCDRs) of a light chain variable region (LCVR) comprising the amino acid sequence of SEQ ID NO:336 or SEQ ID NO: 338.

In some embodiments, the IL-4R antibody or antigen-binding fragment thereof comprises three HCDRs (HCDR1, HCDR2 and HCDR3) and three LCDRs (LCDR1, LCDR2 and LCDR3), wherein the HCDR1 comprises the amino acid sequence of SEQ ID NO: 339, the HCDR2 comprises the amino acid sequence of SEQ ID NO:340; the HCDR3 comprises the amino acid sequence of SEQ ID NO:341; the LCDR1 comprises the amino acid sequence of SEQ ID NO:342; the LCDR2 comprises the amino acid sequence of SEQ ID NO:343; and the LCDR3 comprises the amino acid sequence of SEQ ID NO:344.

In some embodiments, the IL-4R antibody or antigen-binding fragment thereof for use in the methods of the disclosure comprises an HCVR comprising the amino acid sequence of SEQ ID NO: 335 or SEQ ID NO: 337 and an LCVR comprising the amino acid sequence of SEQ ID NO: 336 or SEQ ID NO: 338.

In some embodiments, the IL-4R antibody or antigen-binding fragment thereof for use in the methods of the disclosure comprises an HCVR/LCVR amino acid sequence pair of SEQ ID NOs: 335/336 or SEQ ID NOs: 337/338.

Other anti-IL-4Ra antibodies include, for example, the antibody referred to and known in the art as AMG317 (Corren et al., 2010, Am J Respir Crit Care Med., 181(8): 788-796), or MEDI 9314, or any of the anti-IL-4Ra antibodies as set forth in any of U.S. Pat. Nos. 7,186,809, 7,605,237, 7,638,606, 8,092,804, 8,679,487, or 8,877,189.

The anti-IL-4Ra and the IL33 antibodies may have pH-dependent binding characteristics. For example, an anti-IL-4Rα antibody or an anti-IL33 antibody may exhibit reduced binding to IL-4Rα, or to IL33, respectively, at acidic pH as compared to neutral pH. Alternatively, an anti-IL-4Rα antibody or an anti-IL33 antibody may exhibit enhanced binding to its antigen at acidic pH as compared to neutral pH. An "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. A "neutral pH" includes a pH of about 7.0 to about 7.4, as well as about 7.0, 7.05, 7.1, 7.15, 7.2, 7.25, 7.3, 7.35, and 7.4.

In another aspect, an IL33 antagonist is used alone or in combination with an IL-4R antagonist for treating or inhibiting an inflammatory condition of the lungs. The IL33 antagonist or combination may be used for treating or inhibiting one or more of asthma, COPD, or ACOS. The IL33 antagonist or combination may be used for treating or inhibiting nasal polyps. The combination may be used for treating or inhibiting one or more of eosinophilic asthma, eosinophilic COPD, or eosinophilic ACOS. The IL33 antagonist or combination may be used for treating or inhibiting one or more of the high eosinophilic subset of eosinophilic asthma, eosinophilic COPD, or eosinophilic ACOS. The combination demonstrates enhanced efficacy, as compared to the treatment or inhibition obtained when each antibody is used alone as monotherapy.

In some embodiments, an IL33 antagonist or a combination of an IL33 antagonist and an IL-4R antagonist is used in the manufacture of a medicament for the treatment or inhibition of any one of eosinophilic asthma, eosinophilic Chronic Obstructive Pulmonary Disease (COPD), eosinophilic asthma-Chronic Obstructive Pulmonary Disease overlap syndrome (ACOS), high-eosinophil eosinophilic asthma, high-eosinophil eosinophilic COPD, high-eosinophil eosinophilic ACOS, or nasal polyps. In preferred embodiments, the IL33 antagonist or combination is used in the manufacture of a medicament for such treatment or inhibition of any one of eosinophilic asthma, eosinophilic COPD, eosinophilic ACOS, high-eosinophil eosinophilic asthma, high-eosinophil eosinophilic COPD, high-eosinophil eosinophilic ACOS, or nasal polyps when a patient thereof has one or more risk alleles associated with eosinophilic asthma, eosinophilic COPD, or eosinophilic ACOS in the intronic IL1RL1 variant rs1420101 (SEQ ID NO: 357) or variant in linkage disequilibrium thereof, in the IL33 variant rs1342326 (SEQ ID NO: 358) or variant in linkage disequilibrium thereof, or in both the intronic IL1RL1 variant rs1420101 (SEQ ID NO: 357) or variant in linkage disequilibrium thereof and the IL33 variant rs1342326 (SEQ ID NO: 358) or variant in linkage disequilibrium thereof.

According to such use, the IL33 antagonist may comprise an IL33 trap. The IL33 trap may comprise a first IL33 binding domain comprising an IL33 binding portion of IL1RL1 and a second IL33 binding domain comprising an extracellular portion of IL-1RAcP. The IL33 antagonist may alternatively comprise an antibody or antigen-binding fragment thereof that specifically binds to IL33. The antibody or antigen-binding fragment thereof that specifically binds to IL33 may comprise the H1, H2, and H3 domains of SEQ ID NO: 274 and the L1, L2, and L3 domains of SEQ ID NO: 282. The IL-4R antagonist may comprise an antibody or antigen-binding fragment thereof that specifically binds to IL-4R. The antibody or antigen-binding fragment thereof that specifically binds to IL-4R may comprise the H1, H2, and H3 domains of SEQ ID NO: 337 and the L1, L2, and L3 domains of SEQ ID NO: 338.

The following examples are provided to describe the disclosure in greater detail. They are intended to illustrate, not to limit, the disclosure.

Example 1

Anti-IL33 Antibody, Anti-IL-4R Antibody, and a Combination of Both in a Chronic House Dust Mite-Induced Fibrosis and Severe Lung Inflammation Model Chronic inflammatory airway diseases are a consequence of recurrent episodes of airway inflammation predominantly due to repeated exposure to allergens or other pathogens. In humans, such chronic insults induce a vast array of pathologies that include pulmonary infiltration by immune cells, increased cytokine production, mucus production and collagen deposition. This increase in inflammatory cytokines and immune cell infiltrates, accompanied by intense airway remodeling leads to airway narrowing, hyperresponsiveness to inhaled triggers such as allergens or pathogens, airway obstruction and loss of lung function.

To determine the effect of anti-IL33 inhibition in a relevant in vivo model, a chronic house dust mite extract (HDM)-induced fibrosis and severe lung inflammation and remodeling study was conducted in mice that were homozygous for the expression of human IL33 in place of mouse IL33 (IL33 Humin mice). See U.S. Publ. Nos. 2015/0320021 and 2015/0320022. Chronic HDM extract exposure induces severe lung inflammation, resulting in significant cellular infiltrate, cytokine expression, and remodeling. Efficacy of an anti-IL33 antibody, an anti-mouse IL-4Rα antibody or a combination of both was compared in this model. The anti-mouse IL-4Rα antibody used in this study is designated M1M1875N and comprises the HCVR/LCVR amino acid sequence pair of SEQ ID NOs: 335/336. The anti-IL33 antibody used in this study is designated H4H9675P and comprises the HCVR/LCVR amino acid sequence pair of SEQ ID NOs: 274/282.

IL33 Humin mice were intranasally administered either 50 μg house dust mite extract (HDM; Greer, # XPB70D3A2.5) diluted in 20 μL of 1× phosphate buffered saline (PBS), or 20 μL of 1×PBS for 3 days per week for 15 weeks. A second control group of IL33 Humin mice were administered 50 μg HDM extract diluted in 20 μL of 1×PBS for 3 days per week for 11 weeks, to assess the severity of the disease at the onset of antibody treatment. Four groups of HDM challenged mice were injected subcutaneously with 25 mg/kg of either the anti-IL33 antibody H4H9675P, the anti-mouse IL-4Rα antibody M1M1875N, a combination of both antibodies, or an isotype control antibody starting after 11 weeks of HDM challenge and then twice per week until the end of the HDM challenge (4 weeks of antibody treatment). On day 108 of the study, all mice were sacrificed and their lungs were harvested. Experimental dosing and treatment protocol for groups of mice are shown in Table 3.

TABLE 3

Experimental dosing and treatment protocol for groups of mice

| Group | Mice | Intranasal challenge | Length of intranasal challenge | Antibody |
|---|---|---|---|---|
| 1 | IL33 HumIn mice | 1X PBS | 15 weeks | None |
| 2 | IL33 HumIn mice | 50 μg HDM in 20 μL 1X PBS | 11 weeks | None |
| 3 | IL33 HumIn mice | 50 μg HDM in 20 μL 1X PBS | 15 weeks | None |
| 4 | IL33 HumIn mice | 50 μg HDM in 20 μL 1X PBS | 15 weeks | Isotype control antibody |
| 5 | IL33 HumIn mice | 50 μg HDM in 20 μL 1X PBS | 15 weeks | Anti-IL33 antibody (H4H9675P) |
| 6 | IL33 HumIn mice | 50 μg HDM in 20 μL 1X PBS | 15 weeks | Anti-IL-4Rα antibody (M1M1875N) |
| 7 | IL33 HumIn mice | 50 μg HDM in 20 μL 1X PBS | 15 weeks | Anti-IL33 (H4H9675P) antibody + Anti-IL-4Rα (M1M1875N) antibody |

Lung Harvest for Cytokine Analysis.

Elevated lung levels of key mediators such as the prototypic type 2 cytokines IL-4, IL-5, and IL-13, as well as cytokines more characteristic of type 1 immune responses, such as IL-1β or TNFα have been involved in human the development of lung diseases. Lung levels of these inflammatory cytokines were measured in the study.

After exsanguination, the cranial and middle lobes of the right lung from each mouse were removed and placed into tubes containing a solution of tissue protein extraction reagent (1× T-PER reagent; Pierce, #78510) supplemented with 1× Halt Protease inhibitor cocktail (Thermo Scientific, #87786). All further steps were performed on ice. The volume of T-PER Reagent (containing the protease inhibitor cocktail) was adjusted for each sample to match a 1:7 (w/v) tissue to T-PER ratio. Lung samples were mechanically disrupted using the TissueLyser II (Qiagen #85300). The resulting lysates were centrifuged to pellet debris. The supernatants containing the soluble protein extracts were transferred to fresh tubes and stored at 4° C. until further analysis.

Total protein content in the lung protein extracts was measured using a Bradford assay. For the assay, 10 μL of diluted extract samples were plated into 96 well plates in duplicates and mixed with 200 μL of 1× Dye Reagent (Biorad, #500-0006). Serial dilutions of bovine serum albumin (BSA; Sigma, # A7979), starting at 700 μg/mL in 1× T-Per reagent were used as a standard to determine the protein concentration of the extracts. After a 5-minute incubation at room temperature, absorbance at 595 nm was measured on a Molecular Devices SPECTRAMAX® M5 plate reader. Data analysis to determine total lung extract protein content based on the BSA standard was performed using GraphPad Prism™ software.

Cytokine concentrations in the lung protein extracts were measured using a Proinflammatory Panel 1 (mouse) multiplex immunoassay kit (MesoScale Discovery, # K15048G-2) and a custom mouse 6plex MULTI-SPOT® immunoassay kit (MesoScale Discovery, # K152A41-4), according to the manufacturer's instructions. Briefly, 50 μL/well of calibrators and samples (diluted in Diluent 41) were added to plates pre-coated with capture antibodies and incubated at room temperature while shaking at 700 rpm for 2 hours. The plates were then washed 3 times with 1×PBS containing 0.05% (w/v) TWEEN®-20 surfactant, followed by the addition of 25 μL of Detection Antibody Solution diluted in Diluent 45. After a 2 hour incubation at room temperature while shaking, the plate was washed 3 times, and 150 μL of 2× Read Buffer was added to each well. Electrochemiluminescence was immediately read on a MSD Spector instrument. Data analysis was performed using GraphPad Prism software.

Each cytokine concentration in lung total protein extracts from all mice in each group was normalized to the total protein content of the extracts measured by the Bradford assay, and expressed for each group as average pg of cytokine per mg of total lung proteins (pg/mg lung protein, ±SD) as shown in Table 4.

Lung Cytokines Analysis.

As shown in Table 4, the level of the cytokines and chemokines IL-4, IL-5, IL-6, IL-1β and MCP-1 released in the lungs of IL33 Humin mice receiving HDM for 15 weeks, with or without treatment with an isotype control antibody were significantly higher than in IL33 Humin mice challenged with 1×PBS alone. Similarly, there was a trend towards an increased release of the cytokines IL-13 and TNFα in the lungs of IL33 Humin mice receiving HDM for 15 weeks. In contrast, there was a significant reduction in the levels of IL-6, IL-13 and MCP-1 in the lungs of IL33 Humin mice treated with a combination of anti-IL33 and anti-mouse IL-4Rα antibodies during the last four weeks of the chronic HDM challenge as compared to IL33 Humin mice administered HDM with an isotype control antibody during this time period. There was a trend towards reduced IL-4, IL-5, IL-1β and TNFα lung levels in IL33 Humin mice treated with a combination of anti-IL33 and anti-mouse IL-4Rα antibodies during the last four weeks of the chronic HDM challenge as compared to IL33 Humin mice administered HDM with an isotype control antibody during this time period. The effects on lung cytokines observed with the combination anti-IL33 and anti-mouse IL-4Rα antibodies was greater than treatment with either individual antibodies alone.

TABLE 4

Cytokine concentration in lung protein extracts

| Experimental group | Mean [IL-4] in lung protein extracts (pg/mg lung protein) (±SD) | Mean [IL-5] in lung protein extracts (pg/mg lung protein) (±SD) | Mean [IL-13] in lung protein extracts (pg/mg lung protein) (±SD) | Mean [IL-6] in lung protein extracts (pg/mg lung protein) (±SD) | Mean [IL-1β] in lung protein extracts (pg/mg lung protein) (±SD) | Mean [TNFα] in lung protein extracts (pg/mg lung protein) (±SD) | Mean [MCP-1] in lung protein extracts (pg/mg lung protein) (±SD) |
|---|---|---|---|---|---|---|---|
| 1. 1X PBS challenge (n = 5) | 0.13 (±0.17) | 0.80 (±1.41) | ND | 4.75 (±3.39) | 1.97 (±1.67) | 2.86 (±1.01) | 4.12 (±1.12) |
| 2. HDM challenge 11 weeks (n = 4) | 5.71 (±3.76) * | 7.31 (±3.67) | 0.20 (±0.03) | 293.1 (±139.3) * | 181.8 (±131.0) * | 17.39 (±8.90) | 43.06 (±24.21) |
| 3. HDM challenge 15 weeks (n = 4) | 2.70 (±1.71) | 5.13 (±3.20) | 0.19 (±0.03) | 308.3 (±390.1) | 51.79 (±16.97) | 15.38 (±8.11) | 105.6 (±106.5) * |
| 4. HDM challenge 15 weeks + isotype control antibody (n = 4) | 5.46 (±3.38) ** | 7.00 (±4.50) * | 0.22 (±0.02) | 395.0 (±270.1) ** | 162.3 (±166.5) ** | 19.57 (±14.81) | 141.7 (±126.3) ** |
| 5. HDM challenge 15 weeks + anti-IL33 antibody (n = 5) | 1.15 (±1.38) | 1.93 (±1.90) | 0.20 (±0.02) | 136.8 (±164.1) | 122.9 (±194.1) | 17.05 (±4.48) * | 16.64 (±6.40) |

TABLE 4-continued

| Experimental group | Mean [IL-4] in lung protein extracts (pg/mg lung protein) (±SD) | Mean [IL-5] in lung protein extracts (pg/mg lung protein) (±SD) | Mean [IL-13] in lung protein extracts (pg/mg lung protein) (±SD) | Mean [IL-6] in lung protein extracts (pg/mg lung protein) (±SD) | Mean [IL-1β] in lung protein extracts (pg/mg lung protein) (±SD) | Mean [TNFα] in lung protein extracts (pg/mg lung protein) (±SD) | Mean [MCP-1] in lung protein extracts (pg/mg lung protein) (±SD) |
|---|---|---|---|---|---|---|---|
| | Cytokine concentration in lung protein extracts | | | | | | |
| 6. HDM challenge 15 weeks + anti-mouse IL-4Rα antibody (n = 5) | 2.88 (±2.43) | 13.13 (±12.81) ** | 0.16 (±0.03) | 18.24 (±12.43) | 26.73 (±20.94) | 7.85 (±4.89) | 11.63 (±8.69) |
| 7. HDM challenge 15 weeks + anti-IL33 + anti-mouse IL-4Rα antibodies (n = 5) | 0.47 (±0.13) | 0.73 (±0.37) | 0.10 (±0.05) †† | 7.46 (±2.52) † | 3.722 (±1.59) | 3.07 (±1.34) | 4.62 (±1.27) †† |

Note:
Statistical significance determined by Kruskal-Wallis One-way ANOVA with Dunn's multiple comparison post-hoc test is indicated
(* = $p < 0.05$,
** = $p < 0.01$, compared to groups 1: IL33 HumIn mice, Saline challenge;
† $p < 0.05$,
†† $p < 0.01$, compared to group 4: IL33 Humin mice, HDM challenge 15 weeks + Isotype control antibody).
ND: Not determined.

Lung Harvest for Gene Expression Analysis.

After exsanguination, the accessory lobe of the right lung from each mouse was removed, placed into tubes containing 400 μL of RNA Later (Ambion, # AM7020) and stored at −20° C. until processing. Tissues were homogenized in TRIzol and chloroform was used for phase separation. The aqueous phase, containing total RNA, was purified using MagMAX™-96 for Microarrays Total RNA Isolation Kit (Ambion by Life Technologies, # AM1839) according to manufacturer's specifications. Genomic DNA was removed using MagMAX™Turbo™DNase Buffer and TURBO DNase from the MagMAX kit listed above. mRNA (up to 2.5 μg) was reverse-transcribed into cDNA using SuperScript® VILO™ Master Mix (Invitrogen by Life Technologies, #11755500). cDNA was diluted to 2 ng/μL and 10 ng cDNA was amplified with the TaqMan® Gene Expression Master Mix (Applied Biosystems by Life Technologies, #4369542) and the relevant probes (Life Technologies; mouse B2m: Mm00437762_m1; mouse Il4: Mm00445259_ml; mouse Il5: Mm00439646_m1; mouse Il13: Mm00434204_m1; mouse Il9: Mm00434305_ml; mouse Il6: Mm00446190_m1; mouse Ccl2: Mm00441242_m1; mouse Ccl11: Mm00441238_m1; mouse Ccl24: Mm00444701_m1; mouse Tnf: Mm00443258_m1; mouse Tgfb1: Mm01178820_m1; mouse Il1rl1: Mm00516117_m1; mouse Il13ra2: Mm00515166_m1; mouse Col15a1: Mm00456584_m1; mouse Col24a1: Mm01323744_m1;) using the ABI 7900HT Sequence Detection System (Applied Biosystems). B2m was used as the internal control genes to normalize any cDNA input differences. The reference group used for normalization of all samples was the average of Group 1 samples ('1×PBS Challenge'). Expression of each gene was normalized to B2m expression within the same sample and expressed relative to its normalized expression in the reference group (mean±SD), as shown in Table 5.

Lung Gene Expression Analysis.

As shown in Table 5, the level of expression of the cytokines, chemokines and collagen genes Il4, Il13, Il6, Ccl2, Tgfb1, Il13ra2 and Col24a1 in the lungs of IL33 Humin mice receiving HDM for 15 weeks, with or without treatment with an isotype control antibody were significantly increased compared to IL33 Humin mice challenged with 1×PBS alone. Similarly, there was a trend towards an increase in expression of the genes Il5, Il9, Ccl11, Ccl24, Tnf, Il1rl1 and Col15a1 in the lungs of IL33 Humin mice receiving HDM for 15 weeks.

In contrast, there was a significant reduction in the expression levels of 116, Ccl2, Ccl11 and Ccl24 in the lungs of IL33 Humin mice treated with a combination of anti-IL33 and anti-mouse IL-4Rα antibodies during the last four weeks of the chronic HDM challenge as compared to IL33 Humin mice administered HDM with an isotype control antibody during this time period. There was a trend towards reduced Il4, Il5, Il13, Il9, Tnf, Tgfb1, Il1rl1, Il13ra2, Col15a1 and Col24a1 expression levels in mice treated with a combination of anti-IL33 and anti-mouse IL-4Rα antibodies during the last four weeks of the chronic HDM challenge as compared to IL33 Humin mice administered HDM with an isotype control antibody during this time period. The effects on gene expression observed with the combination anti-IL33 and anti-mouse IL-4Rα antibodies was greater than treatment with either individual antibodies alone.

TABLE 5

Gene expression (TaqMan) in mouse lungs.

| Experimental group | Mean Relative Il4 expression in lung (±SD) | Mean Relative Il5 expression in lung (±SD) | Mean Relative Il13 expression in lung (±SD) | Mean Relative Il9 expression in lung (±SD) | Mean Relative Il6 expression in lung (±SD) | Mean Relative Ccl2 expression in lung (±SD) | Mean Relative Ccl11 expression in lung (±SD) | Mean Relative Ccl24 expression in lung (±SD) |
|---|---|---|---|---|---|---|---|---|
| 1. 1X PBS challenge (n = 5) | 1.03 (±0.28) | 1.54 (±1.61) | 4.51 (±7.59) | 15.91 (±34.81) | 1.25 (±1.09) | 1.20 (±0.93) | 1.24 (±1.07) | 1.05 (±0.33) |
| 2. HDM challenge 11 weeks (n = 4) | 12.78 (±8.45) * | 7.13 (±3.49) | 114.1 (±68.3) * | 38.66 (±30.04) | 9.12 (±1.65) | 18.86 (±8.40) | 13.36 (±5.05) | 15.44 (±12.02) |
| 3. HDM challenge 15 weeks (n = 4) | 6.27 (±3.39) | 4.20 (±1.51) | 58.05 (±31.61) | 30.63 (±20.54) | 8.92 (±4.55) | 22.61 (±13.37) * | 8.65 (±3.20) | 4.58 (±1.91) |
| 4. HDM challenge 15 weeks + isotype control antibody (n = 4) | 10.98 (±5.46) * | 5.50 (±3.16) | 92.51 (±75.96) * | 19.51 (±10.29) | 13.80 (±6.98) ** | 24.53 (±9.13) ** | 12.14 (±7.82) | 12.41 (±8.73) |
| 5. HDM challenge 15 weeks + anti-IL33 antibody (n = 5) | 2.80 (±3.11) | 1.74 (±1.11) | 12.91 (±12.93) | 0.00 (±0.00) | 3.87 (±3.00) | 5.20 (±2.44) | 6.21 (±3.55) | 1.45 (±2.09) |
| 6. HDM challenge 15 weeks + anti-mouse IL-4Rα antibody (n = 5) | 1.87 (±1.03) | 7.98 (±6.52) | 69.56 (±66.86) * | 63.50 (±92.04) | 2.77 (±1.39) | 2.97 (±1.86) | 1.00 (±0.18) | 0.44 (±0.34) |
| 7. HDM challenge 15 weeks + anti-IL33 + anti-mouse IL-4Rα antibodies (n = 5) | 1.37 (±0.35) | 1.56 (±0.97) | 9.34 (±3.10) | 0.57 (±1.27) | 1.04 (±0.31) †† | 1.08 (±0.24) †† § | 0.72 (±0.28) † | 0.15 (±0.10) †† |

| Experimental group | Mean Relative Tnf expression in lung (±SD) | Mean Relative Tgfb1 expression in lung (±SD) | Mean Relative Il1rl1 expression in lung (±SD) | Mean Relative Il13rα2 expression in lung (±SD) | Mean Relative Col15α1 expression in lung (±SD) | Mean Relative Col24α1 expression in lung (±SD) |
|---|---|---|---|---|---|---|
| 1. 1X PBS challenge (n = 5) | 1.02 (±0.24) | 1.00 (±0.11) | 1.11 (±0.58) | 1.59 (±1.96) | 1.00 (±0.10) | 1.02 (±0.16) |
| 2. HDM challenge 11 weeks (n = 4) | 1.45 (±0.41) | 1.40 (±0.27) | 3.03 (±0.88) * | 48.43 (±34.21) | 2.75 (±0.96) | 24.55 (±7.97) ** |
| 3. HDM challenge 15 weeks (n = 4) | 1.58 (±0.43) | 1.32 (±0.33) | 2.53 (±0.79) * | 32.07 (±13.45) | 3.00 (±1.22) | 17.25 (±5.29) * |
| 4. HDM challenge 15 weeks + isotype control antibody (n = 4) | 1.59 (±0.78) | 1.37 (±0.12) * | 3.45 (±1.48) * | 52.02 (±40.63) | 3.80 (±0.96) * | 23.58 (±6.18) *** |
| 5. HDM challenge 15 weeks + anti-IL33 antibody (n = 5) | 1.38 (±0.27) | 1.22 (±0.24) | 0.99 (±0.47) | 13.54 (±12.25) | 1.64 (±0.30) | 10.58 (±5.42) |
| 6. HDM challenge 15 weeks + anti-mouse IL-4Rα antibody (n = 5) | 1.00 (±0.25) | 1.13 (±0.20) | 3.38 (±1.97) | 1.89 (±0.59) | 1.24 (±0.28) | 7.08 (±4.56) |
| 7. HDM challenge 15 weeks + anti-IL33 + anti-mouse IL-4Rα antibodies (n = 5) | 0.68 (±0.08) § | 1.09 (±0.12) | 1.12 (±0.57) | 1.89 (±0.27) | 0.74 (±0.21) †† § | 1.76 (±0.15) † |

Note:
Statistical significance determined by Kruskal-Wallis One-way ANOVA with Dunn's multiple comparison post-hoc test is indicated
(* = $p < 0.05$,
** = $p < 0.01$,
*** = $p < 0.01$ compared to groups 1: IL33 HumIn mice, Saline challenge;
§ $p < 0.05$,
§§ $p < 0.01$, compared to group 3: IL33 Humin mice, HDM challenge 15 weeks;
† $p < 0.05$,
†† $p < 0.01$, compared to group 4: IL33 Humin mice, HDM challenge 15 weeks + Isotype control antibody).

Lung Harvest for Pulmonary Cell Infiltrate Analysis.

Pulmonary infiltration by immune cells is observed in multiple airway inflammatory diseases, including asthma and COPD. Neutrophilic lung inflammation has been associated with lower lung function and severe tissue remodeling in asthma patients. Eosinophilic lung inflammation is a hallmark of type 2 inflammation usually seen in atopic diseases. In humans, high CD4/CD8 ratios are observed in patients with granulomatous lung diseases and other chronic inflammatory conditions. Flow cytometry was used in the study to determine the level of cellular infiltration in the lungs of HDM-exposed mice.

After exsanguination, the caudal lobe of the right lung from each mouse was removed, chopped into cubes that were approximately 2 to 3 mm in size, and then placed into a tube containing a solution of 20 μg/mL DNAse (Roche, #10104159001) and 0.7 U/mL Liberase TH (Roche, #05401151001) diluted in Hank's Balanced Salt Solution (HBSS) (Gibco, #14025), which was incubated in a 37'C water bath for 20 minutes and vortexed every 5 minutes. The reaction was stopped by adding ethylenediaminetetraacetic acid (EDTA, Gibco, #15575) at a final concentration of 10 mM. Each lung was subsequently dissociated using a gentleMACS dissociator (Miltenyi Biotec, #130-095-937), then filtered through a 70 μm filter and centrifuged. The resulting lung pellet was resuspended in 1 mL of 1× red blood cell lysing buffer (Sigma, # R7757) to remove red blood cells. After incubation for 3 minutes at room temperature, 3 mL of 1×DMEM was added to deactivate the red blood cell lysing buffer. The cell suspensions were then centrifuged, and the resulting cell pellets were resuspended in 5 mL of MACS buffer (autoMACS Running Buffer; Miltenyi Biotec, #130-091-221). The resuspended samples were filtered through a 70 μm filter and $1\times10^6$ cells per well were plated in a 96-well V-bottom plate. Cells were then centrifuged and the pellets were washed in 1×PBS. After a second centrifugation, the cell pellets were resuspended in 100 μL of LIVE/DEAD Fixable Blue Dead Cell Stain (Life Technologies, # L23105) diluted at 1:500 in 1×PBS to determine cell viability and incubated for 20 minutes at room temperature while protected from light. After one wash in 1×PBS, cells were incubated in a solution of MACS buffer containing 10 μg/mL of purified rat anti-mouse CD16/CD32 Fc Block, (Clone: 2.4G2; BD Biosciences, #553142) for 10 minutes at 4'C. The cells were then incubated in the appropriate 2× antibody mixture (described in Table 6) diluted in MACS buffer for 30 minutes at 4'C while protected from light. After antibody incubation, the cells were washed twice in MACS buffer, resuspended in BD CytoFix (BD Biosciences, #554655) and then incubated for 15 minutes at 4° C. while protected from light. The cells were subsequently washed, resuspended in MACS buffer, and then transferred to BD FACS tubes (BD Biosciences, #352235) for analysis of cellular infiltrates by flow cytometry.

CD4 and CD8 T cells were defined as cells that were live, $CD45^+$, $SSC^{Lo}$, $FSC^{Lo}$, $CD3^+$, $CD19^-$, $CD4^+$, $CD8^-$ and live, $CD45^+$, $SSC^{Lo}$, $FSC^{Lo}$, $CD3^+$, $CD19^-$, $CD4^-$, $CD8^+$ respectively. Activated CD4 T cells were defined as cells that were live, $CD45^+$, $SSC^{Lo}$, $FSC^{Lo}$, $CD3^+$, $CD19^-$, $CD4^+$, $CD8^-$, and $CD69^+$. Activated CD8 T cells were defined as cells that were live, $CD45^+$, $SSC^{Lo}$, $FSC^{Lo}$, $CD3^+$, $CD19^-$, $CD4^-$, $CD8^+$, and $CD69^+$. Activated B cells were defined as cells that were live, $CD45^+$, $SSC^{Lo}$, $FSC^{Lo}$, $CD3^-$, $CD19^+$, and $CD69^+$. ST2+CD4+ T cells were defined as cells that were live, $CD45^+$, $SSC^{Lo}$, $FSC^{Lo}$, CD3+, CD19−, ST2+ and $CD4^+$. Eosinophils were defined as live, $CD45^+$, $GR1^-$, $CD11c^{lo}$, $SiglecF^{hi}$. Alveolar macrophages were defined as live, $CD45^+$, $GR1^-$, $CD11c^{Hi}$, $SiglecF^{hi}$. Data for activated cells is expressed as frequency of activated cells ($CD69^+$) within the parent population (CD4, ±SD). Data for ST2+ CD4+ T cells is expressed as frequency of T cells (defined as cells that were live, $CD45^+$, $SSC^{Lo}$, $FSC^{Lo}$, CD3+ and CD19−). Data for Eosinophils and Alveolar macrophages are expressed as frequency of live cells. CD4/CD8 T cells ratio is calculated as the ratio of the frequency of CD4 T to the frequency of CD8 T cells within the live population. All data are shown in Table 7.

TABLE 6

Antibodies Used for Flow Cytometry Analysis

| Antibody | Fluorochrome | Manufacturer | Catalogue Number | Final dilution |
|---|---|---|---|---|
| CD45.2 | PerCP-Cy5.5 | eBioscience | 45-0454 | 1/800 |
| Siglec-F | BV 421 | BD | 562681 | 1/200 |
| F4/80 | APC | eBioscience | 17-4801-82 | 1/200 |
| Ly6G | BUV395 | BD | 563978 | 1/200 |
| Ly6C | PE-Cy7 | BD | 560593 | 1/100 |
| CD11c | PE | eBioscience | 12-0114-82 | 1/200 |
| CD11b | FITC | eBioscience | 53-0112-82 | 1/200 |
| CD19 | BV650 | BD | 562701 | 1/400 |
| CD3 | PE-Cy7 | BD | 552774 | 1/200 |
| CD4 | BV421 | BioLegend | 100438 | 1/200 |
| CD8 | BUV 395 | BD | 563786 | 1/400 |
| NKp46 (CD335) | FITC | eBioscience | 11-3351 | 1/800 |
| CD69 | PE | eBioscience | 12-0691 | 1/200 |
| CD25 | BV510 | BioLegend | 102042 | 1/200 |
| ST2 | APC | BioLegend | 145306 | 1/200 |

Pulmonary Cell Infiltrate Analysis.

As shown in Table 7, the frequency of eosinophils, activated B cells, activated CD8 cells, ST2+Cd4+ T cells and CD4/CD8 T cells ratio in the lungs of IL33 Humin mice receiving HDM for 15 weeks, with or without treatment with an isotype control antibody were significantly higher than in IL33 Humin mice challenged with 1×PBS alone. Similarly, there was a trend towards an increased frequency of activated CD4 T cells in the lungs of IL33 Humin mice receiving HDM for 15 weeks. There was a trend towards a decreased frequency of alveolar macrophages detected by flow cytometry in the lungs of IL33 Humin mice receiving HDM for 15 weeks, in the absence or presence of an isotype control antibody treatment. The frequency of alveolar macrophages was significantly increased in the lungs of IL33 Humin mice treated with a combination of anti-IL33 and anti-mouse IL-4Rα antibodies during the last four weeks of the chronic HDM challenge as compared to IL33 Humin mice administered HDM with an isotype control antibody during this time period. Similarly, there was a trend towards reduced frequency of eosinophils, activated CD4 and CD8 T cells, activated B cells, ST2+CD4+ T cells as well as CD4/CD8 T cells ratio in the lungs of mice treated with a combination of anti-IL33 and anti-mouse IL-4Rα antibodies during the last four weeks of the chronic HDM challenge as compared to IL33 Humin mice administered HDM with an isotype control antibody during this time period. The effects on frequency of eosinophils, alveolar macrophages, activated CD8 T cells, ST2+CD4+ T cells and CD4/CD8 ratio in the lung observed for the combination anti-IL33 and anti-mouse IL-4Rα antibodies shows a trend towards greater efficacy than treatment with either individual antibodies alone.

TABLE 7

Frequency of pulmonary cell infiltrate as determined by flow cytometry

| Experimental group | Mean Frequency of Eosinophils in the live population (±SD) | Mean Frequency of Alveolar Macrophages in the live population (±SD) | Mean CD4/CD8 T cells ratio (±SD) | Mean Frequency of Activated cells in CD4 T cells population (±SD) | Mean Frequency of Activated cells in CD8 T cells population (±SD) | Mean Frequency of Activated cells in B cells population (±SD) | Mean Frequency of ST2+ CD4+ cells in T cells population (±SD) |
|---|---|---|---|---|---|---|---|
| 1. 1X PBS challenge (n = 5) | 1.45 (±0.92) | 5.05 (±1.64) | 3.00 (±1.48) | 13.12 (±9.89) | 3.26 (±1.64) | 0.39 (±1.17) | 3.25 (±4.15) |
| 2. HDM challenge 11 weeks (n = 4) | 17.08 (±3.94) * | 2.34 (±0.93) | 6.42 (±2.71) | 49.95 (±8.76) | 9.58 (±7.44) | 4.67 (±1.47) ** | 32.60 (±12.23) |
| 3. HDM challenge 15 weeks (n = 4) | 15.40 (±3.99) * | 4.92 (±1.55) | 6.95 (±0.71) ** | 58.53 (±5.76) | 15.68 (±3.03) * | 3.70 (±1.44) * | 37.33 (±8.98) * |
| 4. HDM challenge 15 weeks + isotype control antibody (n = 4) | 15.00 (±3.35) * | 2.33 (±1.60) | 7.49 (±1.28) * | 57.75 (±7.64) | 14.59 (±3.82) | 3.90 (±1.48) * | 37.96 (±16.71) * |
| 5. HDM challenge 15 weeks + anti-IL33 antibody (n = 5) | 8.51 (±7.52) | 7.44 (±4.18) | 4.03 (±1.28) | 48.22 (±5.66) | 13.86 (±5.21) | 1.72 (±0.72) | 19.24 (±5.72) |
| 6. HDM challenge 15 weeks + anti-mouse IL-4Rα antibody (n = 5) | 12.30 (±7.83) | 9.93 (±5.18) | 5.56 (±2.22) | 53.42 (±6.52) | 13.11 (±6.26) | 2.14 (±1.23) | 35.01 (±9.83) * |
| 7. HDM challenge 15 weeks + anti-IL33 + anti-mouse IL-4Rα antibodies (n = 5) | 3.78 (±1.60) | 14.64 (±3.86) † | 2.96 (±0.93) | 42.52 (±9.79) | 7.90 (±1.30) | 1.74 (±0.91) | 11.78 (±3.73) |

Note:
Statistical significance determined by Kruskal-Wallis One-way ANOVA with Dunn's multiple comparison post-hoc test is indicated
(* = $p < 0.05$,
** = $p < 0.01$, compared to groups 1: IL33 HumIn mice, Saline challenge;
† $p < 0.05$, compared to group 4: IL33 Humin mice, HDM challenge 15 weeks + Isotype control antibody).

Lung Harvest for Quantification of Histopathology.

The inflammatory pattern observed in this model is accompanied by widespread and severe structural changes in HDM-exposed lungs, with evidence of goblet cell metaplasia, increases in sub-epithelial collagen deposition and significant pulmonary consolidation. These pathologies are known features of human inflammatory respiratory diseases that contribute to decline of lung function and airway hyperreactivity.

After exsanguination, the left lungs were removed and placed into plates containing a 3 mL solution of 4% (w/v) paraformaldehyde (Boston Bioproducts, # BM-155) in 1× phosphate buffered saline and stored at room temperature for 3 days. Lung samples were then blotted dry and transferred to tubes containing 70% ethanol for histological analysis. The samples were sent to Histoserv, Inc (Germantown, Md.) for paraffin embedding, sectioning and periodic acid Schiff (PAS) or Hematoxylin and Eosin (H&E) staining.

Quantification of Goblet Cell Metaplasia.

Goblet cell metaplasia and mucus hyper-secretion are hallmarks of many pulmonary diseases including asthma, chronic obstructive pulmonary disease, and cystic fibrosis. Excessive mucus production leads to airway obstruction and affects several important outcomes such as lung function, health-related quality of life, exacerbations, hospitalizations, and mortality in humans. PAS-positive goblet cells and total epithelial cells were counted in a millimeter length of the primary bronchus. Goblet cell metaplasia is expressed as the frequency of PAS-positive cells in a millimeter of bronchial epithelium (%, ±SD) as shown in Table 8.

Quantification of Lung Consolidation.

Lung consolidation includes the accumulation of solid or liquid material in the alveolar space. Lung consolidation is a compound endpoint likely reflecting the combination of cellular infiltrate, hyperplasia, and mucus production, used here as a measurement of gross pathology. The fraction of lung area occupied by the crystal bodies was quantified on Movat pentachrome stained paraffin-embedded lung sections using Image) software (NIH, Bethesda, Md.). Using the particle analysis function, total lung area in the section, as well as consolidated area in the section were measured. The fraction of consolidated lung area is given by the ratio of both measurements, as shown in Table 8.

Quantification of Sub-Epithelial Fibrosis.

Sub-epithelial fibrosis includes an excess of interstitial collagen deposition beneath the pulmonary epithelium. Increased sub-epithelial fibrosis has been reported to be specifically associated with asthma in humans. In the model, sub-epithelial fibrosis was measured on Masson's trichrome stained paraffin-embedded lung sections using HaLo software (Indica Labs, NM). Using the Layer thickness tool, the thickness of the collagen layer beneath the bronchial epithelium was recorded multiple times, with about 30 μm intervals, across a millimeter of the primary bronchus. Sub-epithelial fibrosis is expressed as the mean thickness of the collagen layer beneath the epithelium (μm, ±SD) as shown in Table 8.

Analysis of Lung Histopathology.

As shown in table 9, there was a trend towards an increase in goblet cell metaplasia in the lungs of IL33 Humin mice receiving HDM for 15 weeks, with or without treatment with an isotype control antibody compared to IL33 Humin mice challenged with 1×PBS alone. Similarly, there was a significant increase in lung consolidation, as well as in sub-epithelial collagen thickness, in IL33 Humin mice receiving HDM for 15 weeks.

In contrast, there was trend towards a reduction in goblet cell metaplasia and sub-epithelial collagen thickness, and a significant reduction in lung consolidation in IL33 Humin mice treated with a combination of anti-IL33 and anti-mouse IL-4Rα antibodies during the last four weeks of the chronic HDM challenge as compared to IL33 Humin mice administered HDM with an isotype control antibody during this time period. The effects on goblet cell metaplasia, lung consolidation and sub-epithelial collagen thickness observed for the combination anti-IL33 and anti-mouse IL-4Rα antibodies showed a trend towards greater efficacy than treatment with either individual antibodies alone.

TABLE 8

Quantification of histopathology in mouse lungs

| Experimental group | Mean Goblet cell metaplasia (% PAS-positive cells) (±SD) | Mean lung consolidation (% ±SD) | Mean sub-epithelial collagen thickness (μm) (±SD) |
|---|---|---|---|
| 1. 1X PBS challenge (n = 5) | 32.94 (±43.61) | 6.97 (±3.72) | 25.90 (±4.00) |
| 2. HDM challenge 11 weeks (n = 4) | 59.98 (±39.01) | 70.70 (±12.94) | 81.76 (±25.37) * |
| 3. HDM challenge 15 weeks (n = 4) | 92.15 (±10.16) | 83.21 (±3.65) ** | 82.12 (±23.04) * |
| 4. HDM challenge 15 weeks + isotype control antibody (n = 4) | 81.60 (±17.56) | 84.16 (±5.85) ** | 63.11 (±11.87) |
| 5. HDM challenge 15 weeks + anti-IL33 antibody (n = 5) | 39.22 (±18.93) | 58.82 (±18.26) | 70.99 (±23.85) |
| 6. HDM challenge 15 weeks + anti-mouse IL-4Rα antibody (n = 5) | 79.82 (±25.02) | 57.79 (±18.72) | 57.62 (±15.34) |
| 7. HDM challenge 15 weeks + anti-IL33 + anti-mouse IL-4Rα antibodies (n = 5) | 19.69 (±8.80) | 35.01 (±20.68) | 48.19 (±18.58) |

Note:
Statistical significance determined by Kruskal-Wallis One-way ANOVA with Dunn's multiple comparison post-hoc test is indicated
(** = $p < 0.01$, compared to groups 1: IL33 HumIn mice, Saline challenge).

Serum Collection for IgE and HDM-Specific IgG1 Levels Measurement.

To determine the total IgE concentration in the serum samples for each mouse, a sandwich ELISA OPTEIA kit (BD Biosciences, #555248) was used according to the manufacturer's instructions. Serum samples were diluted and incubated with anti-IgE capture antibody coated on 96-well plates. Total IgE was detected by biotinylated anti-mouse IgE secondary antibody. Purified horseradish peroxidase (HRP)-labeled mouse IgE was used as a standard. The chromagen 3,3$^1$,5,5'-tetramethylbenzidine (TMB) (BD OPTEIA substrate reagent set, BD, #555214) was used to detect HRP activity. A stop solution of 1 M sulfuric acid was then added, and absorbance at 450 nm was measured on a Molecular Devices SpectraMax M5 plate reader. Data analysis was performed using Prism™ software. The mean amounts of circulating IgE levels in serum for each experimental group are expressed as ng/mL (±SD) as shown in Table 9.

To determine the HDM specific IgG1 levels in the serum samples from each mouse, an ELISA was utilized. HDM (Greer, # XPB70D3A2.5) coated plates were incubated with serially diluted mouse serum samples, followed by incubation with a rat anti-mouse IgG1-HRP conjugated antibody (BD Biosciences, #559626). All samples were developed with a TMB solution and analyzed as described above. Relative levels of circulating IgG1 in serum were represented as titer units (titer units were calculated by multiplying the measured OD by a dilution factor required to achieve OD450 that was greater than two times background). The mean circulating HDM-specific IgG1 levels in serum for each experimental group are expressed as titer×$10^6$ (±SD) as shown in Table 9.

Analysis of the Circulation Levels of IgE and HDM-Specific IgG1.

As shown in Table 9, there was a significant increase in circulating levels of IgE in the serum of IL33 Humin mice receiving HDM for 15 weeks, with or without treatment with an isotype control antibody in IL33 Humin mice challenged with 1×PBS alone. Similarly, there was a trend towards an increased level of circulating HDM-specific IgG1 in the serum of IL33 Humin mice receiving HDM for 15 weeks. In contrast, there was a significant decrease in circulating levels of IgE and a trend towards a decrease in circulating levels of HDM-specific IgG1 in the serum of IL33 Humin mice treated with a combination of anti-IL33 and anti-mouse IL-4Rα antibodies during the last four weeks of the chronic HDM challenge as compared to IL33 Humin mice administered HDM with an isotype control antibody.

TABLE 9

Circulating levels of IgE and HDM-specific IgG1 in mouse serum.

| Experimental group | Mean circulating IgE levels (μg/mL) (±SD) | Mean circulating HDM-specific IgG1 levels (Titer × $10^6$) (±SD) |
|---|---|---|
| 1. 1X PBS challenge (n = 5) | 2.16 (±2.02) | ND |
| 2. HDM challenge 11 weeks (n = 4) | 50.16 (±8.35) | 1.18 (±0.15) |
| 3. HDM challenge 15 weeks (n = 4) | 131.38 (±106.84) * | 1.88 (±0.81) |
| 4. HDM challenge 15 weeks + isotype control antibody (n = 4) | 193.07 (±78.96) *** | 1.62 (±0.62) |

TABLE 9-continued

Circulating levels of IgE and HDM-specific IgG1 in mouse serum.

| Experimental group | Mean circulating IgE levels (μg/mL) (±SD) | Mean circulating HDM-specific IgG1 levels (Titer × $10^6$) (±SD) |
|---|---|---|
| 5. HDM challenge 15 weeks + anti-IL33 antibody (n = 5) | 45.74 (±45.74) | 1.76 (±0.98) |
| 6. HDM challenge 15 weeks + anti-mouse IL-4Rα antibody (n = 5) | 11.12 (±8.65) | 0.99 (±0.56) |
| 7. HDM challenge 15 weeks + anti-IL33 + anti-mouse IL-4Rα antibodies (n = 5) | 6.45 (±5.79) † | 0.75 (±0.30) |

Note:

Statistical significance determined by Kruskal-Wallis One-way ANOVA with Dunn's multiple comparison post-hoc test is indicated (* = $p < 0.05$,

**= $p < 0.01$,

*** = $p < 0.001$, compared to groups 1: IL33 HumIn mice, Saline challenge;

† $p < 0.05$, compared to group 4: IL33 Humin mice, HDM challenge 15 weeks + Isotype control antibody).

ND: Not determined.

A combination of H4H9675P and anti-mIL-4Rα treatment initiated in the context of severe, mixed inflammation improves all inflammatory parameters measured, reducing most to baseline levels. Additionally, additive effects are observed on some of the most pernicious endpoints, including composite lung gross pathology, goblet cell metaplasia, lung cellular infiltration, and cytokine levels. Therefore, blocking both pathways simultaneously has the potential to impact multiple inflammatory mediators in the context of severe mixed inflammation and tissue pathology, and normalize multiple parameters to baseline.

Example 2

Genetic Variants in IL33 and its Receptor Associate with Both Eosinophilic Asthma and COPD In this Example, the relationship between previously identified asthma risk variants at IL33 and IL1RL1 with risk of asthma, COPD, and ACOS was examined in the largest combined collection of such cases yet assembled, in which genetic data is linked to electronic health records. The importance of these variants to eosinophilic subtypes of asthma, COPD, and ACOS, as well as to related upper airway diseases such as nasal polyps was examined. In addition, the association between predicted loss-of-function variants (pLOF) in IL1RL1 and IL33 with these diseases was evaluated.

Human Genetics Study Oversight.

The human genetics studies were conducted as part of the DiscovEHR study of the Regeneron Genetics Center (RGC) and the Geisinger Health System (GHS).

DiscovEHR Participants and Disease Definitions.

At the time of this study, the DiscovEHR study comprised a total of 92,323 adult individuals enrolled in the MyCode® Community Health Initiative of the GHS. For this study 86,004 and 83,339 individuals of European ancestry had phenotype, and exome sequencing and genotype data, respectively for analysis. Participants were recruited from outpatient primary care and specialty clinics. Eosinophil counts and disease diagnosis codes (the International Classification of Diseases, Ninth Revision [ICD-9]) were extracted from EHRs, which covered a median of 14 years of clinical care. Median EHR-documented eosinophil count measurements were derived from complete blood counts following removal of likely spurious values that were >3 standard deviations from the intra-individual median value. Case status was assigned on the basis of ICD-9 codes if at least one of the following criteria were met: (1) a problem-list entry of the diagnosis code; or (2) an encounter diagnosis code entered for 2 separate clinical encounters on separate calendar days. Individuals were assigned one or more of the three case classifications (asthma, COPD and ACOS) based on ICD-9 diagnosis codes.

Control patients for all binary trait analyses were defined as individuals without a single ICD-9 diagnosis code of asthma or COPD.

Sequencing and Genotyping.

Sample preparation and whole exome sequencing were performed. In brief, exome capture was performed using either NimbleGen probes (Roche, SeqCap VCRome) or Integrated DNA Technologies probes (IDT, xGEN Exome Research panel) with additional content according the respective manufacturer's recommended protocol. Captured DNA was PCR amplified and quantified by qRT-PCR (Kapa Biosystems). Multiplexed samples were sequenced using 75 bp paired-end sequencing on Illumina v4 HiSeq 2500 or HiSeq X sequencers to a coverage depth sufficient to provide greater than 20× haploid read depth of over 85% of targeted bases in 96% of samples (approximately 80× mean haploid read depth of targeted bases). Raw sequence data from each Illumina HiSeq 2500 run were uploaded to the DNAnexus platform for sequence read alignment and variant identification. Raw sequence data were converted from BCL files to sample-specific FASTQ-files, which were aligned to the human reference build GRCh38 with BWA-mem. Single nucleotide variants (SNV) and insertion/deletion (indel) sequence variants were identified using the Genome Analysis Toolkit. Samples with genotype rate less than 10% were excluded. For final analyses, exome data was available for 59,082 and 29,504 individuals of European Ancestry captured using VCRome xGEN probe sets, respectively.

Aliquots of DNA were genotyped using the Human OmniExpress Exome Beadchip or the Global Screening Array (Illumina Corp.). For final analyses, Chip data was available for 56,239 and 28,500 individuals of European ancestry assayed on the Omni and GSA BeadChips respectively Study Design and Statistical Analysis.

OMNI and GSA Chip data was used to evaluate two previously identified asthma risk variants (IL33 (rs1342326) and IL1RL1 (rs1420101)) for association with obstructive lung diseases, other airway diseases, and circulating eosinophil counts. These variants were tested for association with disease under an additive model using logistic regression in PLINK or R, including age, age$^2$, sex, smoking status, and the first four principal components of ancestry as covariates. Median EHR-documented eosinophil counts were log-transformed and tested for association with genotypes under an additive genetic model using linear (PLINK, R) models controlling for the same covariates as above. All p-values correspond to additive genetic models. Resulting summary statistics from analyses on both platforms were combined by meta-analysis.

Under the same statistical framework, exome data was used to identify associations between pLOF variants aggregated within IL1RL1 or IL33 and obstructive lung disease outcomes and eosinophil counts. At each gene, individuals were coded 0 if they did not carry any pLOF, and 1 if they were heterozygous carriers of at least one pLOF; No homozygous pLOF carriers for either IL1RL1 or IL33 were observed in this study. Resulting summary statistics from analyses on both platforms were combined by meta-analysis.

A genetic risk score, reflecting the sum of risk alleles for two independent variants (IL33 (rs1342326) and IL1RL1 (rs1420101)), was also used as a predictor of obstructive lung disease outcomes and eosinophil counts using logistic and linear regression models and the same covariates described above. Individuals missing genotype data for either or both variants were excluded. The effects of carrying one, two, three, or four risk alleles were determined separately relative to individuals carrying no risk allele at either variant. Trends between increasing score and increasing eosinophil counts or disease risk were tested using the linear regression and the Cochran-Armitage test, respectively.

All statistical analyses were performed with the use of PLINK software (v1.90p) or R version 3.2.1.

Confirmation of Previously Identified Asthma Risk Variants in IL33 and IL1RL1 with DiscovEHR Eosinophil Counts and EHR-Defined Asthma.

Clinical characteristics of MyCode® participants in the DiscovEHR study are described in FIG. 8. Among 86,004 patients of European ancestry exome sequenced in this study, 13267 (15.4%) patients were diagnosed with asthma, 9783 (11.4%) patients with COPD, and 2993 (3.4%) patients with both asthma and COPD (referred to here as asthma-COPD overlap syndrome, or ACOS). Among 83,339 patients of European ancestry with available Chip data for this study, 12832 (15.4%) patients were diagnosed with asthma, 9536 (11.4%) patients with COPD, and 2909 (3.5%) patients with ACOS.

Figure 3:
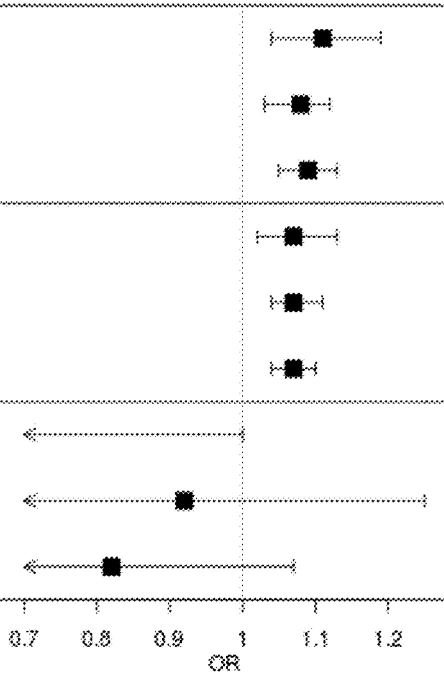
FIG. 3 (Panels A, B, and C) shows rs1420101 (IL1RL1, also known as ST2), s1342326 (IL33) and rs146597587 (IL33-pLoF) associations with (Panel A) Asthma, (Panel B) High Eosinophil Asthma Subset and (Panel C) Low Eosinophil Asthma Subset. Odds ratios for disease were calculated using logistic regression, with adjustment for age, $age^2$, sex, smoking status and principal components of ancestry.
Figure 3:
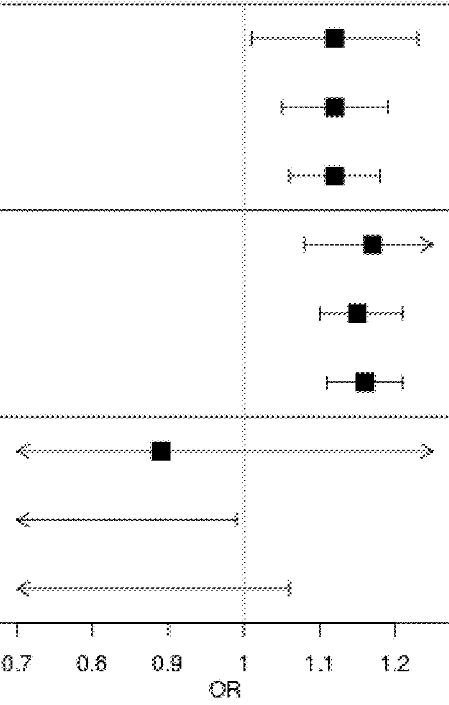
Figure 3:
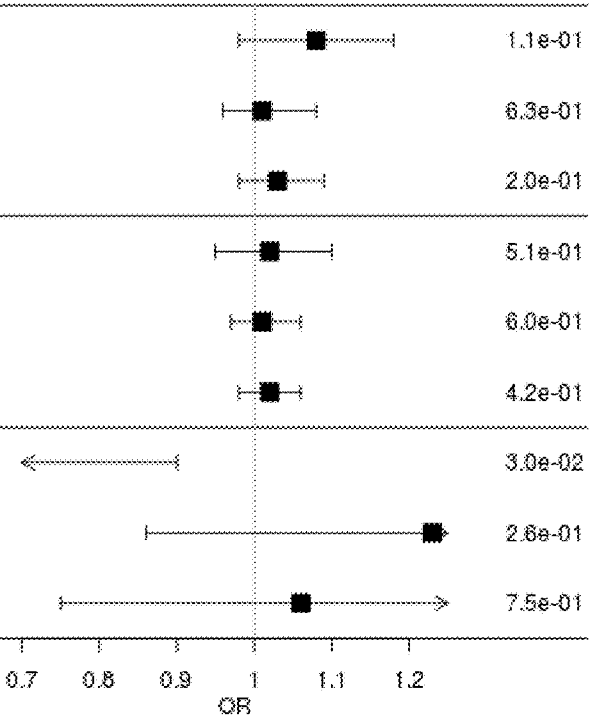

The first large GWAS of asthma identified an intronic IL1RL1 variant (rs1420101) that was associated with both asthma and circulating eosinophil counts, and a subsequent GWAS identified an upstream IL33 variant (rs1342326) that was associated with asthma. In this study, association of rs1420101 (IL1RL1) and rs1342326 (IL33) with asthma (meta allelic odds ratio ($OR_{allelic}$) was confirmed (95% confidence interval) 1.07 (1.04-1.11), $P=8.2\times10^{-7}$ and Meta-$OR_{allelic}$ 1.09 (1.05-1.16), $P=6.0\times10^{-6}$, respectively) (FIG. 3).

Additionally, both variants were associated with lifetime median circulating eosinophil counts (n=66,776 individuals) (Meta-beta=0.0066 (0.0054-0.0079) eos/ml, $P=2.0\times10^{-23}$ and Meta-beta=0.0061 (0.0045-0.0078) eos/ml, $P=2.0\times10^{-13}$, respectively IL33 and IL1RL1 Associations with Asthma are Specific to Eosinophilic Subset.

Eosinophilic asthma is recognized as an important subset of asthma, and seems to be associated with increased asthma severity and steroid refractoriness, as well as differential responsiveness to biologic therapies. Having confirmed the previously described associations between the IL33 and IL1RL1 variants and eosinophil counts as well as asthma, independently assessed as distinct phenotypes, the study next assessed whether these risks are connected through a specific association with the eosinophilic subset of asthma, and therefore associations in asthma patient subgroups stratified by high (>200 eos/μL) and low (≤200 eos/μL) median lifetime eosinophil counts were assessed (FIG. 3). Both the IL33 (rs1342326) and IL1RL1 (rs1420101) variants were significantly associated only with the eosinophilic asthma subset (for IL33, the allelic meta odds ratio was 1.12 (1.06-1.18) in the high eosinophil group vs. 1.04 (0.98-1.09) in the low eosinophil group; for IL1RL1, the allelic odds ratio was 1.07 (1.04-1.1) in the high eosinophil group vs. 1.02 (0.98-1.06) in the low eosinophil group) (FIG. 3).

Novel Associations Between Asthma Risk Variants in IL33 and IL1RL1 and Increased Risk of COPD and ACOS, Specifically in Eosinophilic Subsets.

Figure 4:
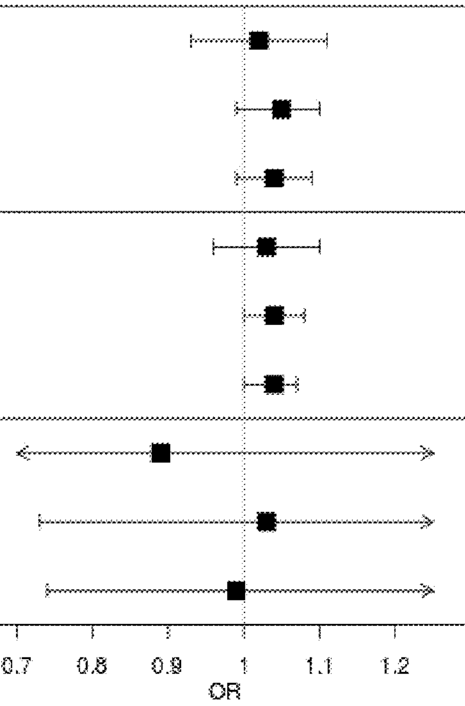
FIG. 4 (Panels A, B, and C) shows rs1420101 (IL1RL1, also known as ST2), s1342326 (IL33) and rs146597587 (IL33-pLoF) associations with (Panel A) COPD, (Panel B) High Eosinophil COPD Subset and (Panel C) Low Eosinophil COPD Subset. Odds ratios for disease were calculated using logistic regression, with adjustment for age, $age^2$, sex, smoking status and principal components of ancestry.
Figure 4:
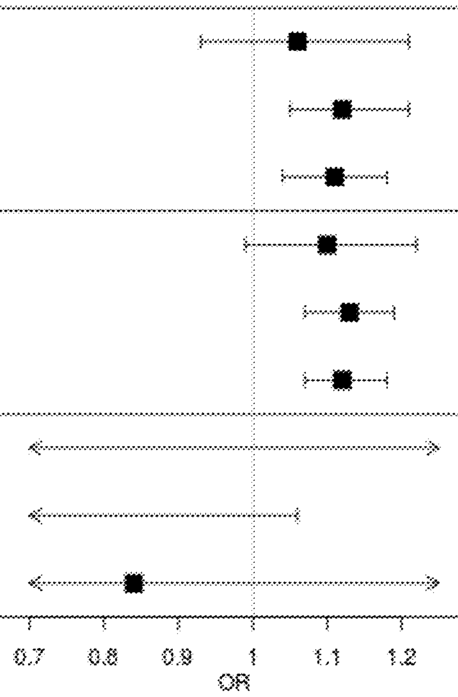
Figure 4:
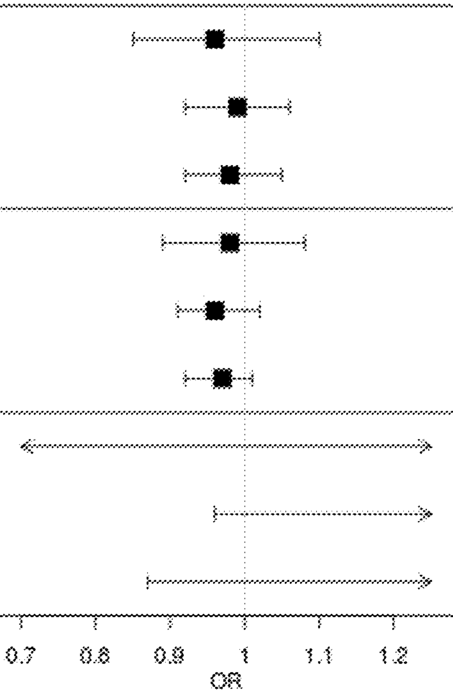
Figure 5:
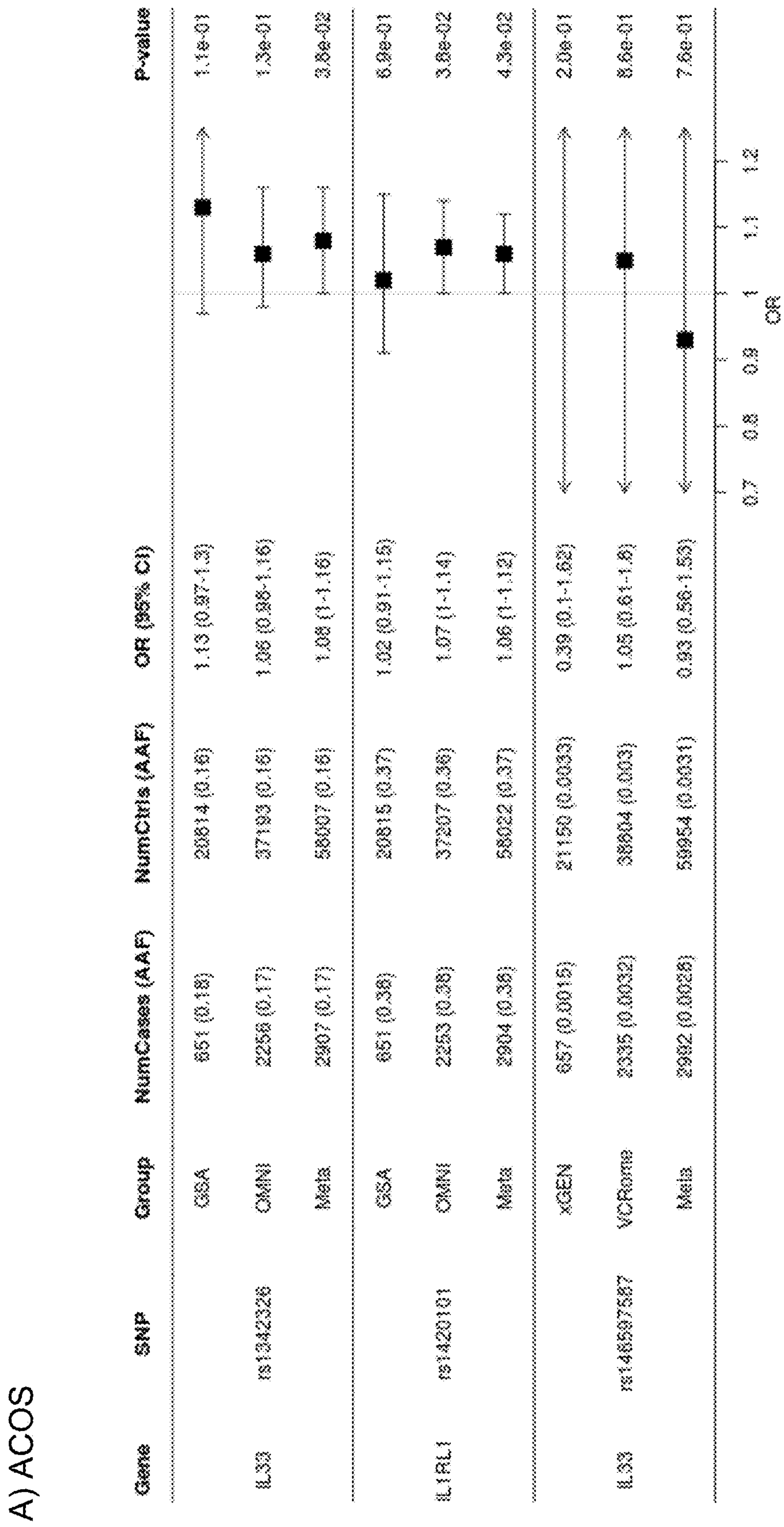
FIG. 5 (Panels A, B, and C) shows rs1420101 (IL1RL1, also known as ST2), s1342326 (IL33) and rs146597587 (IL33-pLoF) associations with (Panel A) ACOS, (Panel B) High Eosinophil ACOS Subset and (Panel C) Low Eosinophil ACOS Subset. Odds ratios for disease were calculated using logistic regression, with adjustment for age, $age^2$, sex, smoking status and principal components of ancestry.
Figure 5:
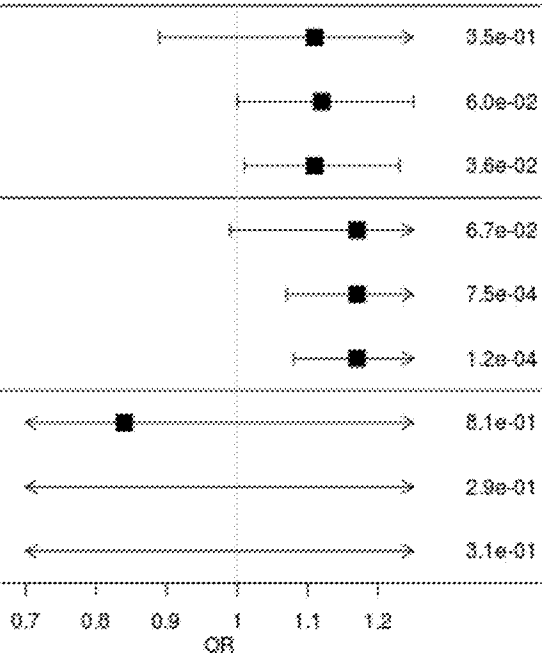
Figure 5:
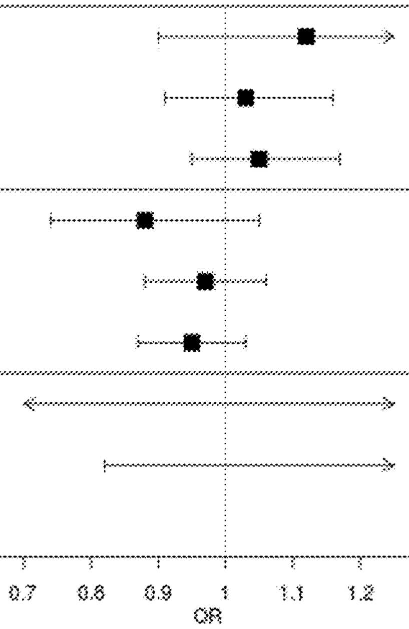

In addition to the above associations with eosinophilic asthma, it was further discovered that the IL33 (rs1342326) and IL1RL1 (rs1420101) variants are suggestively or marginally significantly associated with COPD (FIG. 4, for IL33, Meta $OR_{allelic}$=1.04 (0.99-1.09), $P=8.9\times10^{-2}$, and for IL1RL1, Meta-$OR_{allelic}$=1.04 (1-1.07), $P=3.9\times10^{-2}$) and ACOS (FIG. 5 for IL33, Meta $OR_{allelic}$ 1.08 (1.0-1.16), $P=3.8\times10^{-2}$, and for IL1RL1, 1.06 (1.0-1.12), $P=4.8\times10^{-2}$).

As with asthma, eosinophilic subsets of COPD and ACOS are associated with more severe disease. To determine whether the IL33 and IL1RL1 associations with COPD and ACOS were also specific to eosinophilic subtypes, as we had seen in asthma, associations between IL33 (rs1342326) and IL1RL1 (rs1420101) in COPD and ACOS subgroups stratified by high (>200 eos/μL) and low (5200 eos/μL) median lifetime eosinophil count were assessed (FIGS. 4 and 5). Both variants were suggestively associated with COPD and ACOS only in the disease subgroups characterized by high circulating eosinophils.

Higher Burden of Risk-Increasing Alleles in the IL33 Signaling Pathway Leads to Larger Increases in Asthma, COPD and ACOS Risk.

Figure 2:
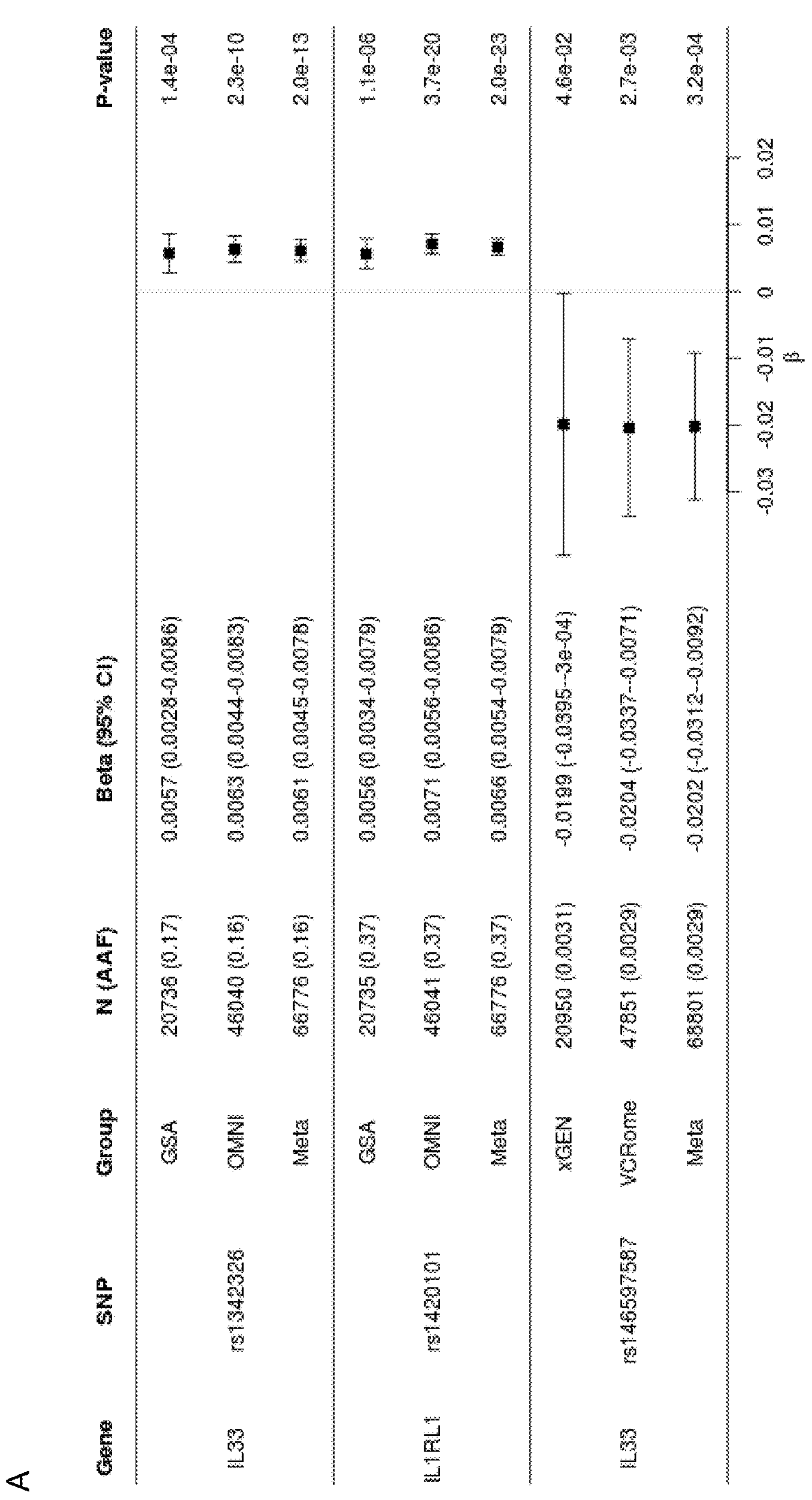
FIG. 2 (Panels A, B, C, and D) shows rs1420101 (IL1RL1, also known as ST2), s1342326 (IL33) and rs146597587 (IL33-pLoF) associations with (Panel A) eosinophil counts (Panel B) $log_{10}$ eosinophil counts. The associations between the total burden of rs1420101 and rs1342326 risk alleles, and (Panel C) eosinophil counts (Panel D) $log_{10}$ eosinophil counts is also shown. Effect sizes and P-values for eosinophil counts and $log_{10}$ eosinophil counts, were calculated using linear regression, with adjustment for age, $age^2$, sex, smoking status and principal components of ancestry. P-values and effect sizes/odds ratios were estimated for individual scores; in each case the comparison was to individuals with zero risk alleles. Additionally, overall allelic effects p-values are shown.
Figure 2:
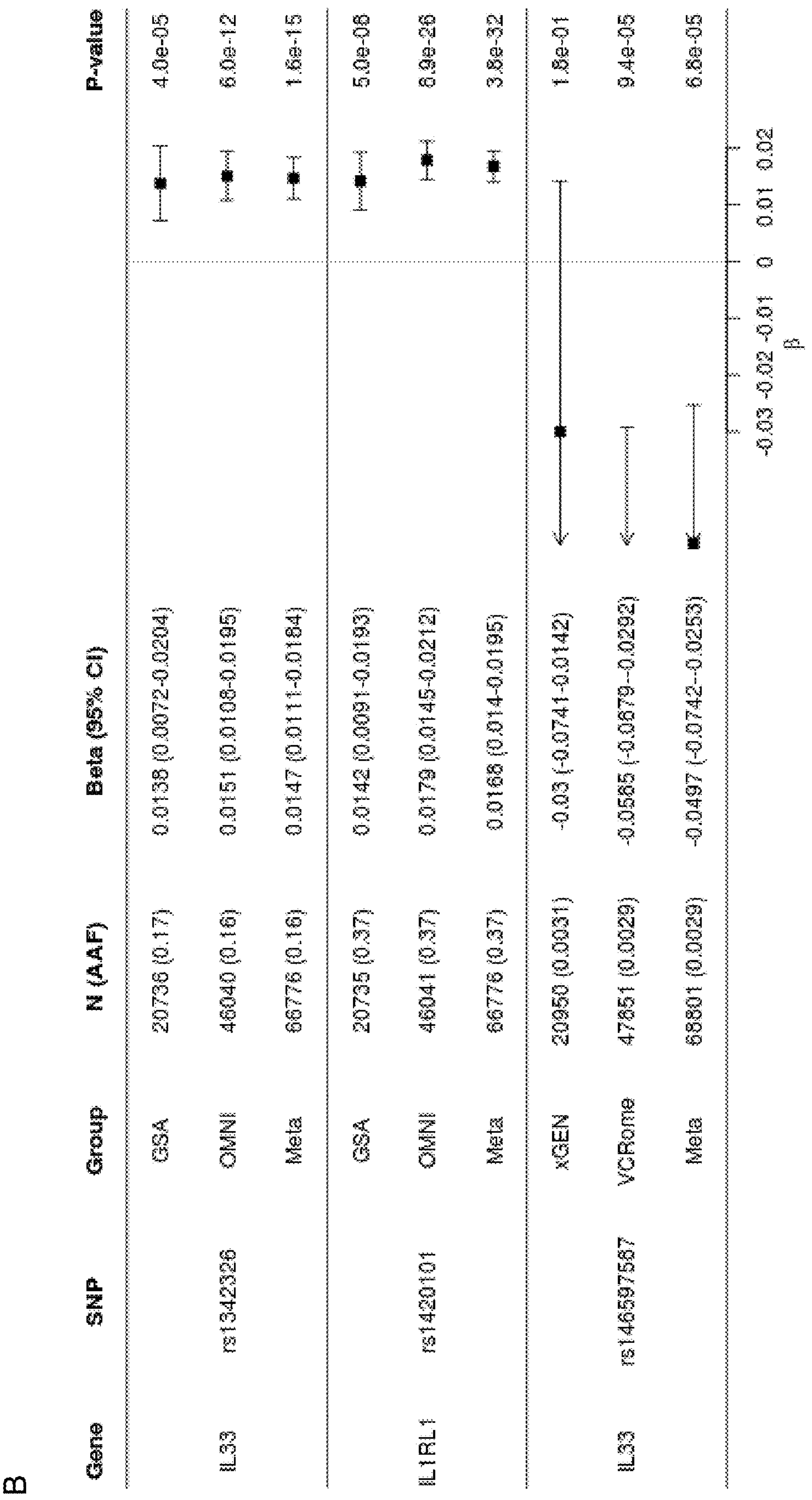
Figure 2:
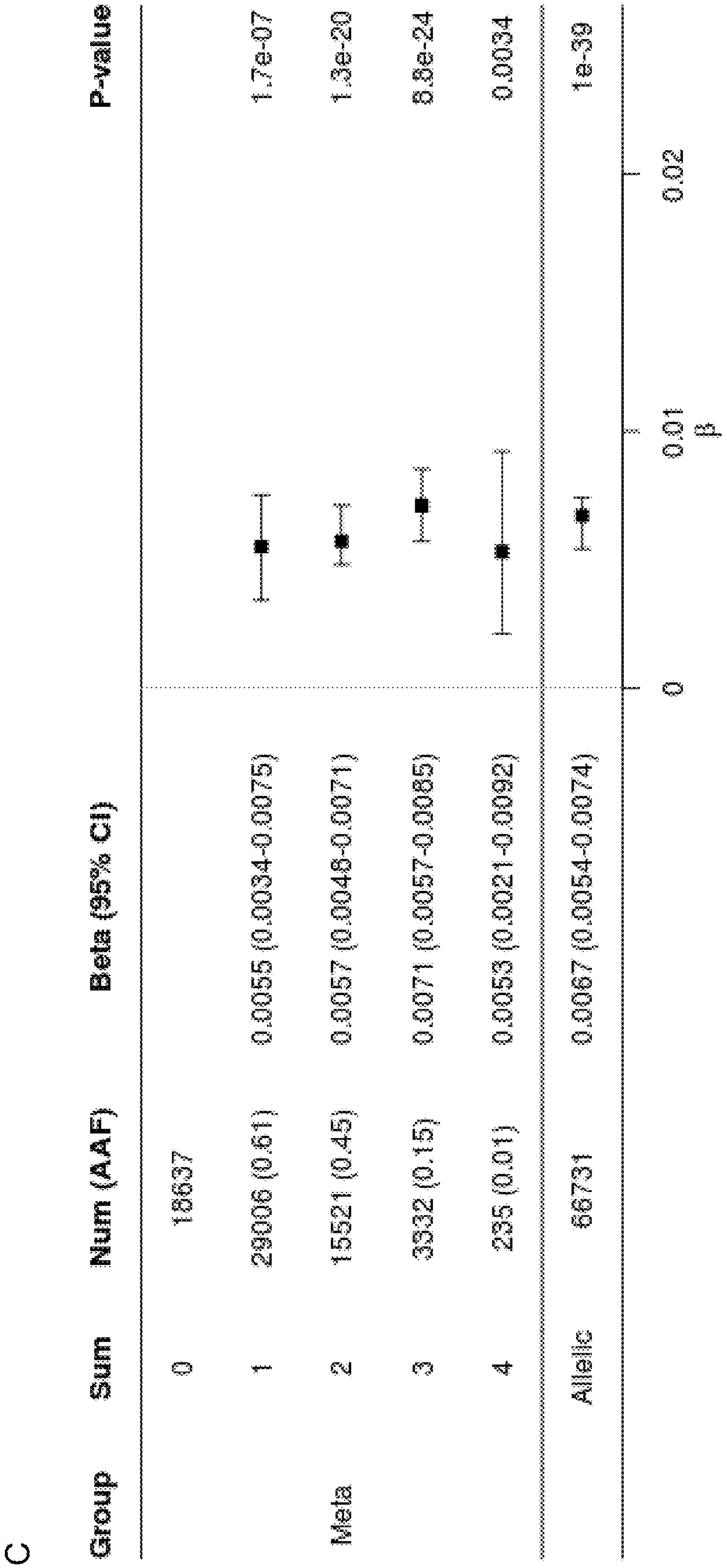
Figure 2:
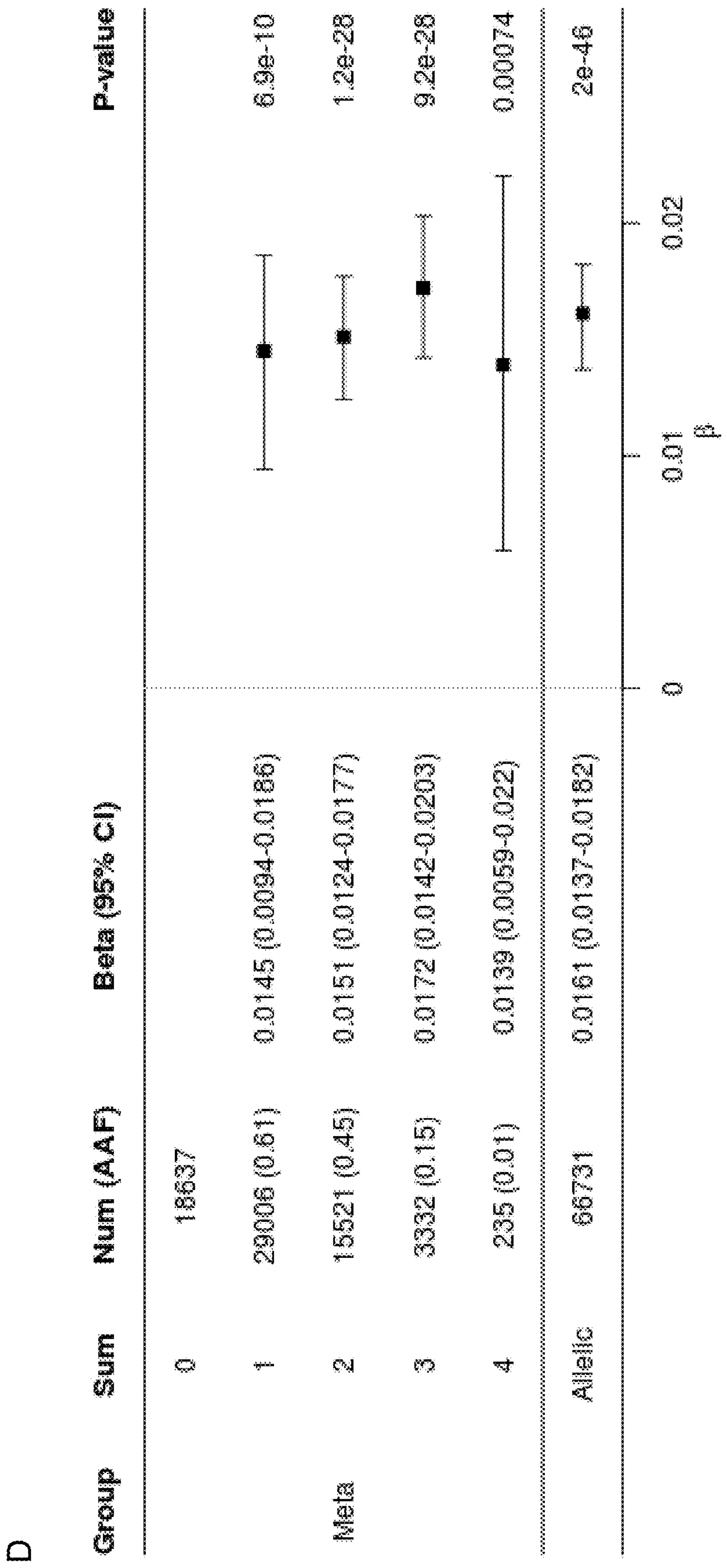
Figure 6:
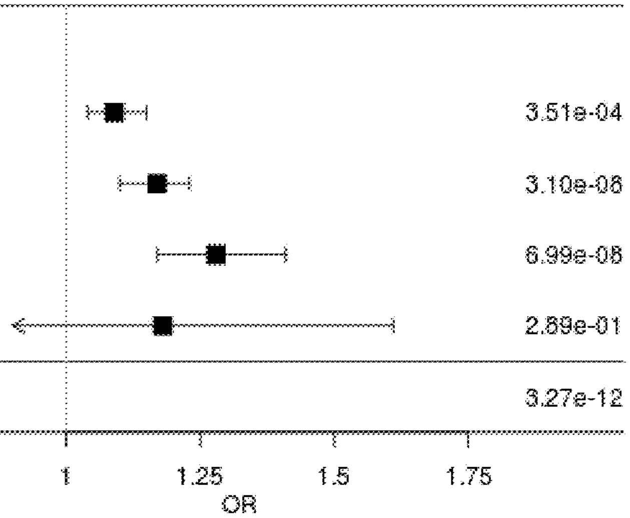
FIG. 6 (Panels A, B, and C) shows genetic score (total burden of rs1420101 and rs1342326 risk alleles) associations with (Panel A) Asthma (Panel B) COPD and (Panel C) ACOS. P-values odds ratios were estimated for individual scores; in each case the comparison was to individuals with zero risk alleles. Additionally, overall trend test p-values are shown.
Figure 6:
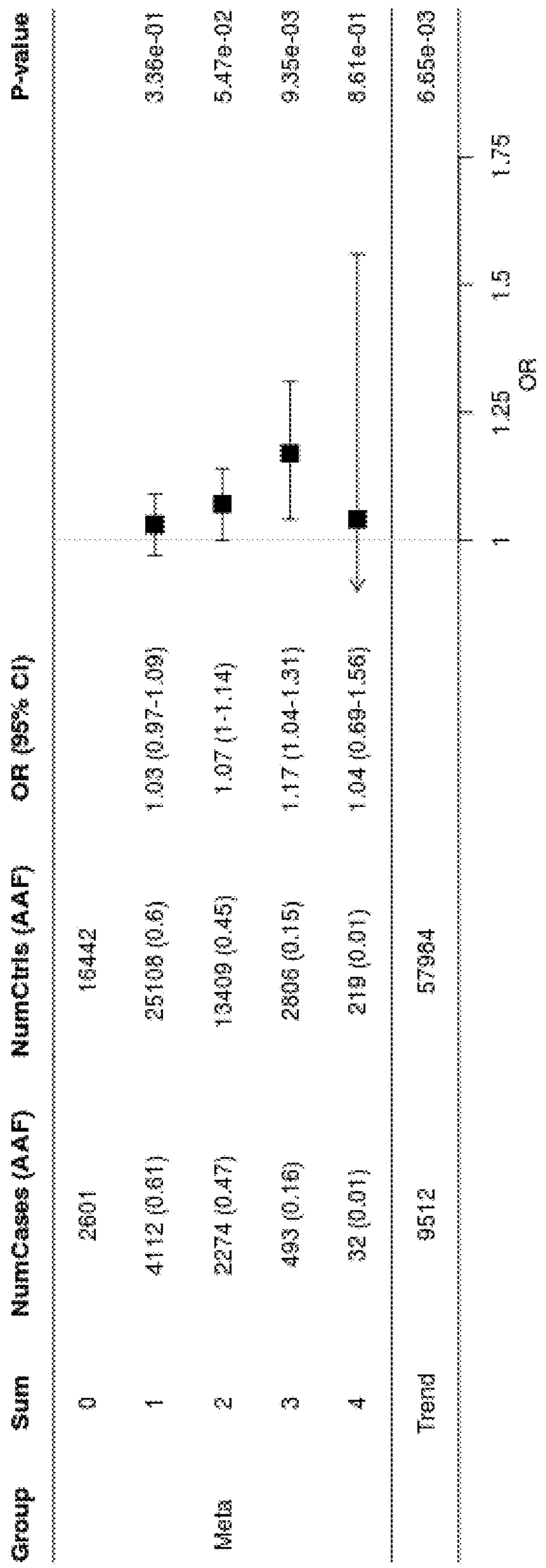
Figure 6:
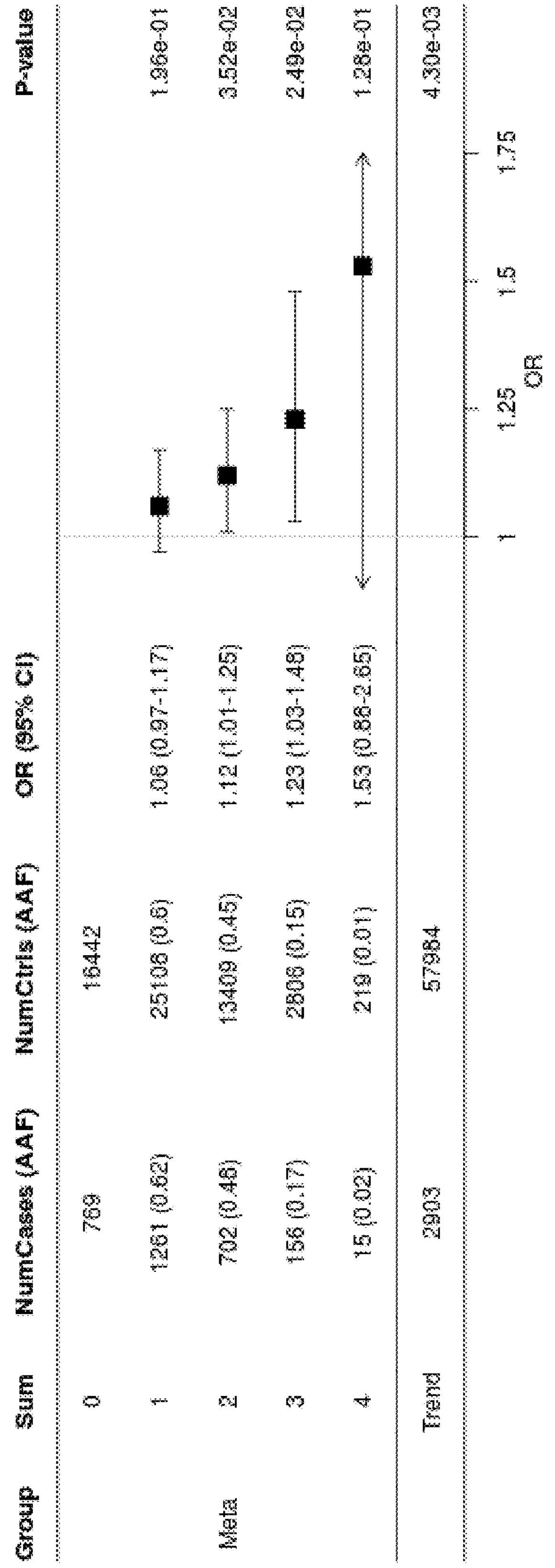

Since IL33 and IL1RL1 are part of the same signaling complex, and since these variants display notable allele-dosage dependence in their risk associations when analyzed individually, a two-variant genetic risk score was constructed by summing the number of risk alleles at IL33 (rs1342326) and IL1RL1 (rs1420101) (each individual had a score ranging from 0-4), and the association between the score and eosinophil counts and risk of asthma, COPD and ACOS was tested. Groups of individuals carrying each genetic risk score were compared to the group with zero risk alleles. In tests for trend, increasing genetic risk score was significantly associated with increasing eosinophil counts (FIG. 2, $P=1\times10^{-39}$) and increasing risk of asthma (FIG. 6, $P=3.27\times10^{12}$), COPD (FIG. 6, $P=6.65\times10^{-3}$), and ACOS ($P=4.3\times10^{-3}$). The largest effects (exceeding nominal significance) were observed for patients carrying three risk alleles (FIG. 2, for eosinophil counts, Meta beta=0.0071 (0.0057-0.0085) eos/ml, $P=8.8\times10^{-24}$; for asthma (FIG. 6), Meta OR=1.28 (1.17-1.41), $P=6.99\times10^{-8}$; for COPD (FIG. 6), OR=1.17 (1.04-1.31), $P=9.35\times10^{-3}$); and for ACOS (FIG. 6), OR=1.23 (1.03-1.48), $P=2.49\times10^{-2}$ (FIG. 2). Few individuals carried 4 risk alleles, and consequently effect size estimates had wide confidence intervals.

Figure 7:
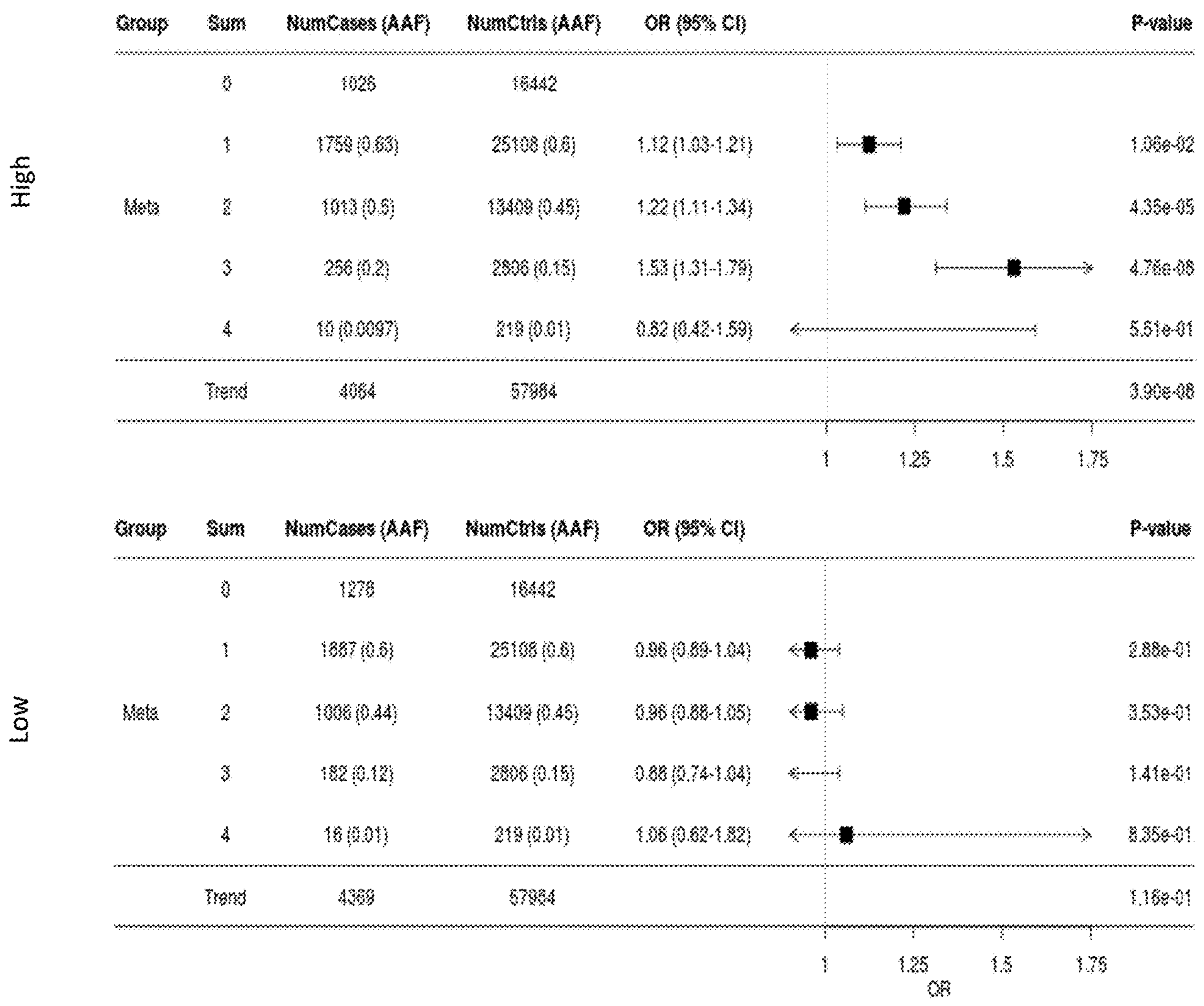
FIG. 7 (Panels A, B, and C) shows genetic score (total burden of rs1420101 and rs1342326 risk alleles) associations with (Panel A) High and Low Eosinophil Asthma (Panel B) High and Low Eosinophil COPD and (Panel C) High and Low Eosinophil ACOS. P-values odds ratios were estimated for individual scores; in each case the comparison was to individuals with zero risk alleles. Additionally, overall trend test p-values are shown.
Figure 7:
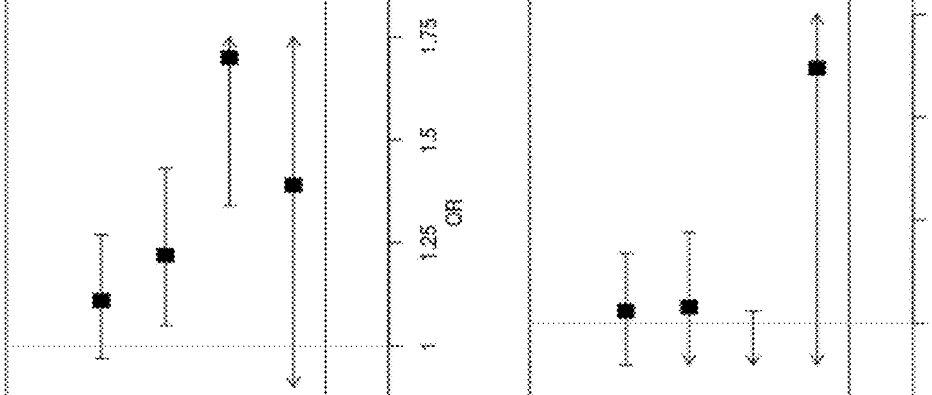

Associations between the two-variant score and high and low eosinophil patient subgroups was also assessed (FIG. 7). In trend tests, the score was significantly associated with high-eosinophil subsets of asthma ($P=1.37\times10^{-15}$), COPD ($P=3.9\times10^{-8}$), and ACOS ($P=1.8\times10^{-5}$), but not with low-eosinophil subsets of asthma, COPD, or ACOS (P>0.05 for each disease). The largest score-specific effects were observed for patients carrying three risk alleles (for high eosinophil asthma, Meta-OR=1.61 (1.42-1.84), P=6.33×

$10^{-13}$; for high eosinophil COPD, Meta-OR=1.53 (1.31-1.79), P=$4.76\times10^{-8}$); and for high eosinophil ACOS, OR=1.7 (1.34-2.14), P=$1\times10^{-5}$. As previously noted, there were relatively few individuals carrying 4 risk alleles, and respective effect size estimates had wide confidence intervals.

Predicted loss-of-function (pLOF) variants in IL33 are associated with decreased circulating eosinophil counts and obstructive lung disease risk. In analyses of IL33 pLOF variant rs146597587, IL33 inactivation is associated with reduced eosinophil counts (Meta-Beta=−0.02 (−0.03-0.0092, P=$7.3\times10^{-5}$) but not significantly with a reduced risk of eosinophilic asthma, COPD and ACOS (OR=0.82 (0.63-1.07), P=0.15, OR=0.99 (0.74-1.33), P=0.94, and OR=0.93 (0.56-1.53), P=0.76, respectively) (FIG. 7). IL1RL1 pLOF variation was not associated with risk of obstructive lung disease.

Analysis of IL1RL1 Variant Rs1420101 and IL33 Variant Rs1342326 with Other Airway Diseases.

Figure 9:
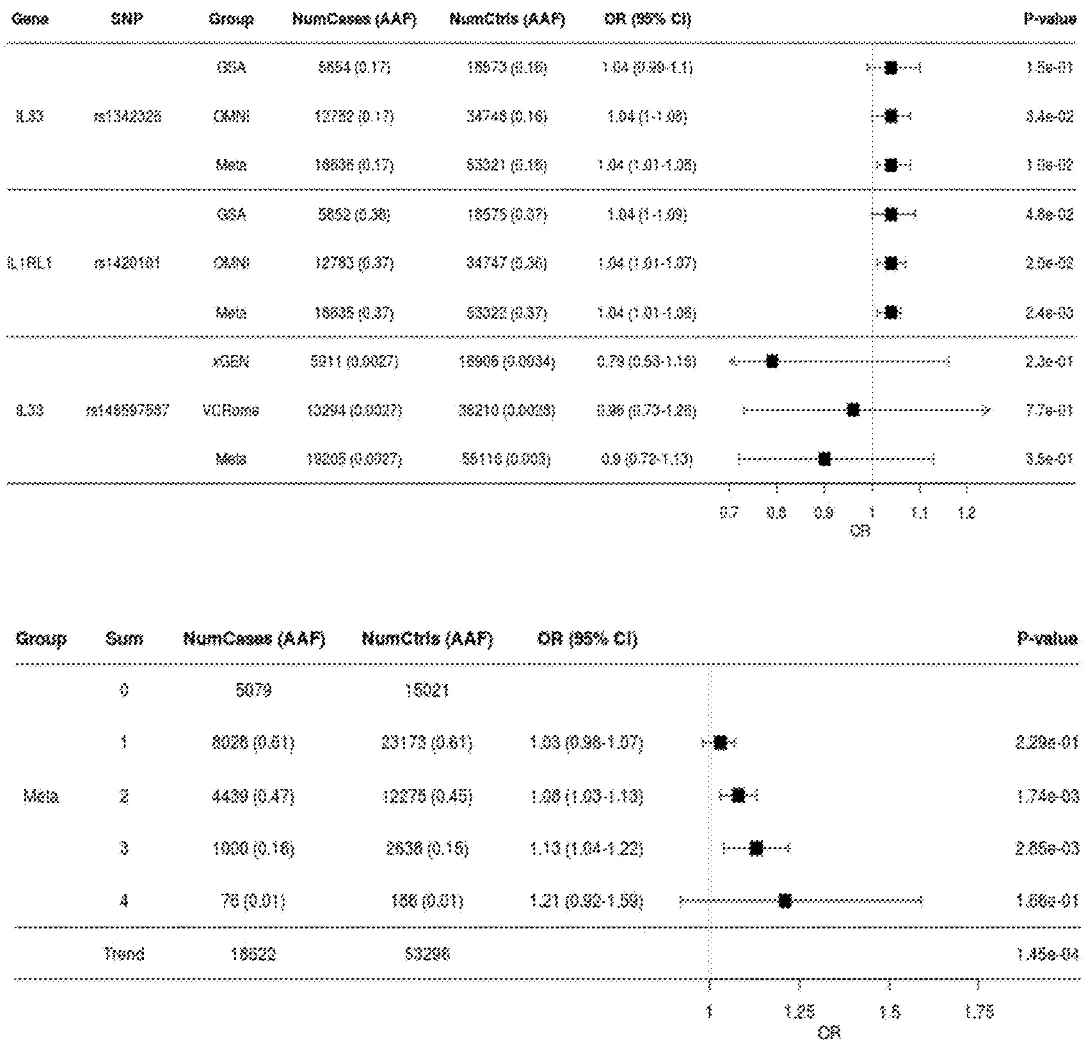
FIG. 9 (Panels A and B) shows rs1420101 (IL1RL1, also known as ST2), s1342326 (IL33), rs146597587 (IL33-pLoF) and genetic score (total burden of rs1420101 and rs1342326 risk alleles) associations with (Panel A) Allergic Rhinitis and (Panel B) Nasal Polyps. Odds ratios for disease were calculated using logistic regression, with adjustment for age, $age^2$, sex, smoking status and principal components of ancestry. To test the burden of common risk variants, p-values and odds ratios were estimated for each individual score; in each case the comparison was to individuals with zero risk alleles. Additionally, overall trend test p-values are shown.

The unified airway theory posits that asthma may co-occur with other airway disease due to common mechanisms. Therefore, other EHR-documented diseases of the airway for association with rs1420101 and rs1342326 were tested (FIG. 9). The IL33 variant rs1342326 and IL1RL1 variant rs1420101 was associated with an increased risk of allergic rhinitis (Meta-OR 1.04 (1.01-1.08), P=0.02; Meta-OR 1.04 (1.01-1.06), P=$2.4\times10^{-3}$) as well as an increased risk for nasal polyps (Meta-OR 1.48 (1.28-1.72), P=$1.2\times10^{-7}$, Meta-OR 1.17 (1.04-1.33), P=$1.2\times10^{-2}$). Furthermore, the burden of these common risk variants also significantly increased the risk for allergic rhinitis and nasal polys (P=$1.45\times10^{-4}$, P=$2.48\times10^{-7}$). These results are consistent with a previous report implicating IL33 common genetic variation in nasal polyps risk.

Summary.

IL33 is thought to be involved in barrier defense in epithelial tissues, including the lung epithelium, and has been implicated in asthma pathogenesis. The two variants described in this Example, IL33 (rs1342326) and IL1RL1 (rs1420101), have been previously associated with asthma in several studies. These reproducible and independent associations (IL33 is located on chromosome 9; IL1RL1 is located on chromosome 2) with both the ligand (IL33) and its specific receptor (IL1R1) suggest a role for IL33 signaling in asthma risk.

The current study significantly extends those previous findings. By performing whole exome sequencing and genotyping in over 83,000 adult participants of the DiscovEHR study associations were confirmed between IL33 and IL1RL1 and eosinophil counts as well as asthma, independently assessed as distinct phenotypes. Furthermore, a suggestive association of the IL33 and IL1RL1 variants with increased risk of COPD and ACOS was demonstrated—providing a genetic link supporting possibility of a shared mechanistic etiology between all three of these highly prevalent lung diseases. Associations of these variants with nasal polyps and allergic rhinitis were also demonstrated. In addition, it was found that in individuals carrying a larger burden of these risk alleles across both loci, larger effects on disease risk were observed. Furthermore, heterozygous carriers of a rare pLOF variants in IL33 had lower median lifetime eosinophil counts and trends reflecting about 20% decreased risk of asthma. It is believed that these data provide genetic evidence linking the IL33 pathway to asthma and possibly to COPD through an allelic series that includes both risk-increasing common alleles and risk-decreasing rare pLOF alleles.

It is believed that prior to this study, genetic variants in the IL33 pathway had not been previously associated with COPD. Similarly, it is believed that there was no prior genetic data linking the any pathway to the risk of the eosinophilic subsets of asthma, COPD and ACOS. The results of this Example suggest a link between enhanced IL33 signaling for increased risk of the eosinophilic subtypes of asthma and COPD and, the numerically higher risk associations seen with ACOS patients suggests that this entity at the intersection of these conditions may indeed have special features. In addition to providing a unifying genetic and mechanistic link between eosinophilic subsets of heretofore distinctly labeled obstructive lung diseases, the data also support the tenets of the "unified airway theory" that posits that eosinophilic lung diseases may represent a continuum with related upper airway diseases. In this respect, a markedly increased risk for the IL33 variant in allergic rhinitis and nasal polyps was observed.

Although not statistically significant, the protective associations with IL33 pLOF variants described in this Example are consistent with a recent study that demonstrated that a rare loss-of-function variant in IL33 was protective in asthma, supporting the possibility that inhibition of IL33 signaling may be an important therapeutic strategy for obstructive lung diseases. The data, in particular, suggest a role for interleukin-33 blockade in the eosinophilic forms of obstructive lung diseases such as asthma and COPD, as well as for eosinophilic upper airway diseases such as allergic rhinitis and nasal polyps.

Relatedly, recent progress with biologics in the treatment of severe and steroid-resistant asthma seems to distinguish eosinophilic disease. Multiple therapies that target interleukin-5 and interleukin-13 seem to only benefit the eosinophilic subset of asthma patients, while an antibody (Dupilumab) that blocks both the interleukin-4 and interleukin-13 pathways has numerically greater benefits in the eosinophilic patients, but also seems to have profound activity in the low-eosinophil subset. These therapies also seem to have benefit in nasal polyps and allergic rhinitis. Consistent with these previously described differences in the responses of eosinophilic asthma patients to biologics therapies, the data from this Example suggests that interleukin-33 blockade might best target the eosinophilic subsets of asthma, ACOS and COPD.

Although this study has certain limitations, it nonetheless represents a real-world clinical care setting, and in this population IL33 and IL1RL1 genetic variation is associated with increased risk of diagnosis of both asthma and COPD. For the purposes of personalized treatment of patients, whether one arrives at a diagnostic label of asthma, COPD, or ACOS is perhaps less important than identifying the mechanistic pathology that is occurring in a particular patient or group of patients, and these data suggest that subsets of asthma, COPD and ACOS patients may in part be driven by excess IL33 activity. Mitigating against various limitations of these data is the remarkable consistency of the findings using genetic variants in two different genes within the same pathway—parallel results were seen for variants in the gene for IL33 as well as for its receptor. For variants in both genes, consistent risk associations were seen across multiple related EHR-defined disease settings, and within these disease settings, consistent results were also repeatedly noted specific to the eosinophilic subsets of these diseases. Another convincing aspect of the data involves the consistent and notable allele-dependence of most of the risk associations, as well as the added power resulting from the two-variant risk score analyses. Finally, the reciprocal findings with the IL33 pLOF variants is also supportive.

These data suggest that genetic variation that enhances IL33 signaling contributes to increased risk of the eosinophilic forms of asthma, COPD and ACOS, and that pLOF genetic variants in IL33 may contribute to reduced risk of these diseases; risk of upper airway diseases such as nasal polyps also appears to be linked to IL33 signaling. Individuals carrying genetic variants that enhance IL33 signaling may represent an opportunity for precision medicine, as those particular asthma and COPD patients may benefit most from therapeutic blockade of IL33. The data also raise the possibility that patients suffering from eosinophilic airway disease, regardless of subtype and variant status, may benefit from inhibition of IL33.

The disclosure is not limited to the embodiments described and exemplified above, but is capable of variation and modification within the scope of the appended claims. U.S. application Ser. No. 15/827,357 filed Nov. 30, 2017 is incorporated herein by reference in its entirety for all purposes.

We claim:

1. A method for treating or inhibiting eosinophilic asthma, comprising administering an IL33 antagonist or a combination of an IL33 antagonist and an IL-4R antagonist to a subject having the IL33 variant rs1342326 but not having the intronic IL1RL1 variant rs1420101, or having both the intronic IL1RL1 variant rs1420101 and the IL33 variant rs1342326; wherein the IL33 antagonist comprises an antibody, or antigen-binding fragment thereof, that specifically binds to IL33 wherein the antibody, or antigen-binding fragment thereof, comprises the complementarity determining regions of a heavy chain comprising the amino acid sequence of SEQ ID NO:274 and the complementarity determining regions of a light chain comprising the amino acid sequence of SEQ ID NO:282; wherein the IL-4R antagonist comprises an antibody, or antigen-binding fragment thereof, that specifically binds to IL-4R wherein the antibody, or antigen-binding fragment thereof, comprises the complementarity determining regions of a heavy chain comprising the amino acid sequence of SEQ ID NO:337 and the complementarity determining regions of a light chain comprising the amino acid sequence of SEQ ID NO:338; and wherein eosinophilic asthma is treated or inhibited in the subject.

2. The method according to claim 1, wherein the subject has the intronic IL1RL1 variant rs1420101.

3. The method according to claim 1, wherein the subject has the IL33 variant rs1342326.

4. The method according to claim 1, wherein the subject has the IL33 variant rs1342326, and the intronic IL1RL1 variant rs1420101.

5. The method according to claim 1, wherein the IL33 antagonist comprises an IL33 trap.

6. The method according to claim 5, wherein the IL33 trap comprises a first IL33 binding domain comprising an IL33 binding portion of IL1RL1 and a second 1L33 binding domain comprising an extracellular portion of IL-1RAcP.

7. The method according to claim 1, wherein the IL-4R antibody comprises dupilumab.

8. The method according to claim 1, wherein the eosinophilic asthma is a high-eosinophilic subset of eosinophilic asthma.

9. The method according to claim 8, wherein the subject has the intronic 1L1RL1 variant rs1420101.

10. The method according to claim 8, wherein the subject has the IL33 variant rs1342326.

11. The method according to claim 8, wherein the subject has the IL33 variant rs1342326, and the intronic IL1RL1 variant rs1420101.

12. The method according to claim 8, wherein the IL33 antagonist comprises an IL33 trap.

13. The method according to claim 12, wherein the IL33 trap comprises a first IL33 binding domain comprising an IL33 binding portion of 1L1RL1 and a second 1L33 binding domain comprising an extracellular portion of IL-1RAcP.

14. The method according to claim 8, wherein the IL33 antagonist comprises an antibody or antigen-binding fragment thereof that specifically binds to IL33.

15. The method according to claim 14, wherein the antibody, or antigen-binding fragment thereof, that specifically binds to IL33 comprises the complementarity determining regions of a heavy chain comprising the amino acid sequence of SEQ ID NO:274 and the complementarity determining regions of a light chain comprising the amino acid sequence of SEQ ID NO:282.

16. The method according to claim 8, wherein the IL-4R antagonist comprises an antibody or antigen-binding fragment thereof that specifically binds to IL-4R.

17. The method according to claim 16, wherein the antibody, or antigen-binding fragment thereof, that specifically binds to IL-4R comprises the complementarity determining regions of a heavy chain comprising the amino acid sequence of SEQ ID NO:337 and the complementarity determining regions of a light chain comprising the amino acid sequence of SEQ ID NO:338.

18. The method according to claim 17, wherein the IL-4R antibody comprises dupilumab.

* * * * *

SEQUENCE LISTING

```
<160> NUMBER OF SEQ ID NOS: 358

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1

caggtgcagc tggtggagtc tgggggaggc gtggtccagc ctgggaggtc cctgagactc     60

tcctgtgcag cgtctggatt caccttcagt agttatggca tgcattgggt ccgccaggct    120

ccaggcaagg ggctggagtg ggtggcagtt atatggtatg atggaagaaa taaatactat    180

acagactccg tgaagggccg attcaccatc tccagagaca attccaagaa cacgctgtat    240

ctgcaaatgg acagcctgag agccgaggac acggctgtgt attactgtgc gagagagagg    300

tatatcagca gctattatgg ggggttcgac ccctggggcc agggagccct ggtcaccgtc    360

tcctca                                                               366


<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Arg Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Arg Glu Arg Tyr Ile Ser Ser Tyr Tyr Gly Gly Phe Asp Pro Trp
            100                 105                 110

Gly Gln Gly Ala Leu Val Thr Val Ser Ser
        115                 120


<210> SEQ ID NO 3
<211> LENGTH: 24
<212> TYPE: DNA
<213> ORGANISM: Artificial Sequence
```

<220> FEATURE:
<223> OTHER INFORMATION: Synthetic

<400> SEQUENCE: 3
ggattcacct tcagtagtta tggc 24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Ser Ser Tyr Gly
1 5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatggtatg atggaagaaa taaa 24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Trp Tyr Asp Gly Arg Asn Lys
1 5

<210> SEQ ID NO 7
<211> LENGTH: 45
<212> TYPE: DNA
<213> ORGANISM: Artificial Sequence
<220> FEATURE:
<223> OTHER INFORMATION: Synthetic

<400> SEQUENCE: 7
gcgagagaga ggtatatcag cagctattat gggggttcg acccc 45

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ala Arg Glu Arg Tyr Ile Ser Ser Tyr Tyr Gly Gly Phe Asp Pro
1 5 10 15

<210> SEQ ID NO 9
<211> LENGTH: 321
<212> TYPE: DNA
<213> ORGANISM: Artificial Sequence
<220> FEATURE:
<223> OTHER INFORMATION: Synthetic

<400> SEQUENCE: 9

```
gacatccaga tgacccagtc tccatcctcc gtgtctgcat ctgtaggaga cagagtcacc      60

atcacttgtc gggcgagtca gggtattagt agttggttag cctggtatca gcagaaacca     120

gggaaagccc ctaaggtcct gatctatgct gcatccagtt tgcaaagtgg ggtcccatca     180

aggttcagcg gcagtggatc tgggacagat ttcactctca ccatcagcag cctgcagcct     240

gaagattttg caacttacta ttgtcaacag gctaacagtt tcccattcac tttcggccct     300

gggaccaaac tggatatcaa g                                                321


<210> SEQ ID NO 10
<211> LENGTH: 107
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Leu Asp Ile Lys
            100                 105


<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

cagggtatta gtagttgg                                                     18


<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Gly Ile Ser Ser Trp
1               5


<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13
```

gctgcatcc 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caacaggcta acagtttccc attcact 27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Ala Asn Ser Phe Pro Phe Thr
1 5

<210> SEQ ID NO 17
<211> LENGTH: 357
<212> TYPE: DNA
<213> ORGANISM: Artificial Sequence
<220> FEATURE:
<223> OTHER INFORMATION: Synthetic

<400> SEQUENCE: 17
gaggtgcagc tgttggagtc tgggggagac ttggtacagc ctggggggtc cctgagactc 60
tcctgtgcag cctctggatt caccttcagc agctatgcca tgagctgggt ccgccaggct 120
ccagggaagg ggctggagtg ggtctcagtt attagtggta gtggaagtag cacagactac 180
gcagactccg tgaagggccg gttcaccatt tccagagaca attccaggga cacgctgcat 240
ctgcaaatga acagcctgag agccgaggac acggccgtat attactgtgc gaaaacgttc 300
tactacttct acggtttgga cgtctggggc caagggacca cggtcaccgt ctcctca 357

<210> SEQ ID NO 18
<211> LENGTH: 119
<212> TYPE: PRT
<213> ORGANISM: Artificial Sequence
<220> FEATURE:
<223> OTHER INFORMATION: Synthetic

<400> SEQUENCE: 18

Glu Val Gln Leu Leu Glu Ser Gly Gly Asp Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val

```
        35                  40                  45

Ser Val Ile Ser Gly Ser Gly Ser Ser Thr Asp Tyr Ala Asp Ser Val
    50                  55                  60

Lys Gly Arg Phe Thr Ile Ser Arg Asp Asn Ser Arg Asp Thr Leu His
65                  70                  75                  80

Leu Gln Met Asn Ser Leu Arg Ala Glu Asp Thr Ala Val Tyr Tyr Cys
                85                  90                  95

Ala Lys Thr Phe Tyr Tyr Phe Tyr Gly Leu Asp Val Trp Gly Gln Gly
            100                 105                 110

Thr Thr Val Thr Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagcagcta tgcc 24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly Phe Thr Phe Ser Ser Tyr Ala
1               5
```

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
attagtggta gtggaagtag caca 24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

```
Ile Ser Gly Ser Gly Ser Ser Thr
1               5
```

<210> SEQ ID NO 23
<211> LENGTH: 36
<212> TYPE: DNA
<213> ORGANISM: Artificial Sequence
<220> FEATURE:
<223> OTHER INFORMATION: Synthetic

<400> SEQUENCE: 23
gcgaaaacgt tctactactt ctacggtttg gacgtc 36

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

```
Ala Lys Thr Phe Tyr Tyr Phe Tyr Gly Leu Asp Val
1               5                   10
```

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25

```
gacatccaga tgacccagtc tccatcctcc ctgtctgcat ctttaagaga cagagtcacc     60

atcacttgcc gggcgagtca gggcattagc aattatttag cctggtatca gcagaaacca    120

gggaaagttc ctaaggtcct aatctatgct gcatccactt tgcaatcagg ggtcccatct    180

cggttcagtg gcagtggatc tgggacagtt ttcactctca ccatcagcag cctgcagact    240

gaagatgttg caacttatta ctgtcaaaag tatagcagtg ccccattcac tttcggccct    300

gggaccaaag tggatatcaa a                                              321
```

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

```
Asp Ile Gln Met Thr Gln Ser Pro Ser Ser Leu Ser Ala Ser Leu Arg
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Val Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Val Phe Thr Leu Thr Ile Ser Ser Leu Gln Thr
65                  70                  75                  80

Glu Asp Val Ala Thr Tyr Tyr Cys Gln Lys Tyr Ser Ser Ala Pro Phe
                85                  90                  95

Thr Phe Gly Pro Gly Thr Lys Val Asp Ile Lys
            100                 105
```

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27

```
cagggcatta gcaattat                                                   18
```

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Gly Ile Ser Asn Tyr
1 5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc 9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caaaagtata gcagtgcccc attcact 27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Lys Tyr Ser Ser Ala Pro Phe Thr
1 5

<210> SEQ ID NO 33
<211> LENGTH: 351
<212> TYPE: DNA
<213> ORGANISM: Artificial Sequence
<220> FEATURE:
<223> OTHER INFORMATION: Synthetic

<400> SEQUENCE: 33
caggtgcttc tggtacagtc tggggctgag gtgaagaagc ctggggccac agtgaaggtc 60
tcctgcaagg cttctggatc cactttcacc ggctactata tgcactgggt gcgacaggcc 120
cctggacaag ggcttgagtg gatgggatgg atcaacccta acaatggtgg cacaaactat 180
gcacagaagt ttcagggcag ggtcaccatg accagggaca cgtccatcag cacagcctac 240
atggaattga gcaggctgag atctgacgac acggccgtat attactgtgc gagagagttg 300
cggtataact ggaagtcctg gggccaggga accctggtca ccgtctcctc a 351

<210> SEQ ID NO 34
<211> LENGTH: 117
<212> TYPE: PRT
<213> ORGANISM: Artificial Sequence
<220> FEATURE:
<223> OTHER INFORMATION: Synthetic

<400> SEQUENCE: 34

Gln Val Leu Leu Val Gln Ser Gly Ala Glu Val Lys Lys Pro Gly Ala
1 5 10 15

Thr Val Lys Val Ser Cys Lys Ala Ser Gly Ser Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Asn Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Glu Leu Arg Tyr Asn Trp Lys Ser Trp Gly Gln Gly Thr Leu
100 105 110

Val Thr Val Ser Ser
115

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggatccactt tcaccggcta ctat 24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Ser Thr Phe Thr Gly Tyr Tyr
1 5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
atcaacccta acaatggtgg caca 24

<210> SEQ ID NO 38
<211> LENGTH: 8

<212> TYPE: PRT
<213> ORGANISM: Artificial Sequence
<220> FEATURE:
<223> OTHER INFORMATION: Synthetic

<400> SEQUENCE: 38

Ile Asn Pro Asn Asn Gly Gly Thr
1 5

<210> SEQ ID NO 39
<211> LENGTH: 30
<212> TYPE: DNA
<213> ORGANISM: Artificial Sequence
<220> FEATURE:
<223> OTHER INFORMATION: Synthetic

<400> SEQUENCE: 39
gcgagagagt tgcggtataa ctggaagtcc 30

<210> SEQ ID NO 40
<211> LENGTH: 10
<212> TYPE: PRT
<213> ORGANISM: Artificial Sequence
<220> FEATURE:
<223> OTHER INFORMATION: Synthetic

<400> SEQUENCE: 40

Ala Arg Glu Leu Arg Tyr Asn Trp Lys Ser
1 5 10

<210> SEQ ID NO 41
<211> LENGTH: 324
<212> TYPE: DNA
<213> ORGANISM: Artificial Sequence
<220> FEATURE:
<223> OTHER INFORMATION: Synthetic

<400> SEQUENCE: 41
gaaattgtgt tgacgcagtc tccaggcacc ctgtctttgt ctccagggga aagagtcacc 60
ctctcctgca gggccagtca gagtgttggc aggccctact tagcctggta ccaacagata 120
cctggccagg ctcccaggct cctcatctat ggtgcatcca gcagggccac tgacatccca 180
gacaggttca gtggcaatgg gtctgggaca gacttcactc tcaccatcag tagactggag 240
cctgaagatt ttgcagtgta ttactgtcag cagtatgata attcccctta tacttttggc 300
caggggacca ggctggagat caaa 324

<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Glu Ile Val Leu Thr Gln Ser Pro Gly Thr Leu Ser Leu Ser Pro Gly
1 5 10 15

Glu Arg Val Thr Leu Ser Cys Arg Ala Ser Gln Ser Val Gly Arg Pro
20 25 30

Tyr Leu Ala Trp Tyr Gln Gln Ile Pro Gly Gln Ala Pro Arg Leu Leu
35 40 45

Ile Tyr Gly Ala Ser Ser Arg Ala Thr Asp Ile Pro Asp Arg Phe Ser
50 55 60

```
Gly Asn Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Asn Ser Pro
                85                  90                  95

Tyr Thr Phe Gly Gln Gly Thr Arg Leu Glu Ile Lys
            100                 105


<210> SEQ ID NO 43
<211> LENGTH: 21
<212> TYPE: DNA
<213> ORGANISM: Artificial Sequence
<220> FEATURE:
<223> OTHER INFORMATION: Synthetic

<400> SEQUENCE: 43

cagagtgttg gcaggcccta c                                              21


<210> SEQ ID NO 44
<211> LENGTH: 7
<212> TYPE: PRT
<213> ORGANISM: Artificial Sequence
<220> FEATURE:
<223> OTHER INFORMATION: Synthetic

<400> SEQUENCE: 44

Gln Ser Val Gly Arg Pro Tyr
1               5


<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45

ggtgcatcc                                                             9


<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Gly Ala Ser
1


<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47

cagcagtatg ataattcccc ttatact                                        27


<210> SEQ ID NO 48
<211> LENGTH: 9
<212> TYPE: PRT
<213> ORGANISM: Artificial Sequence
<220> FEATURE:
<223> OTHER INFORMATION: Synthetic
```

<400> SEQUENCE: 48

Gln Gln Tyr Asp Asn Ser Pro Tyr Thr
1               5

<210> SEQ ID NO 49
<211> LENGTH: 366
<212> TYPE: DNA
<213> ORGANISM: Artificial Sequence
<220> FEATURE:
<223> OTHER INFORMATION: Synthetic

<400> SEQUENCE: 49
gaggtgcagc tggtggagtc tgggggaggc ttggtacaac ctggggggtc cctgagactc 60
tcctgtgcag cctctggatt cacctttaga agctttgcca tgagctgggt ccgccaggct 120
ccagggaagg ggctggaatt ggtctcagat ctcaggacta gtggtggtag tacatactac 180
gcagactccg tgaagggccg gctcaccatc tccagagaca attccaagaa cacgctgtat 240
ctgcaaatga acagcctgag agccgaggac acggccgtat attactgtgc gaaaagccac 300
tatagcacca gctggttcgg gggctttgac tactggggcc agggaaccct ggtcactgtc 360
tcctca 366

<210> SEQ ID NO 50
<211> LENGTH: 122
<212> TYPE: PRT
<213> ORGANISM: Artificial Sequence
<220> FEATURE:
<223> OTHER INFORMATION: Synthetic

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Ala Met Ser Trp Val Arg Gln Ala Pro Gly Lys Gly Leu Glu Leu Val
        35                  40                  45

Ser Asp Leu Arg Thr Ser Gly Gly Ser Thr Tyr Tyr Ala Asp Ser Val
    50                  55                  60

Lys Gly Arg Leu Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser His Tyr Ser Thr Ser Trp Phe Gly Gly Phe Asp Tyr Trp
            100                 105                 110

Gly Gln Gly Thr Leu Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct ttagaagctt tgcc 24

<210> SEQ ID NO 52
<211> LENGTH: 8
<212> TYPE: PRT

<213> ORGANISM: Artificial Sequence
<220> FEATURE:
<223> OTHER INFORMATION: Synthetic

<400> SEQUENCE: 52

Gly Phe Thr Phe Arg Ser Phe Ala
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
ctcaggacta gtggtggtag taca 24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Leu Arg Thr Ser Gly Gly Ser Thr
1               5

<210> SEQ ID NO 55
<211> LENGTH: 45
<212> TYPE: DNA
<213> ORGANISM: Artificial Sequence
<220> FEATURE:
<223> OTHER INFORMATION: Synthetic

<400> SEQUENCE: 55
gcgaaaagcc actatagcac cagctggttc gggggctttg actac 45

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Ala Lys Ser His Tyr Ser Thr Ser Trp Phe Gly Gly Phe Asp Tyr
1               5                   10                  15

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcttcc gtgtctgctt ctgtaggaga cagagtcacc 60
atcacttgtc gggcgagtca gggttttagc agctggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcaccaa cctgcagcct 240
gaagattttg caacttacta ttgtcaacag gctaacagtt tccctctcac tttcggcgga 300

-continued gggaccaagg tggagatcaa a 321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Phe Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Thr Asn Leu Gln Pro
65 70 75 80

Glu Asp Phe Ala Thr Tyr Tyr Cys Gln Gln Ala Asn Ser Phe Pro Leu
85 90 95

Thr Phe Gly Gly Gly Thr Lys Val Glu Ile Lys
100 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagggtttta gcagctgg 18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Gly Phe Ser Ser Trp
1 5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gctgcatcc 9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacaggcta acagtttccc tctcact 27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Ala Asn Ser Phe Pro Leu Thr
1 5

<210> SEQ ID NO 65
<211> LENGTH: 366
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtacagc ctggggggtc cctgagactc 60
tcctgtgcag cctctggatt cacgtttagc agctatgtca tgagctgggt ccgccaggct 120
ccagggaagg ggctggagtg ggtctcaagt attagtggta atggtggtag cacaaactac 180
gcagactccg tgaagggccg gttcaccatc tccagagaca attccaagaa cacgctgttt 240
ctggaaatga acagcctgag agccgaggac acggccgtat attactgtgc gaaatcactg 300
ggaactacca cgactttttt ggggtttgac tattggggcc agggaaccct ggtcaccgtc 360
tcctca 366

<210> SEQ ID NO 66
<211> LENGTH: 122
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Val Met Ser Trp Val Arg Gln Ala Pro Gly Lys Gly Leu Glu Trp Val
35 40 45

Ser Ser Ile Ser Gly Asn Gly Gly Ser Thr Asn Tyr Ala Asp Ser Val
50 55 60

Lys Gly Arg Phe Thr Ile Ser Arg Asp Asn Ser Lys Asn Thr Leu Phe
65 70 75 80

Leu Glu Met Asn Ser Leu Arg Ala Glu Asp Thr Ala Val Tyr Tyr Cys

-continued

```
                85                  90                  95

Ala Lys Ser Leu Gly Thr Thr Thr Thr Phe Leu Gly Phe Asp Tyr Trp
            100                 105                 110

Gly Gln Gly Thr Leu Val Thr Val Ser Ser
        115                 120


<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67

ggattcacgt ttagcagcta tgtc                                            24


<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Ser Tyr Val
1               5


<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69

attagtggta atggtggtag caca                                            24


<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Ser Gly Asn Gly Gly Ser Thr
1               5


<210> SEQ ID NO 71
<211> LENGTH: 45
<212> TYPE: DNA
<213> ORGANISM: Artificial Sequence
<220> FEATURE:
<223> OTHER INFORMATION: Synthetic

<400> SEQUENCE: 71

gcgaaatcac tgggaactac cacgactttt ttggggtttg actat                     45


<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72
```

Ala Lys Ser Leu Gly Thr Thr Thr Thr Phe Leu Gly Phe Asp Tyr
1 5 10 15

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaaactcct gatctatgct gcatccagtt tgcaaagtgg ggtcccatca 180
aggttcagcg gcagtggatc tgggacatat ttcactctca ccatcagcag cctgcagcct 240
gaagattttg caacttacta ttgtcaacag gctaacagtt tccctctcac tttcggcgga 300
gggaccaagg tggagatcaa a 321

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Tyr Phe Thr Leu Thr Ile Ser Ser Leu Gln Pro
65 70 75 80

Glu Asp Phe Ala Thr Tyr Tyr Cys Gln Gln Ala Asn Ser Phe Pro Leu
85 90 95

Thr Phe Gly Gly Gly Thr Lys Val Glu Ile Lys
100 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagggtatta gcagctgg 18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Gly Ile Ser Ser Trp
1 5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc 9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacaggcta acagtttccc tctcact 27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Ala Asn Ser Phe Pro Leu Thr
1 5

<210> SEQ ID NO 81
<211> LENGTH: 363
<212> TYPE: DNA
<213> ORGANISM: Artificial Sequence
<220> FEATURE:
<223> OTHER INFORMATION: Synthetic

<400> SEQUENCE: 81
caggtgcagc tgcaggagtc gggcccagga ctggtgaagc cttcggagac cctgtccctc 60
acctgcactg tctctggtgg ctccatcagt agttattact ggagctggat ccggcagccc 120
ccagggaagg gactggagtt gattgggtat atttattaca gtgggagcac caattataac 180
ccctccctca agagtcgagt caccatatct gtagacacgt ccaagaacca cttctccctg 240
aagctgagct ctgtgaccgc tgcggacacg gccgtatatt actgtgcgag atcccagtat 300
accagtagtt ggtacggttc ttttgatatc tggggccaag ggacaatggt caccgtctct 360
tca 363

<210> SEQ ID NO 82

<211> LENGTH: 121
<212> TYPE: PRT
<213> ORGANISM: Artificial Sequence
<220> FEATURE:
<223> OTHER INFORMATION: Synthetic

<400> SEQUENCE: 82

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Pro Gly Lys Gly Leu Glu Leu Ile
35 40 45

Gly Tyr Ile Tyr Tyr Ser Gly Ser Thr Asn Tyr Asn Pro Ser Leu Lys
50 55 60

Ser Arg Val Thr Ile Ser Val Asp Thr Ser Lys Asn His Phe Ser Leu
65 70 75 80

Lys Leu Ser Ser Val Thr Ala Ala Asp Thr Ala Val Tyr Tyr Cys Ala
85 90 95

Arg Ser Gln Tyr Thr Ser Ser Trp Tyr Gly Ser Phe Asp Ile Trp Gly
100 105 110

Gln Gly Thr Met Val Thr Val Ser Ser
115 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggtggctcca tcagtagtta ttac 24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Gly Ser Ile Ser Ser Tyr Tyr
1 5

<210> SEQ ID NO 85
<211> LENGTH: 21
<212> TYPE: DNA
<213> ORGANISM: Artificial Sequence
<220> FEATURE:
<223> OTHER INFORMATION: Synthetic

<400> SEQUENCE: 85
atttattaca gtgggagcac c 21

<210> SEQ ID NO 86
<211> LENGTH: 7
<212> TYPE: PRT
<213> ORGANISM: Artificial Sequence
<220> FEATURE:
<223> OTHER INFORMATION: Synthetic

<400> SEQUENCE: 86

Ile Tyr Tyr Ser Gly Ser Thr
1 5

<210> SEQ ID NO 87
<211> LENGTH: 45
<212> TYPE: DNA
<213> ORGANISM: Artificial Sequence
<220> FEATURE:
<223> OTHER INFORMATION: Synthetic

<400> SEQUENCE: 87
gcgagatccc agtataccag tagttggtac ggttcttttg atatc 45

<210> SEQ ID NO 88
<211> LENGTH: 15
<212> TYPE: PRT
<213> ORGANISM: Artificial Sequence
<220> FEATURE:
<223> OTHER INFORMATION: Synthetic

<400> SEQUENCE: 88

Ala Arg Ser Gln Tyr Thr Ser Ser Trp Tyr Gly Ser Phe Asp Ile
1 5 10 15

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatcttcc gtgtctgcat ctgtaggaga cagagtcacc 60
atcacttgtc gggcgagtca gggtattagc acctggttag cctggtttca gcagaaacca 120
gggaaagccc ctaagctcct gatctatgct gcatccactt tacaaggtgg ggtcccatca 180
aggttcagcg gcagtggatc tgggccagaa ttcactctca ccatcagcag cctgcagcct 240
gaagattttg caacttacta ttgtcaacag gctaacagtt tcccgtggac gttcggccaa 300
gggaccaagg tggaaatcaa a 321

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Thr Trp
20 25 30

Leu Ala Trp Phe Gln Gln Lys Pro Gly Lys Ala Pro Lys Leu Leu Ile
35 40 45

Tyr Ala Ala Ser Thr Leu Gln Gly Gly Val Pro Ser Arg Phe Ser Gly
50 55 60

Ser Gly Ser Gly Pro Glu Phe Thr Leu Thr Ile Ser Ser Leu Gln Pro
65 70 75 80

Glu Asp Phe Ala Thr Tyr Tyr Cys Gln Gln Ala Asn Ser Phe Pro Trp
85 90 95

Thr Phe Gly Gln Gly Thr Lys Val Glu Ile Lys 100 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagggtatta gcacctgg 18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Gly Ile Ser Thr Trp
1 5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc 9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacaggcta acagtttccc gtggacg 27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Ala Asn Ser Phe Pro Trp Thr
1 5

<210> SEQ ID NO 97

<211> LENGTH: 366
<212> TYPE: DNA
<213> ORGANISM: Artificial Sequence
<220> FEATURE:
<223> OTHER INFORMATION: Synthetic

<400> SEQUENCE: 97
caggttcagc tggtgcagtc tggagctgag gtgaagaagc ctggggcctc agtgaaggtc 60
tcctgcaagg cctctggtta cacctttaac agctatggta tcagctgggt gcgacaggcc 120
cctggacaag ggcttgagtg gatgggatgg atcagctccc acaatggtaa cagtcactat 180
gtacagaagt tccagggcag agtctccatg accacagaca catccacgag tacagcctac 240
atggaactga ggagccttag atctgacgac acggccgtgt attactgtgc gagacactcg 300
tataccacca gctggtacgg gggttttgac tattggggcc agggaaccct ggtcaccgtc 360
tcctca 366

<210> SEQ ID NO 98
<211> LENGTH: 122
<212> TYPE: PRT
<213> ORGANISM: Artificial Sequence
<220> FEATURE:
<223> OTHER INFORMATION: Synthetic

<400> SEQUENCE: 98

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Asn Ser Tyr
20 25 30

Gly Ile Ser Trp Val Arg Gln Ala Pro Gly Gln Gly Leu Glu Trp Met
35 40 45

Gly Trp Ile Ser Ser His Asn Gly Asn Ser His Tyr Val Gln Lys Phe
50 55 60

Gln Gly Arg Val Ser Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg His Ser Tyr Thr Thr Ser Trp Tyr Gly Gly Phe Asp Tyr Trp
100 105 110

Gly Gln Gly Thr Leu Val Thr Val Ser Ser
115 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggttacacct ttaacagcta tggt 24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Tyr Thr Phe Asn Ser Tyr Gly 1 5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
atcagctccc acaatggtaa cagt 24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Ser His Asn Gly Asn Ser
1 5

<210> SEQ ID NO 103
<211> LENGTH: 45
<212> TYPE: DNA
<213> ORGANISM: Artificial Sequence
<220> FEATURE:
<223> OTHER INFORMATION: Synthetic

<400> SEQUENCE: 103
gcgagacact cgtataccac cagctggtac gggggttttg actat 45

<210> SEQ ID NO 104
<211> LENGTH: 15
<212> TYPE: PRT
<213> ORGANISM: Artificial Sequence
<220> FEATURE:
<223> OTHER INFORMATION: Synthetic

<400> SEQUENCE: 104

Ala Arg His Ser Tyr Thr Thr Ser Trp Tyr Gly Gly Phe Asp Tyr
1 5 10 15

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcttcc gtgtctgcat ctgtaggaga cagagtcacc 60
atcacttgtc gggcgagtca gggttttagc agctggttag cctggtatca gcagaaacca 120
gggaaagccc ctcagctcct gatctatgct gcatccagtt tgcaaagtgg ggtcccatca 180
aggttcagcg gcagtggatc tgggtcagat ttcactctca ccatcagcag cctgcagcct 240
gaagattttg caacttacta ttgtcaacag gctaacagtt tccctctcac tttcggcgga 300
gggaccaagg tggagatcaa a 321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Phe Ser Ser Trp
20 25 30

Leu Ala Trp Tyr Gln Gln Lys Pro Gly Lys Ala Pro Gln Leu Leu Ile
35 40 45

Tyr Ala Ala Ser Ser Leu Gln Ser Gly Val Pro Ser Arg Phe Ser Gly
50 55 60

Ser Gly Ser Gly Ser Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Leu
85 90 95

Thr Phe Gly Gly Gly Thr Lys Val Glu Ile Lys
100 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagggtttta gcagctgg 18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Gly Phe Ser Ser Trp
1 5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcatcc 9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
1

<210> SEQ ID NO 111
<211> LENGTH: 27

<212> TYPE: DNA
<213> ORGANISM: Artificial Sequence
<220> FEATURE:
<223> OTHER INFORMATION: Synthetic

<400> SEQUENCE: 111
caacaggcta acagtttccc tctcact 27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Ala Asn Ser Phe Pro Leu Thr
1 5

<210> SEQ ID NO 113
<211> LENGTH: 366
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc cgggggaggc ttggttcagc cggggggggtc cctgagactc 60 tcctgtgcag cctctggaat caccttgagc agctatggca tgagctgggt ccgccaggct 120
ccagggaagg gactggagtg ggtcgcatcc atttttggta gtggtggtgg cccatactac 180
gcagactccg tgaagggccg gttcaccatg tccagagaca attccaagaa cacgctgtat 240
ttgcaaatga acagcctgag agccgaggac acggccgtat attattgtgc gaaagatcga 300
tacagtggga gctactacgg aggttttgac tactggggcc ggggaaccct ggtcaccgtc 360
tcctca 366

<210> SEQ ID NO 114
<211> LENGTH: 122
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1 5 10 15

Ser Leu Arg Leu Ser Cys Ala Ala Ser Gly Ile Thr Leu Ser Ser Tyr
20 25 30

Gly Met Ser Trp Val Arg Gln Ala Pro Gly Lys Gly Leu Glu Trp Val
35 40 45

Ala Ser Ile Phe Gly Ser Gly Gly Gly Pro Tyr Tyr Ala Asp Ser Val
50 55 60

Lys Gly Arg Phe Thr Met Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Arg Tyr Ser Gly Ser Tyr Tyr Gly Gly Phe Asp Tyr Trp
100 105 110

Gly Arg Gly Thr Leu Val Thr Val Ser Ser
115 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggaatcacct tgagcagcta tggc 24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Ile Thr Leu Ser Ser Tyr Gly
1 5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
atttttggta gtggtggtgg ccca 24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Phe Gly Ser Gly Gly Gly Pro
1 5

<210> SEQ ID NO 119
<211> LENGTH: 45
<212> TYPE: DNA
<213> ORGANISM: Artificial Sequence
<220> FEATURE:
<223> OTHER INFORMATION: Synthetic

<400> SEQUENCE: 119
gcgaaagatc gatacagtgg gagctactac ggaggttttg actac 45

<210> SEQ ID NO 120
<211> LENGTH: 15
<212> TYPE: PRT
<213> ORGANISM: Artificial Sequence
<220> FEATURE:
<223> OTHER INFORMATION: Synthetic

<400> SEQUENCE: 120

Ala Lys Asp Arg Tyr Ser Gly Ser Tyr Tyr Gly Gly Phe Asp Tyr
1 5 10 15

<210> SEQ ID NO 121
<211> LENGTH: 321

<212> TYPE: DNA
<213> ORGANISM: Artificial Sequence
<220> FEATURE:
<223> OTHER INFORMATION: Synthetic

<400> SEQUENCE: 121
gacatccaga tgacccagtc tccatcttcc gtgtctgcat ctgtaggaga cagagtcacc 60
atcacttgtc gggcgagtca gggtattacc agctggttag cctggtatca gcagaaacca 120
gggaaagccc ctacactcct gatctatgct gcatccagtt tgcaaactgg ggtcccatca 180
aggttcagcg gcagtggatc tgggacagat ttcactctca ccatcagcag cctgcagcct 240
gaacattttg caacttacta ttgtcaacag gctaacagtt tccctcctac tttcggcgga 300
gggaccaagg tggagatcaa a 321

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Thr Ser Trp
20 25 30

Leu Ala Trp Tyr Gln Gln Lys Pro Gly Lys Ala Pro Thr Leu Leu Ile
35 40 45

Tyr Ala Ala Ser Ser Leu Gln Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu His Phe Ala Thr Tyr Tyr Cys Gln Gln Ala Asn Ser Phe Pro Pro
85 90 95

Thr Phe Gly Gly Gly Thr Lys Val Glu Ile Lys
100 105

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagggtatta ccagctgg 18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Gly Ile Thr Ser Trp
1 5

<210> SEQ ID NO 125
<211> LENGTH: 9
<212> TYPE: DNA

<213> ORGANISM: Artificial Sequence
<220> FEATURE:
<223> OTHER INFORMATION: Synthetic

<400> SEQUENCE: 125 gctgcatcc 9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Ala Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
caacaggcta acagtttccc tcctact 27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Ala Asn Ser Phe Pro Pro Thr
1 5

<210> SEQ ID NO 129
<211> LENGTH: 366
<212> TYPE: DNA
<213> ORGANISM: Artificial Sequence
<220> FEATURE:
<223> OTHER INFORMATION: Synthetic

<400> SEQUENCE: 129
gaggtgcagc tggtggagtc tgggggaggc ttggtacagc ctggggggtc cctaagactc 60
tcctgtgcag cctctggatt cacctttagc agttatgcct tgacctgggt ccgccaggct 120
ccagggaagg ggctggagtg ggtctctttt attagtggta gtggtggtag gccattctac 180
gcagactccg tgaagggccg gttcaccatc tccagagaca attccaagaa catgctgtat 240
ctgcaaatga acagcctgag agccgaggac acggccatat attactgtgc gaagtccctg 300
tataccacca gctggtacgg ggggttcgac tcctggggcc agggaaccct ggtcaccgtc 360
tcctca 366

<210> SEQ ID NO 130
<211> LENGTH: 122
<212> TYPE: PRT
<213> ORGANISM: Artificial Sequence
<220> FEATURE:
<223> OTHER INFORMATION: Synthetic

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Leu Thr Trp Val Arg Gln Ala Pro Gly Lys Gly Leu Glu Trp Val
        35                  40                  45

Ser Phe Ile Ser Gly Ser Gly Gly Arg Pro Phe Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Ile Tyr Tyr Cys
                85                  90                  95

Ala Lys Ser Leu Tyr Thr Thr Ser Trp Tyr Gly Gly Phe Asp Ser Trp
            100                 105                 110

Gly Gln Gly Thr Leu Val Thr Val Ser Ser
        115                 120

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggattcacct ttagcagtta tgcc 24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Phe Thr Phe Ser Ser Tyr Ala
1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
attagtggta gtggtggtag gcca 24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ser Gly Ser Gly Gly Arg Pro
1               5

<210> SEQ ID NO 135
<211> LENGTH: 45
<212> TYPE: DNA

<213> ORGANISM: Artificial Sequence
<220> FEATURE:
<223> OTHER INFORMATION: Synthetic

<400> SEQUENCE: 135
gcgaagtccc tgtataccac cagctggtac ggggggttcg actcc 45

<210> SEQ ID NO 136
<211> LENGTH: 15
<212> TYPE: PRT
<213> ORGANISM: Artificial Sequence
<220> FEATURE:
<223> OTHER INFORMATION: Synthetic

<400> SEQUENCE: 136

Ala Lys Ser Leu Tyr Thr Thr Ser Trp Tyr Gly Gly Phe Asp Ser
1 5 10 15

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcttcc gtgtctgcat ctgtaggaga cagagtcacc 60
atcacttgtc gggcgagtca gggtgtcgtc agctggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttatta ttgtcaacag tctaacagtt tccctttcac tctcggccct 300
gggaccaaag tggatatcaa a 321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Val Val Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Asn Ser Phe Pro Phe
85 90 95

Thr Leu Gly Pro Gly Thr Lys Val Asp Ile Lys
100 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagggtgtcg tcagctgg 18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Gly Val Val Ser Trp
1 5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctgcatcc 9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
1

<210> SEQ ID NO 143
<211> LENGTH: 24
<212> TYPE: DNA
<213> ORGANISM: Artificial Sequence
<220> FEATURE:
<223> OTHER INFORMATION: Synthetic

<400> SEQUENCE: 143
caacagtcta acagtttccc tttc 24

<210> SEQ ID NO 144
<211> LENGTH: 8
<212> TYPE: PRT
<213> ORGANISM: Artificial Sequence
<220> FEATURE:
<223> OTHER INFORMATION: Synthetic

<400> SEQUENCE: 144

Gln Gln Ser Asn Ser Phe Pro Phe
1 5

<210> SEQ ID NO 145
<211> LENGTH: 366
<212> TYPE: DNA
<213> ORGANISM: Artificial Sequence
<220> FEATURE:
<223> OTHER INFORMATION: Synthetic

<400> SEQUENCE: 145
caggtgcagc tggtgcagtc tggggctgaa gtgaagaagc ctggggcctc agtgaaggtc 60
tcctgcaagg cttctggata caccttcacc ggccactata tgtactggat gcgacaggcc 120
cctggacaag ggcttgagtg gatgggatgg atcaacccta acagtggtgg cacaaactat 180
gcacagaagt ttcaggacag ggtcaccatg accagggaca cgtccatcag cacagcctac 240
atggagctga gcaggctgag atctgacgac acggccgtgt attactgtgc gagagggaga 300
tatggcagta gctggtacgg ggggtttgag tactggggcc agggaaccct ggtcaccgtc 360
tcctca 366

<210> SEQ ID NO 146
<211> LENGTH: 122
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly His
20 25 30

Tyr Met Tyr Trp Met Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Asp Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Arg Tyr Gly Ser Ser Trp Tyr Gly Gly Phe Glu Tyr Trp
100 105 110

Gly Gln Gly Thr Leu Val Thr Val Ser Ser
115 120

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggatacacct tcaccggcca ctat 24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Tyr Thr Phe Thr Gly His Tyr
1 5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
atcaacccta acagtggtgg caca 24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Asn Pro Asn Ser Gly Gly Thr
1 5

<210> SEQ ID NO 151
<211> LENGTH: 45
<212> TYPE: DNA
<213> ORGANISM: Artificial Sequence
<220> FEATURE:
<223> OTHER INFORMATION: Synthetic

<400> SEQUENCE: 151
gcgagaggga gatatggcag tagctggtac ggggggtttg agtac 45

<210> SEQ ID NO 152
<211> LENGTH: 15
<212> TYPE: PRT
<213> ORGANISM: Artificial Sequence
<220> FEATURE:
<223> OTHER INFORMATION: Synthetic

<400> SEQUENCE: 152

Ala Arg Gly Arg Tyr Gly Ser Ser Trp Tyr Gly Gly Phe Glu Tyr
1 5 10 15

<210> SEQ ID NO 153
<211> LENGTH: 321
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcttcc gtgtctgcat ctgttggaga cagagtcacc 60
atcacttgtc gggcgagtca gggtattacc agctggttag cctggtatca gcagaaacca 120
gggaaagccc ctaacctcct gatctatgct gcagccagtt tacaaagtgg ggtcccatca 180
aggttcagcg gcagtggatc tgggacggat ttcactctca ccatcagcag cctgcagcct 240
gaagacttta caacttacta ttgtcaacag gcttacagtc tccctctcac tttcggcgga 300
gggaccaagg tggagatcaa a 321

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Val Ser Ala Ser Val Gly
1 5 10 15

```
Asp Arg Val Thr Ile Thr Cys Arg Ala Ser Gln Gly Ile Thr Ser Trp
            20                  25                  30

Leu Ala Trp Tyr Gln Gln Lys Pro Gly Lys Ala Pro Asn Leu Leu Ile
        35                  40                  45

Tyr Ala Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Thr Thr Tyr Tyr Cys Gln Gln Ala Tyr Ser Leu Pro Leu
                85                  90                  95

Thr Phe Gly Gly Gly Thr Lys Val Glu Ile Lys
            100                 105


<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155

cagggtatta ccagctgg                                                   18


<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Gly Ile Thr Ser Trp
1               5


<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157

gctgcagcc                                                              9


<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Ala Ala Ala
1


<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
```

caacaggctt acagtctccc tctcact 27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Ala Tyr Ser Leu Pro Leu Thr
1 5

<210> SEQ ID NO 161
<211> LENGTH: 366
<212> TYPE: DNA
<213> ORGANISM: Artificial Sequence
<220> FEATURE:
<223> OTHER INFORMATION: Synthetic

<400> SEQUENCE: 161
caggtgcagc tggtggagtc tgggggaggc gtggtccagc ctgggaggtc cctgagactc 60
tcctgtgcag cctctggatt caccttcagt agctatggct tgcactgggt ccgccagtct 120
ccaggcaagg ggctggaatg ggtggcactt atatcatatg acggaagtaa taaatactat 180
gcagactccg tgaagggccg attcaccatc tccagagaca attccaagaa cacgctgtat 240
ctgcaaatga acagcctgag acctgaggac acggctggat atttctgtgc gaaatcccta 300
tatacaacca gctggtacgg gggctttgac tattggggcc agggaaccct ggtcaccgtc 360
tcctca 366

<210> SEQ ID NO 162
<211> LENGTH: 122
<212> TYPE: PRT
<213> ORGANISM: Artificial Sequence
<220> FEATURE:
<223> OTHER INFORMATION: Synthetic

<400> SEQUENCE: 162

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Leu His Trp Val Arg Gln Ser Pro Gly Lys Gly Leu Glu Trp Val
35 40 45

Ala Leu Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Pro Glu Asp Thr Ala Gly Tyr Phe Cys
85 90 95

Ala Lys Ser Leu Tyr Thr Thr Ser Trp Tyr Gly Gly Phe Asp Tyr Trp
100 105 110

Gly Gln Gly Thr Leu Val Thr Val Ser Ser
115 120

<210> SEQ ID NO 163
<211> LENGTH: 24
<212> TYPE: DNA
<213> ORGANISM: Artificial Sequence
<220> FEATURE:

<223> OTHER INFORMATION: Synthetic

<400> SEQUENCE: 163
ggattcacct tcagtagcta tggc 24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Thr Phe Ser Ser Tyr Gly
1 5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
atatcatatg acggaagtaa taaa 24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Ser Tyr Asp Gly Ser Asn Lys
1 5

<210> SEQ ID NO 167
<211> LENGTH: 45
<212> TYPE: DNA
<213> ORGANISM: Artificial Sequence
<220> FEATURE:
<223> OTHER INFORMATION: Synthetic

<400> SEQUENCE: 167
gcgaaatccc tatatacaac cagctggtac gggggctttg actat 45

<210> SEQ ID NO 168
<211> LENGTH: 15
<212> TYPE: PRT
<213> ORGANISM: Artificial Sequence
<220> FEATURE:
<223> OTHER INFORMATION: Synthetic

<400> SEQUENCE: 168

Ala Lys Ser Leu Tyr Thr Thr Ser Trp Tyr Gly Gly Phe Asp Tyr
1 5 10 15

<210> SEQ ID NO 169
<211> LENGTH: 321
<212> TYPE: DNA
<213> ORGANISM: Artificial Sequence
<220> FEATURE:
<223> OTHER INFORMATION: Synthetic

<400> SEQUENCE: 169

-continued

```
gacatccaga tgacccagtc tccatcttcc gtgtctgcat ctgtaggaga cagagtcacc     60

atcacttgtc gggcgagtca gggtattaga agctggttag cctggtatca gcaaaaacca    120

gggaaagccc ctaacctcct gatctatgct gcgtccagtt tgcaaagtgg ggtcccatca    180

aggttcagcg gcagtggatc tgggacagat ttcactctca ccatcagcag cctgcagcct    240

gaagattttg caacttacta ttgtcaacag gctaacagtt tccctcccac tttcggccct    300

gggaccaaag tggatatcaa a                                              321
```

```
<210> SEQ ID NO 170
<211> LENGTH: 107
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Pro Gly Thr Lys Val Asp Ile Lys
            100                 105


<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

cagggtatta gaagctgg                                                   18


<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Gly Ile Arg Ser Trp
1               5


<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173

gctgcgtcc                                                              9
```

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacaggcta acagtttccc tcccact 27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Ala Asn Ser Phe Pro Pro Thr
1 5

<210> SEQ ID NO 177
<211> LENGTH: 366
<212> TYPE: DNA
<213> ORGANISM: Artificial Sequence
<220> FEATURE:
<223> OTHER INFORMATION: Synthetic

<400> SEQUENCE: 177
gaggtgcagc tggtggagtc tgggggaggc ttggtacagc ctggggggtc cctgagactc 60
tcctgtgcag cctctgggtt caccttcagc aactatgcca tgacctgggt ccgccaggct 120
ccagggaagg ggctggagtg ggtctcaact atcagtggca gtggtgataa cacatactac 180
gcagactccg tgcagggccg gttcaccatc tccagaggcc attccaagaa cacgctgtat 240
ctgcaaatga acagcctgag agccgaggac acggccgtat attactgtgc gaaacctacg 300
tatagcagaa gctggtacgg tgcttttgat ttctggggcc aagggacaat ggtcaccgtc 360
tcttca 366

<210> SEQ ID NO 178
<211> LENGTH: 122
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

```
Ala Met Thr Trp Val Arg Gln Ala Pro Gly Lys Gly Leu Glu Trp Val
        35                  40                  45

Ser Thr Ile Ser Gly Ser Gly Asp Asn Thr Tyr Tyr Ala Asp Ser Val
    50                  55                  60

Gln Gly Arg Phe Thr Ile Ser Arg Gly His Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Thr Tyr Ser Arg Ser Trp Tyr Gly Ala Phe Asp Phe Trp
            100                 105                 110

Gly Gln Gly Thr Met Val Thr Val Ser Ser
        115                 120


<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179

gggttcacct tcagcaacta tgcc                                            24


<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Phe Thr Phe Ser Asn Tyr Ala
1               5


<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181

atcagtggca gtggtgataa caca                                            24


<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Gly Ser Gly Asp Asn Thr
1               5


<210> SEQ ID NO 183
<211> LENGTH: 45
<212> TYPE: DNA
<213> ORGANISM: Artificial Sequence
<220> FEATURE:
<223> OTHER INFORMATION: Synthetic

<400> SEQUENCE: 183

gcgaaaccta cgtatagcag aagctggtac ggtgcttttg atttc                     45
```

<210> SEQ ID NO 184
<211> LENGTH: 15
<212> TYPE: PRT
<213> ORGANISM: Artificial Sequence
<220> FEATURE:
<223> OTHER INFORMATION: Synthetic

<400> SEQUENCE: 184

```
Ala Lys Pro Thr Tyr Ser Arg Ser Trp Tyr Gly Ala Phe Asp Phe
1               5                   10                  15
```

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185

```
gacatccaga tgacccagtc tccatcctcc gtgtctgcat ctgtaggaga cagagtcacc     60

atcacttgtc gggcgagtca gggtattagc agctggttag cctggtatca gcagaaaccg    120

gggaaagccc ctcaactcct gatctatgct gcatccagat tgcaaagtgg ggtcccatca    180

aggttctggg gcagtggatc tgggacagat ttcactctca ccatcagcag cctgcagcct    240

gaagattttg caacttacta ttgtcaacag gctaacaatt tcccattcac tttcggccct    300

gggaccaaag tggatatcaa a                                              321
```

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Gln Leu Leu Ile
        35                  40                  45

Tyr Ala Ala Ser Arg Leu Gln Ser Gly Val Pro Ser Arg Phe Trp Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Phe
                85                  90                  95

Thr Phe Gly Pro Gly Thr Lys Val Asp Ile Lys
            100                 105
```

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187

```
cagggtatta gcagctgg                                                   18
```

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Gly Ile Ser Ser Trp
1 5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctgcatcc 9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacaggcta acaatttccc attcact 27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Ala Asn Asn Phe Pro Phe Thr
1 5

<210> SEQ ID NO 193
<211> LENGTH: 366
<212> TYPE: DNA
<213> ORGANISM: Artificial Sequence
<220> FEATURE:
<223> OTHER INFORMATION: Synthetic

<400> SEQUENCE: 193
caggttcagc tggtgcagtc tggagctgag gtgaagaagc ctggggcctc agtgaaggtc 60
tcctgcaagg cttctggtta cacctttacc agttatggta tcagctgggt gcgacaggcc 120
cctggacaag gccttgagtg gatgggatgg atccgcgctt acaatggtta cacaaactat 180

-continued

```
gcacagaagt ttcagggcag agtcaccatg accacagaca catccacgaa caccgcctac    240

atggagctga ggaccctgaa ttctgacgat acggccgttt attactgtgc gagagatcga    300

tatagtggga gcttccacgg taactttgac tactggggcc agggaaccct ggtcaccgtc    360

tcctca                                                               366


<210> SEQ ID NO 194
<211> LENGTH: 122
<212> TYPE: PRT
<213> ORGANISM: Artificial Sequence
<220> FEATURE:
<223> OTHER INFORMATION: Synthetic

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Arg Ala Tyr Asn Gly Tyr Thr Asn Tyr Ala Gln Lys Phe
    50                  55                  60

Gln Gly Arg Val Thr Met Thr Thr Asp Thr Ser Thr Asn Thr Ala Tyr
65                  70                  75                  80

Met Glu Leu Arg Thr Leu Asn Ser Asp Asp Thr Ala Val Tyr Tyr Cys
                85                  90                  95

Ala Arg Asp Arg Tyr Ser Gly Ser Phe His Gly Asn Phe Asp Tyr Trp
            100                 105                 110

Gly Gln Gly Thr Leu Val Thr Val Ser Ser
        115                 120


<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

ggttacacct ttaccagtta tggt                                            24


<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Tyr Thr Phe Thr Ser Tyr Gly
1               5


<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197

atccgcgctt acaatggtta caca                                            24
```

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Arg Ala Tyr Asn Gly Tyr Thr
1 5

<210> SEQ ID NO 199
<211> LENGTH: 45
<212> TYPE: DNA
<213> ORGANISM: Artificial Sequence
<220> FEATURE:
<223> OTHER INFORMATION: Synthetic

<400> SEQUENCE: 199
gcgagagatc gatatagtgg gagcttccac ggtaactttg actac 45

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Ala Arg Asp Arg Tyr Ser Gly Ser Phe His Gly Asn Phe Asp Tyr
1 5 10 15

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccatcttcc gtgtctgcgt ctgtaggaga cagagtgacc 60
atcacttgtc gggcgagtca gggtattttc agctggttag cctggtatca gcagaaacca 120
gggaaagccc ctaaggtcct aatctatgct gcatccaatt tggaaagtgg ggtcccatca 180
aggttcagcg gcagtggatc tgggacagat ttcactctca ccatcagcag cctgcagcct 240
gaagattttg caacttacta ttgtcaacag gctaacagtt taccgctcac tttcggcgga 300
gggaccaagg tggagatcaa a 321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Phe Ser Trp
20 25 30

Leu Ala Trp Tyr Gln Gln Lys Pro Gly Lys Ala Pro Lys Val Leu Ile
35 40 45

```
Tyr Ala Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Leu Pro Leu
                85                  90                  95

Thr Phe Gly Gly Gly Thr Lys Val Glu Ile Lys
            100                 105


<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203

cagggtattt tcagctgg                                                     18


<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Gly Ile Phe Ser Trp
1               5


<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205

gctgcatcc                                                                9


<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Ala Ala Ser
1


<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207

caacaggcta acagtttacc gctcact                                           27


<210> SEQ ID NO 208
<211> LENGTH: 9
<212> TYPE: PRT
<213> ORGANISM: Artificial Sequence
```

<220> FEATURE:
<223> OTHER INFORMATION: Synthetic

<400> SEQUENCE: 208

Gln Gln Ala Asn Ser Leu Pro Leu Thr
1               5

<210> SEQ ID NO 209
<211> LENGTH: 366
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ttggtccagc ctggggggtc cctgagactc 60
tcctgtgcag cctctggatt caccttcagt acctattcta tgcactgggt ccgccaggct 120
ccagggaagg gactggaata tgtttcaact attaataata atggggatac cacatattat 180
gcagactctg tgaagggcag attcaccatc tccagagaca attccaagaa cacgctgtat 240
cttcaactgg gcagcctgag acctgaggac atggctgtgt attactgtgc gagacagacg 300
tataccagca gctggtacgg ggggttcgac tcctggggcc agggaaccct ggtcaccgtc 360
tcctca 366

<210> SEQ ID NO 210
<211> LENGTH: 122
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ser Met His Trp Val Arg Gln Ala Pro Gly Lys Gly Leu Glu Tyr Val
        35                  40                  45

Ser Thr Ile Asn Asn Asn Gly Asp Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Leu Gly Ser Leu Arg Pro Glu Asp Met Ala Val Tyr Tyr Cys
                85                  90                  95

Ala Arg Gln Thr Tyr Thr Ser Ser Trp Tyr Gly Gly Phe Asp Ser Trp
            100                 105                 110

Gly Gln Gly Thr Leu Val Thr Val Ser Ser
        115                 120

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcacct tcagtaccta ttct 24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Thr Tyr Ser
1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attaataata atggggatac caca 24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Asn Asn Asn Gly Asp Thr Thr
1               5

<210> SEQ ID NO 215
<211> LENGTH: 45
<212> TYPE: DNA
<213> ORGANISM: Artificial Sequence
<220> FEATURE:
<223> OTHER INFORMATION: Synthetic

<400> SEQUENCE: 215
gcgagacaga cgtataccag cagctggtac ggggggttcg actcc 45

<210> SEQ ID NO 216
<211> LENGTH: 15
<212> TYPE: PRT
<213> ORGANISM: Artificial Sequence
<220> FEATURE:
<223> OTHER INFORMATION: Synthetic

<400> SEQUENCE: 216

Ala Arg Gln Thr Tyr Thr Ser Ser Trp Tyr Gly Gly Phe Asp Ser
1               5                   10                  15

<210> SEQ ID NO 217
<211> LENGTH: 321
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccatcttcc gtgtctgcat ctgtaggcga cagagtcacc 60
atcacttgtc gggcgagtca gggtattacc agctggttag cctggtatca gcagaaacca 120
gggaaagccc ctaaactcct gatctatgct gcatccaatt tgcaaagtgg ggtcccatca 180
aggttcagcg gcagtggatc tgggacagat ttcactctca ccatcaccag cctgcagcct 240
gaggattttg caacttacta ttgtcaacag gctaacagtc tcccattcac tttcggccct 300
gggaccaaag tggatatcaa a 321

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Thr Ser Trp
20 25 30

Leu Ala Trp Tyr Gln Gln Lys Pro Gly Lys Ala Pro Lys Leu Leu Ile
35 40 45

Tyr Ala Ala Ser Asn Leu Gln Ser Gly Val Pro Ser Arg Phe Ser Gly
50 55 60

Ser Gly Ser Gly Thr Asp Phe Thr Leu Thr Ile Thr Ser Leu Gln Pro
65 70 75 80

Glu Asp Phe Ala Thr Tyr Tyr Cys Gln Gln Ala Asn Ser Leu Pro Phe
85 90 95

Thr Phe Gly Pro Gly Thr Lys Val Asp Ile Lys
100 105

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
cagggtatta ccagctgg 18

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Gly Ile Thr Ser Trp
1 5

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 gctgcatcc 9

<210> SEQ ID NO 222
<211> LENGTH: 3
<212> TYPE: PRT
<213> ORGANISM: Artificial Sequence
<220> FEATURE:

<223> OTHER INFORMATION: Synthetic

<400> SEQUENCE: 222

Ala Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caacaggcta acagtctccc attcact 27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Ala Asn Ser Leu Pro Phe Thr
1 5

<210> SEQ ID NO 225
<211> LENGTH: 366
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtacagc ctggggggtc cctgagactc 60
tcctgtgcag cctctggatt caccettagc agctatgcca tgagctgggt ccgccaggct 120
ccagggaagg ggctggagtg ggtctcagct attagtggta gtggtggcag cacatactac 180
gcagactccg tgaagggccg gttcaccatc tccagagaca attccaagaa ctcgctgtat 240
ctgcaattga acagcctgag agccgaggac acggccgtat attactgtgc gaagacgctg 300
tatactacca gctggtacgg gggcttccag cactggggcc agggcaccct ggtcactgtc 360
tcctca 366

<210> SEQ ID NO 226
<211> LENGTH: 122
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Leu Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Ser Leu Tyr

```
65                  70                  75                  80

Leu Gln Leu Asn Ser Leu Arg Ala Glu Asp Thr Ala Val Tyr Tyr Cys
                85                  90                  95

Ala Lys Thr Leu Tyr Thr Thr Ser Trp Tyr Gly Gly Phe Gln His Trp
            100                 105                 110

Gly Gln Gly Thr Leu Val Thr Val Ser Ser
        115                 120


<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227

ggattcaccc ttagcagcta tgcc                                            24


<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Leu Ser Ser Tyr Ala
1               5


<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229

attagtggta gtggtggcag caca                                            24


<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Gly Ser Gly Gly Ser Thr
1               5


<210> SEQ ID NO 231
<211> LENGTH: 45
<212> TYPE: DNA
<213> ORGANISM: Artificial Sequence
<220> FEATURE:
<223> OTHER INFORMATION: Synthetic

<400> SEQUENCE: 231

gcgaagacgc tgtatactac cagctggtac gggggcttcc agcac                     45


<210> SEQ ID NO 232
<211> LENGTH: 15
<212> TYPE: PRT
<213> ORGANISM: Artificial Sequence
<220> FEATURE:
```

<223> OTHER INFORMATION: Synthetic

<400> SEQUENCE: 232

Ala Lys Thr Leu Tyr Thr Thr Ser Trp Tyr Gly Gly Phe Gln His
1 5 10 15

<210> SEQ ID NO 233
<211> LENGTH: 321
<212> TYPE: DNA
<213> ORGANISM: Artificial Sequence
<220> FEATURE:
<223> OTHER INFORMATION: Synthetic

<400> SEQUENCE: 233
gacatccaga tgacccagtc tccatcttcc gtgtctgcat ctataggaga cagagtcacc 60
atcacttgtc gggcgagtca gggaatcagc agttggttag cctggtatca gcagaaacca 120
gggaaagtcc ctaagctcct gatctatgct gcgtcctctt tgcaaagtgg gttcccatca 180
aggttcagcg gcagtggatc tgggacagat ttcactctca ccatcagtag cctgcagccc 240
gaagattttg caacttacta ttgtcaacag actcacagtt tcccgtggac ggtcggccaa 300
gggaccaagg tggaaatcaa a 321

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Ser Val Ser Ala Ser Ile Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Val Pro Lys Leu Leu Ile
35 40 45

Tyr Ala Ala Ser Ser Leu Gln Ser Gly Phe Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr His Ser Phe Pro Trp
85 90 95

Thr Val Gly Gln Gly Thr Lys Val Glu Ile Lys
100 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagggaatca gcagttgg 18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Gly Ile Ser Ser Trp
1 5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 gctgcgtcc 9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ala Ala Ser
1

<210> SEQ ID NO 239
<211> LENGTH: 24
<212> TYPE: DNA
<213> ORGANISM: Artificial Sequence
<220> FEATURE:
<223> OTHER INFORMATION: Synthetic

<400> SEQUENCE: 239
caacagactc acagtttccc gtgg 24

<210> SEQ ID NO 240
<211> LENGTH: 8
<212> TYPE: PRT
<213> ORGANISM: Artificial Sequence
<220> FEATURE:
<223> OTHER INFORMATION: Synthetic

<400> SEQUENCE: 240

Gln Gln Thr His Ser Phe Pro Trp
1 5

<210> SEQ ID NO 241
<211> LENGTH: 366
<212> TYPE: DNA
<213> ORGANISM: Artificial Sequence
<220> FEATURE:
<223> OTHER INFORMATION: Synthetic

<400> SEQUENCE: 241
gaggtgcagc tggtggagtc tgggggaggc ttggtacagc ctggggggtc cctgagactc 60
tcctgtgcag cctctggatt cacccttagg agctatttca tgacctgggt ccgccaggtt 120
ccagggaagg ggctggaggg ggtctcagct attagtggca ttagtggtgg cacatactac 180
acagactccg ttaagggccg gttcaccatc tccagagaca attccaagaa cacgctgttt 240
ctgcaaatga acagcctgag agccgaggac acggccgtat atttctgtgc gagaacggtg 300
tatagtagta gttactacgg gggcttccag cactggggcc agggcaccct ggtcaccgtc 360
tcctca 366

<210> SEQ ID NO 242
<211> LENGTH: 122
<212> TYPE: PRT
<213> ORGANISM: Artificial Sequence
<220> FEATURE:
<223> OTHER INFORMATION: Synthetic

<400> SEQUENCE: 242

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Phe Met Thr Trp Val Arg Gln Val Pro Gly Lys Gly Leu Glu Gly Val
        35                  40                  45

Ser Ala Ile Ser Gly Ile Ser Gly Gly Thr Tyr Tyr Thr Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Phe Cys
                85                  90                  95

Ala Arg Thr Val Tyr Ser Ser Ser Tyr Tyr Gly Gly Phe Gln His Trp
            100                 105                 110

Gly Gln Gly Thr Leu Val Thr Val Ser Ser
        115                 120
```

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243

```
ggattcaccc ttaggagcta tttc                                            24
```

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

```
Gly Phe Thr Leu Arg Ser Tyr Phe
1               5
```

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245

```
attagtggca ttagtggtgg caca                                            24
```

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Gly Ile Ser Gly Gly Thr
1 5

<210> SEQ ID NO 247
<211> LENGTH: 45
<212> TYPE: DNA
<213> ORGANISM: Artificial Sequence
<220> FEATURE:
<223> OTHER INFORMATION: Synthetic

<400> SEQUENCE: 247
gcgagaacgg tgtatagtag tagttactac gggggcttcc agcac 45

<210> SEQ ID NO 248
<211> LENGTH: 15
<212> TYPE: PRT
<213> ORGANISM: Artificial Sequence
<220> FEATURE:
<223> OTHER INFORMATION: Synthetic

<400> SEQUENCE: 248

Ala Arg Thr Val Tyr Ser Ser Ser Tyr Tyr Gly Gly Phe Gln His
1 5 10 15

<210> SEQ ID NO 249
<211> LENGTH: 321
<212> TYPE: DNA
<213> ORGANISM: Artificial Sequence
<220> FEATURE:
<223> OTHER INFORMATION: Synthetic

<400> SEQUENCE: 249
gacatccaga tgacccagtc tccatcttcc gtgtctgtat ctgtaggaga cagagtcacc 60
atcacttgtc gggcgagtca gggtattagc agttggttag cctggtatca gcagaaacca 120
gggaaagccc ctaagctcct gatctatgtt gcatccagtt tacaaagtgg ggtcccatca 180
aggttcagcg gcagtggatc tgggacagat ttcactctca ccatcagcag cctgcagcct 240
gaagattttg caacttacta ttgtcaacag actaacagtt tccctctcac tttcggcgga 300
gggaccaagg tggagatcaa a 321

<210> SEQ ID NO 250
<211> LENGTH: 107
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Val Ser Val Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Val Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Asn Ser Phe Pro Leu

```
                85                  90                  95

Thr Phe Gly Gly Gly Thr Lys Val Glu Ile Lys
            100                 105


<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251

cagggtatta gcagttgg                                                    18


<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Gly Ile Ser Ser Trp
1               5


<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253

gttgcatcc                                                               9


<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Val Ala Ser
1


<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255

caacagacta acagtttccc tctcact                                          27


<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Thr Asn Ser Phe Pro Leu Thr
1               5
```

<210> SEQ ID NO 257
<211> LENGTH: 366
<212> TYPE: DNA
<213> ORGANISM: Artificial Sequence
<220> FEATURE:
<223> OTHER INFORMATION: Synthetic

<400> SEQUENCE: 257

```
gaggtgcagc tggtggagtc tgggggaggc ttggtacagc ctggggggtc cctgagactc     60

tcctgtgcag cctctggatt cacccttagg agttatgtca tgtactgggt ccgccagggt    120

ccagggaagg ggctggaggg ggtctcaggt attagtggca gtagtggtgg cacatactac    180

acagactccg tgaagggccg gttcaccatc tccagagaca attccaagaa cacgctgttt    240

ctgcaaatga acagcctgag agccgaggac acggccgtat atttctgtgc gagatcggtg    300

tatagtacca cctggtacgg gggcttccag cactggggcc agggcaccct ggtcaccgtc    360

tcctca                                                               366
```

<210> SEQ ID NO 258
<211> LENGTH: 122
<212> TYPE: PRT
<213> ORGANISM: Artificial Sequence
<220> FEATURE:
<223> OTHER INFORMATION: Synthetic

<400> SEQUENCE: 258

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Arg Ser Tyr
            20                  25                  30

Val Met Tyr Trp Val Arg Gln Gly Pro Gly Lys Gly Leu Glu Gly Val
        35                  40                  45

Ser Gly Ile Ser Gly Ser Ser Gly Gly Thr Tyr Tyr Thr Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Phe Cys
                85                  90                  95

Ala Arg Ser Val Tyr Ser Thr Thr Trp Tyr Gly Gly Phe Gln His Trp
            100                 105                 110

Gly Gln Gly Thr Leu Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259

```
ggattcaccc ttaggagtta tgtc                                            24
```

<210> SEQ ID NO 260
<211> LENGTH: 8
<212> TYPE: PRT
<213> ORGANISM: Artificial Sequence
<220> FEATURE:
<223> OTHER INFORMATION: Synthetic -continued

<400> SEQUENCE: 260

Gly Phe Thr Leu Arg Ser Tyr Val
1 5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
attagtggca gtagtggtgg caca 24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Ser Gly Ser Ser Gly Gly Thr
1 5

<210> SEQ ID NO 263
<211> LENGTH: 45
<212> TYPE: DNA
<213> ORGANISM: Artificial Sequence
<220> FEATURE:
<223> OTHER INFORMATION: Synthetic

<400> SEQUENCE: 263
gcgagatcgg tgtatagtac cacctggtac gggggcttcc agcac 45

<210> SEQ ID NO 264
<211> LENGTH: 15
<212> TYPE: PRT
<213> ORGANISM: Artificial Sequence
<220> FEATURE:
<223> OTHER INFORMATION: Synthetic

<400> SEQUENCE: 264

Ala Arg Ser Val Tyr Ser Thr Thr Trp Tyr Gly Gly Phe Gln His
1 5 10 15

<210> SEQ ID NO 265
<211> LENGTH: 321
<212> TYPE: DNA
<213> ORGANISM: Artificial Sequence
<220> FEATURE:
<223> OTHER INFORMATION: Synthetic

<400> SEQUENCE: 265
gacatccaga tgacccagtc tccatcttcc gtgtctgtat ctgtgggaga cagagtcacc 60
atcacttgtc gggcgagtca ggttattagc agttggttag cctggtatca gctgaaacca 120
gggaaagccc ctaaactcct gatctatgct gcatccagtt tacaaagtgg ggtcccatca 180
aggttcagcg gcagtggatc tgggacagat ttcactctca ccatcagcgg cctgcagcct 240
gaagattttg cagtttacta ttgtcaacag actaacagtt tccctctcac tttcggcgga 300
gggaccaagg tggagatcaa a 321

<210> SEQ ID NO 266

```
<211> LENGTH: 107
<212> TYPE: PRT
<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Ser Val Ser Val Ser Val Gly
1               5                   10                  15

Asp Arg Val Thr Ile Thr Cys Arg Ala Ser Gln Val Ile Ser Ser Trp
            20                  25                  30

Leu Ala Trp Tyr Gln Leu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Gly Leu Gln Pro
65                  70                  75                  80

Glu Asp Phe Ala Val Tyr Tyr Cys Gln Gln Thr Asn Ser Phe Pro Leu
                85                  90                  95

Thr Phe Gly Gly Gly Thr Lys Val Glu Ile Lys
            100                 105


<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267

caggttatta gcagttgg                                                 18


<210> SEQ ID NO 268
<211> LENGTH: 6
<212> TYPE: PRT
<213> ORGANISM: Artificial Sequence
<220> FEATURE:
<223> OTHER INFORMATION: Synthetic

<400> SEQUENCE: 268

Gln Val Ile Ser Ser Trp
1               5


<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269

gctgcatcc                                                            9


<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Ala Ala Ser
1
```

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
caacagacta acagtttccc tctcact 27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Thr Asn Ser Phe Pro Leu Thr
1 5

<210> SEQ ID NO 273
<211> LENGTH: 366
<212> TYPE: DNA
<213> ORGANISM: Artificial Sequence
<220> FEATURE:
<223> OTHER INFORMATION: Synthetic

<400> SEQUENCE: 273
gaggtgcagc tggtggagtc tggggaaac ttggaacagc ctggggggtc ccttagactc 60
tcctgtacag cctctggatt cacctttagc agatctgcca tgaactgggt ccgccgggct 120
ccagggaagg ggctggagtg ggtctcagga attagtggta gtggtggtcg aacatactac 180
gcagactccg tgaagggccg gttcaccatc tccagagaca attccaagaa tacgctatat 240
ctgcaaatga acagcctgag cgccgaggac acggccgcat attactgtgc gaaagattcg 300
tatactacca gttggtacgg aggtatggac gtctggggcc acgggaccac ggtcaccgtc 360
tcctca 366

<210> SEQ ID NO 274
<211> LENGTH: 122
<212> TYPE: PRT
<213> ORGANISM: Artificial Sequence
<220> FEATURE:
<223> OTHER INFORMATION: Synthetic

<400> SEQUENCE: 274

Glu Val Gln Leu Val Glu Ser Gly Gly Asn Leu Glu Gln Pro Gly Gly
1 5 10 15

Ser Leu Arg Leu Ser Cys Thr Ala Ser Gly Phe Thr Phe Ser Arg Ser
20 25 30

Ala Met Asn Trp Val Arg Arg Ala Pro Gly Lys Gly Leu Glu Trp Val
35 40 45

Ser Gly Ile Ser Gly Ser Gly Gly Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Ser Ala Glu Asp Thr Ala Ala Tyr Tyr Cys
85 90 95

Ala Lys Asp Ser Tyr Thr Thr Ser Trp Tyr Gly Gly Met Asp Val Trp
100 105 110

Gly His Gly Thr Thr Val Thr Val Ser Ser
115 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggattcacct ttagcagatc tgcc 24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Ser Arg Ser Ala
1 5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
attagtggta gtggtggtcg aaca 24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Ser Gly Ser Gly Gly Arg Thr
1 5

<210> SEQ ID NO 279
<211> LENGTH: 45
<212> TYPE: DNA
<213> ORGANISM: Artificial Sequence
<220> FEATURE:
<223> OTHER INFORMATION: Synthetic

<400> SEQUENCE: 279
gcgaaagatt cgtatactac cagttggtac ggaggtatgg acgtc 45

<210> SEQ ID NO 280
<211> LENGTH: 15
<212> TYPE: PRT
<213> ORGANISM: Artificial Sequence
<220> FEATURE:
<223> OTHER INFORMATION: Synthetic

<400> SEQUENCE: 280

Ala Lys Asp Ser Tyr Thr Thr Ser Trp Tyr Gly Gly Met Asp Val
1 5 10 15

<210> SEQ ID NO 281
<211> LENGTH: 321
<212> TYPE: DNA
<213> ORGANISM: Artificial Sequence
<220> FEATURE:
<223> OTHER INFORMATION: Synthetic

<400> SEQUENCE: 281
gacatccaga tgacccagtc tccatcttcc gtgtctgcat ctgtaggaga cagagtcacc 60
atcacttgtc gggcgagtca gggtattttc agctggttag cctggtatca gcagaaacca 120
ggaaaagccc ctaagctcct gatctatgct gcttccagtt tacaaagtgg ggtcccatca 180
agattcagcg gcagtggatc tgggacagat ttcactctca ccatcagcag cctgcagcct 240
gaggattttg caatttacta ttgtcaacag gctaacagtg tcccgatcac cttcggccaa 300
gggacacgac tggagattaa a 321

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Phe Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Gln Gln Ala Asn Ser Val Pro Ile
85 90 95

Thr Phe Gly Gln Gly Thr Arg Leu Glu Ile Lys
100 105

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283
cagggtattt tcagctgg 18

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

Gln Gly Ile Phe Ser Trp
1 5

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 gctgcttcc 9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Ala Ala Ser
1

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacaggcta acagtgtccc gatcacc 27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Ala Asn Ser Val Pro Ile Thr
1 5

<210> SEQ ID NO 289
<211> LENGTH: 366
<212> TYPE: DNA
<213> ORGANISM: Artificial Sequence
<220> FEATURE:
<223> OTHER INFORMATION: Synthetic

<400> SEQUENCE: 289
gaggtgcagc tggtggagtc tgggggaggc ttggtacagc ctggggggtc cctgagactc 60
tcctgttcag cctctggatt cacctttagc agctatgcca tgaactgggt ccgccaggct 120
ccagggaagg ggctggagtg ggtcaccgct attagtggca gtggtggtgg cacatactac 180
gcagactccg tgaagggccg gttcaccatc tccagagaca attccaagaa ctcgctgttt 240
ctgcaattga acagcctgag agccgaggac acggccgtgt attactgtgc gaaacaaacg 300
tataccagca gctggtacgg tggctttgat atctggggcc aggggacaat ggtcaccgtc 360
tcttca 366

<210> SEQ ID NO 290
<211> LENGTH: 122
<212> TYPE: PRT
<213> ORGANISM: Artificial Sequence
<220> FEATURE:

<223> OTHER INFORMATION: Synthetic

<400> SEQUENCE: 290

Glu Val Gln Leu Val Glu Ser Gly Gly Gly Leu Val Gln Pro Gly Gly
1 5 10 15

Ser Leu Arg Leu Ser Cys Ser Ala Ser Gly Phe Thr Phe Ser Ser Tyr
20 25 30

Ala Met Asn Trp Val Arg Gln Ala Pro Gly Lys Gly Leu Glu Trp Val
35 40 45

Thr Ala Ile Ser Gly Ser Gly Gly Gly Thr Tyr Tyr Ala Asp Ser Val
50 55 60

Lys Gly Arg Phe Thr Ile Ser Arg Asp Asn Ser Lys Asn Ser Leu Phe
65 70 75 80

Leu Gln Leu Asn Ser Leu Arg Ala Glu Asp Thr Ala Val Tyr Tyr Cys
85 90 95

Ala Lys Gln Thr Tyr Thr Ser Ser Trp Tyr Gly Gly Phe Asp Ile Trp
100 105 110

Gly Gln Gly Thr Met Val Thr Val Ser Ser
115 120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct ttagcagcta tgcc 24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Ser Ser Tyr Ala
1 5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagtggca gtggtggtgg caca 24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Gly Ser Gly Gly Gly Thr
1 5

<210> SEQ ID NO 295
<211> LENGTH: 45
<212> TYPE: DNA
<213> ORGANISM: Artificial Sequence
<220> FEATURE:
<223> OTHER INFORMATION: Synthetic

<400> SEQUENCE: 295
gcgaaacaaa cgtataccag cagctggtac ggtggctttg atatc 45

<210> SEQ ID NO 296
<211> LENGTH: 15
<212> TYPE: PRT
<213> ORGANISM: Artificial Sequence
<220> FEATURE:
<223> OTHER INFORMATION: Synthetic

<400> SEQUENCE: 296

Ala Lys Gln Thr Tyr Thr Ser Ser Trp Tyr Gly Gly Phe Asp Ile
1 5 10 15

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccaga tgacccagtc gccatcttcc gtgtccgcgt ctgtaggaga cagagtcacc 60
atcacttgtc gggcgagtca gggttttagt tcctggttag cctggtatca gcagatacca 120
gggaaagccc ccaagctcct gatctatgct gcatcaaggt tgcaaagtgg ggtcccatcc 180
aggttccgcg gcagtggatc tgggacagat ttcactctca ccatcagcag cctgcagcct 240
gaggattttg caacttacta ttgtcaacag gctaacagtt tcccgctcac tttcggcgga 300
gggaccaagg tggagatcaa a 321

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Phe Ser Ser Trp
20 25 30

Leu Ala Trp Tyr Gln Gln Ile Pro Gly Lys Ala Pro Lys Leu Leu Ile
35 40 45

Tyr Ala Ala Ser Arg Leu Gln Ser Gly Val Pro Ser Arg Phe Arg Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Leu
85 90 95

Thr Phe Gly Gly Gly Thr Lys Val Glu Ile Lys
100 105

<210> SEQ ID NO 299

<211> LENGTH: 18
<212> TYPE: DNA
<213> ORGANISM: Artificial Sequence
<220> FEATURE:
<223> OTHER INFORMATION: Synthetic

<400> SEQUENCE: 299
cagggtttta gttcctgg 18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Gly Phe Ser Ser Trp
1 5

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gctgcatca 9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacaggcta acagtttccc gctcact 27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Ala Asn Ser Phe Pro Leu Thr
1 5

<210> SEQ ID NO 305
<211> LENGTH: 167
<212> TYPE: PRT
<213> ORGANISM: Artificial Sequence
<220> FEATURE:

<223> OTHER INFORMATION: Synthetic

<400> SEQUENCE: 305

```
Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
        35                  40                  45

Leu Leu Ser Tyr Tyr Glu Ser Gln His Pro Ser Ser Glu Ser Gly Asp
    50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
            100                 105                 110

Ser Phe Asn Cys Val Ser Phe Glu Cys Lys Thr Asp Pro Gly Val Phe
        115                 120                 125

Ile Gly Val Lys Asp Asn His Leu Ala Leu Ile Lys Val Asp Tyr Ser
    130                 135                 140

Glu Asn Leu Gly Ser Glu Asn Ile Leu Phe Lys Leu Ser Glu Ile Leu
145                 150                 155                 160

Glu His His His His His His
                165
```

<210> SEQ ID NO 306
<211> LENGTH: 167
<212> TYPE: PRT
<213> ORGANISM: Artificial Sequence
<220> FEATURE:
<223> OTHER INFORMATION: Synthetic

<400> SEQUENCE: 306

```
Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
        35                  40                  45

Leu Leu Ser Tyr Tyr Glu Ser Gln His Pro Ser Ser Glu Ser Gly Asp
    50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
            100                 105                 110

Ser Phe Asn Cys Val Ser Phe Glu Cys Lys Thr Asp Pro Gly Val Phe
        115                 120                 125

Ile Gly Val Lys Asp Asn His Leu Ala Leu Ile Lys Val Asp Tyr Ser
    130                 135                 140

Glu Asn Leu Gly Ser Glu Asn Ile Leu Phe Lys Leu Ser Glu Ile Leu
145                 150                 155                 160

Glu His His His His His His
                165
```

<210> SEQ ID NO 307
<211> LENGTH: 354
<212> TYPE: DNA
<213> ORGANISM: Artificial Sequence
<220> FEATURE:
<223> OTHER INFORMATION: Synthetic

<400> SEQUENCE: 307
caggtcacct tgaaggagtc tggtcctgtg ctggtgaaac ccacagagag cctcacgctg 60
acctgctccg tctctggatt ctcactcagt aatgttagaa tgggtgtgag ctggatccgt 120
cagtccccag ggaaggccct ggagtggctt gcacacattt tttcgaatga cgaaaaatcc 180
tacaccacat ctctgaagac caggctcacc atctccaagg acacctccag aagccaggtg 240
gtccttacca tgaccgacat ggaccctggg gacacagcca catattactg tgcacggata 300
cggaatttgg cctttaatta ctggggccag ggaaccctgg tcaccgtctc ctca 354

<210> SEQ ID NO 308
<211> LENGTH: 118
<212> TYPE: PRT
<213> ORGANISM: Artificial Sequence
<220> FEATURE:
<223> OTHER INFORMATION: Synthetic

<400> SEQUENCE: 308

Gln Val Thr Leu Lys Glu Ser Gly Pro Val Leu Val Lys Pro Thr Glu
1               5                   10                  15

Ser Leu Thr Leu Thr Cys Ser Val Ser Gly Phe Ser Leu Ser Asn Val
            20                  25                  30

Arg Met Gly Val Ser Trp Ile Arg Gln Ser Pro Gly Lys Ala Leu Glu
        35                  40                  45

Trp Leu Ala His Ile Phe Ser Asn Asp Glu Lys Ser Tyr Thr Thr Ser
    50                  55                  60

Leu Lys Thr Arg Leu Thr Ile Ser Lys Asp Thr Ser Arg Ser Gln Val
65                  70                  75                  80

Val Leu Thr Met Thr Asp Met Asp Pro Gly Asp Thr Ala Thr Tyr Tyr
                85                  90                  95

Cys Ala Arg Ile Arg Asn Leu Ala Phe Asn Tyr Trp Gly Gln Gly Thr
            100                 105                 110

Leu Val Thr Val Ser Ser
        115

<210> SEQ ID NO 309
<211> LENGTH: 30
<212> TYPE: DNA
<213> ORGANISM: Artificial Sequence
<220> FEATURE:
<223> OTHER INFORMATION: Synthetic

<400> SEQUENCE: 309
ggattctcac tcagtaatgt tagaatgggt 30

<210> SEQ ID NO 310
<211> LENGTH: 10
<212> TYPE: PRT
<213> ORGANISM: Artificial Sequence
<220> FEATURE:
<223> OTHER INFORMATION: Synthetic

<400> SEQUENCE: 310

Gly Phe Ser Leu Ser Asn Val Arg Met Gly
1 5 10

<210> SEQ ID NO 311
<211> LENGTH: 21
<212> TYPE: DNA
<213> ORGANISM: Artificial Sequence
<220> FEATURE:
<223> OTHER INFORMATION: Synthetic

<400> SEQUENCE: 311 atttttcga atgacgaaaa a 21

<210> SEQ ID NO 312
<211> LENGTH: 7
<212> TYPE: PRT
<213> ORGANISM: Artificial Sequence
<220> FEATURE:
<223> OTHER INFORMATION: Synthetic

<400> SEQUENCE: 312

Ile Phe Ser Asn Asp Glu Lys
1 5

<210> SEQ ID NO 313
<211> LENGTH: 30
<212> TYPE: DNA
<213> ORGANISM: Artificial Sequence
<220> FEATURE:
<223> OTHER INFORMATION: Synthetic

<400> SEQUENCE: 313
gcacggatac ggaatttggc ctttaattac 30

<210> SEQ ID NO 314
<211> LENGTH: 10
<212> TYPE: PRT
<213> ORGANISM: Artificial Sequence
<220> FEATURE:
<223> OTHER INFORMATION: Synthetic

<400> SEQUENCE: 314

Ala Arg Ile Arg Asn Leu Ala Phe Asn Tyr
1 5 10

<210> SEQ ID NO 315
<211> LENGTH: 339
<212> TYPE: DNA
<213> ORGANISM: Artificial Sequence
<220> FEATURE:
<223> OTHER INFORMATION: Synthetic

<400> SEQUENCE: 315
gacttcgtga tgacccagtc tccagactcc ctggctgtgt ctctgggcga gagggccacc 60
atcaactgca agtccagcca gagtgtgtta cacaggtcca gcaataagaa ctacttagct 120
tggtatcagc agaagccagg acagcctcct aacctgctca tttactgggc atctacccgg 180
gaatccgggg tccctgaccg attcagtggc agcgggtctg ggacagattt cactctcacc 240
atcagcagcc tgcaggctga agatgtggca gtttattact gtcagcaata ttatggtact 300
ctatttactt tcggccctgg gaccaaagtg gatatcaaa 339

<210> SEQ ID NO 316
<211> LENGTH: 113
<212> TYPE: PRT

<213> ORGANISM: Artificial Sequence
<220> FEATURE:
<223> OTHER INFORMATION: Synthetic

<400> SEQUENCE: 316

Asp Phe Val Met Thr Gln Ser Pro Asp Ser Leu Ala Val Ser Leu Gly
1 5 10 15

Glu Arg Ala Thr Ile Asn Cys Lys Ser Ser Gln Ser Val Leu His Arg
20 25 30

Ser Ser Asn Lys Asn Tyr Leu Ala Trp Tyr Gln Gln Lys Pro Gly Gln
35 40 45

Pro Pro Asn Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Gly Thr Leu Phe Thr Phe Gly Pro Gly Thr Lys Val Asp Ile
100 105 110

Lys

<210> SEQ ID NO 317
<211> LENGTH: 36
<212> TYPE: DNA
<213> ORGANISM: Artificial Sequence
<220> FEATURE:
<223> OTHER INFORMATION: Synthetic

<400> SEQUENCE: 317
cagagtgtgt tacacaggtc cagcaataag aactac 36

<210> SEQ ID NO 318
<211> LENGTH: 12
<212> TYPE: PRT
<213> ORGANISM: Artificial Sequence
<220> FEATURE:
<223> OTHER INFORMATION: Synthetic

<400> SEQUENCE: 318

Gln Ser Val Leu His Arg Ser Ser Asn Lys Asn Tyr
1 5 10

<210> SEQ ID NO 319
<211> LENGTH: 9
<212> TYPE: DNA
<213> ORGANISM: Artificial Sequence
<220> FEATURE:
<223> OTHER INFORMATION: Synthetic

<400> SEQUENCE: 319 tgggcatct 9

<210> SEQ ID NO 320
<211> LENGTH: 3
<212> TYPE: PRT
<213> ORGANISM: Artificial Sequence
<220> FEATURE:
<223> OTHER INFORMATION: Synthetic

<400> SEQUENCE: 320

Trp Ala Ser
1

<210> SEQ ID NO 321
<211> LENGTH: 27
<212> TYPE: DNA
<213> ORGANISM: Artificial Sequence
<220> FEATURE:
<223> OTHER INFORMATION: Synthetic

<400> SEQUENCE: 321
cagcaatatt atggtactct atttact 27

<210> SEQ ID NO 322
<211> LENGTH: 9
<212> TYPE: PRT
<213> ORGANISM: Artificial Sequence
<220> FEATURE:
<223> OTHER INFORMATION: Synthetic

<400> SEQUENCE: 322

Gln Gln Tyr Tyr Gly Thr Leu Phe Thr
1 5

<210> SEQ ID NO 323
<211> LENGTH: 537
<212> TYPE: PRT
<213> ORGANISM: Artificial Sequence
<220> FEATURE:
<223> OTHER INFORMATION: hST2-hFc

<400> SEQUENCE: 323

Lys Phe Ser Lys Gln Ser Trp Gly Leu Glu Asn Glu Ala Leu Ile Val
1 5 10 15

Arg Cys Pro Arg Gln Gly Lys Pro Ser Tyr Thr Val Asp Trp Tyr Tyr
20 25 30

Ser Gln Thr Asn Lys Ser Ile Pro Thr Gln Glu Arg Asn Arg Val Phe
35 40 45

Ala Ser Gly Gln Leu Leu Lys Phe Leu Pro Ala Ala Val Ala Asp Ser
50 55 60

Gly Ile Tyr Thr Cys Ile Val Arg Ser Pro Thr Phe Asn Arg Thr Gly
65 70 75 80

Tyr Ala Asn Val Thr Ile Tyr Lys Lys Gln Ser Asp Cys Asn Val Pro
85 90 95

Asp Tyr Leu Met Tyr Ser Thr Val Ser Gly Ser Glu Lys Asn Ser Lys
100 105 110

Ile Tyr Cys Pro Thr Ile Asp Leu Tyr Asn Trp Thr Ala Pro Leu Glu
115 120 125

Trp Phe Lys Asn Cys Gln Ala Leu Gln Gly Ser Arg Tyr Arg Ala His
130 135 140

Lys Ser Phe Leu Val Ile Asp Asn Val Met Thr Glu Asp Ala Gly Asp
145 150 155 160

Tyr Thr Cys Lys Phe Ile His Asn Glu Asn Gly Ala Asn Tyr Ser Val
165 170 175

Thr Ala Thr Arg Ser Phe Thr Val Lys Asp Glu Gln Gly Phe Ser Leu
180 185 190

Phe Pro Val Ile Gly Ala Pro Ala Gln Asn Glu Ile Lys Glu Val Glu
195 200 205

Ile Gly Lys Asn Ala Asn Leu Thr Cys Ser Ala Cys Phe Gly Lys Gly
210 215 220

Thr Gln Phe Leu Ala Ala Val Leu Trp Gln Leu Asn Gly Thr Lys Ile
225 230 235 240

```
Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
        275                 280                 285

Asn Leu His Gly Leu Arg Arg His Thr Val Arg Leu Ser Arg Lys Asn
    290                 295                 300

Pro Ile Asp His His Ser Asp Lys Thr His Thr Cys Pro Pro Cys Pro
305                 310                 315                 320

Ala Pro Glu Leu Leu Gly Gly Pro Ser Val Phe Leu Phe Pro Pro Lys
                325                 330                 335

Pro Lys Asp Thr Leu Met Ile Ser Arg Thr Pro Glu Val Thr Cys Val
            340                 345                 350

Val Val Asp Val Ser His Glu Asp Pro Glu Val Lys Phe Asn Trp Tyr
        355                 360                 365

Val Asp Gly Val Glu Val His Asn Ala Lys Thr Lys Pro Arg Glu Glu
    370                 375                 380

Gln Tyr Asn Ser Thr Tyr Arg Val Val Ser Val Leu Thr Val Leu His
385                 390                 395                 400

Gln Asp Trp Leu Asn Gly Lys Glu Tyr Lys Cys Lys Val Ser Asn Lys
                405                 410                 415

Ala Leu Pro Ala Pro Ile Glu Lys Thr Ile Ser Lys Ala Lys Gly Gln
            420                 425                 430

Pro Arg Glu Pro Gln Val Tyr Thr Leu Pro Pro Ser Arg Asp Glu Leu
        435                 440                 445

Thr Lys Asn Gln Val Ser Leu Thr Cys Leu Val Lys Gly Phe Tyr Pro
    450                 455                 460

Ser Asp Ile Ala Val Glu Trp Glu Ser Asn Gly Gln Pro Glu Asn Asn
465                 470                 475                 480

Tyr Lys Thr Thr Pro Pro Val Leu Asp Ser Asp Gly Ser Phe Phe Leu
                485                 490                 495

Tyr Ser Lys Leu Thr Val Asp Lys Ser Arg Trp Gln Gln Gly Asn Val
            500                 505                 510

Phe Ser Cys Ser Val Met His Glu Ala Leu His Asn His Tyr Thr Gln
        515                 520                 525

Lys Ser Leu Ser Leu Ser Pro Gly Lys
    530                 535


<210> SEQ ID NO 324
<211> LENGTH: 543
<212> TYPE: PRT
<213> ORGANISM: Artificial Sequence
<220> FEATURE:
<223> OTHER INFORMATION: hST2-mFc

<400> SEQUENCE: 324

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60
```

Gly Ile Tyr Thr Cys Ile Val Arg Ser Pro Thr Phe Asn Arg Thr Gly
65 70 75 80

Tyr Ala Asn Val Thr Ile Tyr Lys Lys Gln Ser Asp Cys Asn Val Pro
85 90 95

Asp Tyr Leu Met Tyr Ser Thr Val Ser Gly Ser Glu Lys Asn Ser Lys
100 105 110

Ile Tyr Cys Pro Thr Ile Asp Leu Tyr Asn Trp Thr Ala Pro Leu Glu
115 120 125

Trp Phe Lys Asn Cys Gln Ala Leu Gln Gly Ser Arg Tyr Arg Ala His
130 135 140

Lys Ser Phe Leu Val Ile Asp Asn Val Met Thr Glu Asp Ala Gly Asp
145 150 155 160

Tyr Thr Cys Lys Phe Ile His Asn Glu Asn Gly Ala Asn Tyr Ser Val
165 170 175

Thr Ala Thr Arg Ser Phe Thr Val Lys Asp Glu Gln Gly Phe Ser Leu
180 185 190

Phe Pro Val Ile Gly Ala Pro Ala Gln Asn Glu Ile Lys Glu Val Glu
195 200 205

Ile Gly Lys Asn Ala Asn Leu Thr Cys Ser Ala Cys Phe Gly Lys Gly
210 215 220

Thr Gln Phe Leu Ala Ala Val Leu Trp Gln Leu Asn Gly Thr Lys Ile
225 230 235 240

Thr Asp Phe Gly Glu Pro Arg Ile Gln Gln Glu Glu Gly Gln Asn Gln
245 250 255

Ser Phe Ser Asn Gly Leu Ala Cys Leu Asp Met Val Leu Arg Ile Ala
260 265 270

Asp Val Lys Glu Glu Asp Leu Leu Leu Gln Tyr Asp Cys Leu Ala Leu
275 280 285

Asn Leu His Gly Leu Arg Arg His Thr Val Arg Leu Ser Arg Lys Asn
290 295 300

Pro Ile Asp His His Ser Glu Pro Arg Gly Pro Thr Ile Lys Pro Cys
305 310 315 320

Pro Pro Cys Lys Cys Pro Ala Pro Asn Leu Leu Gly Gly Pro Ser Val
325 330 335

Phe Ile Phe Pro Pro Lys Ile Lys Asp Val Leu Met Ile Ser Leu Ser
340 345 350

Pro Ile Val Thr Cys Val Val Val Asp Val Ser Glu Asp Asp Pro Asp
355 360 365

Val Gln Ile Ser Trp Phe Val Asn Asn Val Glu Val His Thr Ala Gln
370 375 380

Thr Gln Thr His Arg Glu Asp Tyr Asn Ser Thr Leu Arg Val Val Ser
385 390 395 400

Ala Leu Pro Ile Gln His Gln Asp Trp Met Ser Gly Lys Glu Phe Lys
405 410 415

Cys Lys Val Asn Asn Lys Asp Leu Pro Ala Pro Ile Glu Arg Thr Ile
420 425 430

Ser Lys Pro Lys Gly Ser Val Arg Ala Pro Gln Val Tyr Val Leu Pro
435 440 445

Pro Pro Glu Glu Glu Met Thr Lys Lys Gln Val Thr Leu Thr Cys Met
450 455 460

Val Thr Asp Phe Met Pro Glu Asp Ile Tyr Val Glu Trp Thr Asn Asn
465 470 475 480

```
Gly Lys Thr Glu Leu Asn Tyr Lys Asn Thr Glu Pro Val Leu Asp Ser
                485                 490                 495

Asp Gly Ser Tyr Phe Met Tyr Ser Lys Leu Arg Val Glu Lys Lys Asn
            500                 505                 510

Trp Val Glu Arg Asn Ser Tyr Ser Cys Ser Val Val His Glu Gly Leu
        515                 520                 525

His Asn His His Thr Thr Lys Ser Phe Ser Arg Thr Pro Gly Lys
    530                 535                 540


<210> SEQ ID NO 325
<211> LENGTH: 884
<212> TYPE: PRT
<213> ORGANISM: Artificial Sequence
<220> FEATURE:
<223> OTHER INFORMATION: hST2-hIL1RAcP-mFc

<400> SEQUENCE: 325

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
    210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
        275                 280                 285

Asn Leu His Gly Leu Arg Arg His Thr Val Arg Leu Ser Arg Lys Asn
    290                 295                 300
```

Pro Ile Asp His His Ser Ser Glu Arg Cys Asp Asp Trp Gly Leu Asp
305 310 315 320

Thr Met Arg Gln Ile Gln Val Phe Glu Asp Glu Pro Ala Arg Ile Lys
325 330 335

Cys Pro Leu Phe Glu His Phe Leu Lys Phe Asn Tyr Ser Thr Ala His
340 345 350

Ser Ala Gly Leu Thr Leu Ile Trp Tyr Trp Thr Arg Gln Asp Arg Asp
355 360 365

Leu Glu Glu Pro Ile Asn Phe Arg Leu Pro Glu Asn Arg Ile Ser Lys
370 375 380

Glu Lys Asp Val Leu Trp Phe Arg Pro Thr Leu Leu Asn Asp Thr Gly
385 390 395 400

Asn Tyr Thr Cys Met Leu Arg Asn Thr Thr Tyr Cys Ser Lys Val Ala
405 410 415

Phe Pro Leu Glu Val Val Gln Lys Asp Ser Cys Phe Asn Ser Pro Met
420 425 430

Lys Leu Pro Val His Lys Leu Tyr Ile Glu Tyr Gly Ile Gln Arg Ile
435 440 445

Thr Cys Pro Asn Val Asp Gly Tyr Phe Pro Ser Ser Val Lys Pro Thr
450 455 460

Ile Thr Trp Tyr Met Gly Cys Tyr Lys Ile Gln Asn Phe Asn Asn Val
465 470 475 480

Ile Pro Glu Gly Met Asn Leu Ser Phe Leu Ile Ala Leu Ile Ser Asn
485 490 495

Asn Gly Asn Tyr Thr Cys Val Val Thr Tyr Pro Glu Asn Gly Arg Thr
500 505 510

Phe His Leu Thr Arg Thr Leu Thr Val Lys Val Val Gly Ser Pro Lys
515 520 525

Asn Ala Val Pro Pro Val Ile His Ser Pro Asn Asp His Val Val Tyr
530 535 540

Glu Lys Glu Pro Gly Glu Glu Leu Leu Ile Pro Cys Thr Val Tyr Phe
545 550 555 560

Ser Phe Leu Met Asp Ser Arg Asn Glu Val Trp Trp Thr Ile Asp Gly
565 570 575

Lys Lys Pro Asp Asp Ile Thr Ile Asp Val Thr Ile Asn Glu Ser Ile
580 585 590

Ser His Ser Arg Thr Glu Asp Glu Thr Arg Thr Gln Ile Leu Ser Ile
595 600 605

Lys Lys Val Thr Ser Glu Asp Leu Lys Arg Ser Tyr Val Cys His Ala
610 615 620

Arg Ser Ala Lys Gly Glu Val Ala Lys Ala Ala Lys Val Lys Gln Lys
625 630 635 640

Val Pro Ala Pro Arg Tyr Thr Val Glu Ser Gly Glu Pro Arg Gly Pro
645 650 655

Thr Ile Lys Pro Cys Pro Pro Cys Lys Cys Pro Ala Pro Asn Leu Leu
660 665 670

Gly Gly Pro Ser Val Phe Ile Phe Pro Pro Lys Ile Lys Asp Val Leu
675 680 685

Met Ile Ser Leu Ser Pro Ile Val Thr Cys Val Val Val Asp Val Ser
690 695 700

Glu Asp Asp Pro Asp Val Gln Ile Ser Trp Phe Val Asn Asn Val Glu
705 710 715 720

Val His Thr Ala Gln Thr Gln Thr His Arg Glu Asp Tyr Asn Ser Thr

```
                725                 730                 735

Leu Arg Val Val Ser Ala Leu Pro Ile Gln His Gln Asp Trp Met Ser
            740                 745                 750

Gly Lys Glu Phe Lys Cys Lys Val Asn Asn Lys Asp Leu Pro Ala Pro
        755                 760                 765

Ile Glu Arg Thr Ile Ser Lys Pro Lys Gly Ser Val Arg Ala Pro Gln
    770                 775                 780

Val Tyr Val Leu Pro Pro Pro Glu Glu Glu Met Thr Lys Lys Gln Val
785                 790                 795                 800

Thr Leu Thr Cys Met Val Thr Asp Phe Met Pro Glu Asp Ile Tyr Val
            805                 810                 815

Glu Trp Thr Asn Asn Gly Lys Thr Glu Leu Asn Tyr Lys Asn Thr Glu
            820                 825                 830

Pro Val Leu Asp Ser Asp Gly Ser Tyr Phe Met Tyr Ser Lys Leu Arg
        835                 840                 845

Val Glu Lys Lys Asn Trp Val Glu Arg Asn Ser Tyr Ser Cys Ser Val
    850                 855                 860

Val His Glu Gly Leu His Asn His His Thr Thr Lys Ser Phe Ser Arg
865                 870                 875                 880

Thr Pro Gly Lys


<210> SEQ ID NO 326
<211> LENGTH: 880
<212> TYPE: PRT
<213> ORGANISM: Artificial Sequence
<220> FEATURE:
<223> OTHER INFORMATION: mST2-mIL1RAcP-mFc

<400> SEQUENCE: 326

Ser Lys Ser Ser Trp Gly Leu Glu Asn Glu Ala Leu Ile Val Arg Cys
1               5                   10                  15

Pro Gln Arg Gly Arg Ser Thr Tyr Pro Val Glu Trp Tyr Tyr Ser Asp
            20                  25                  30

Thr Asn Glu Ser Ile Pro Thr Gln Lys Arg Asn Arg Ile Phe Val Ser
        35                  40                  45

Arg Asp Arg Leu Lys Phe Leu Pro Ala Arg Val Glu Asp Ser Gly Ile
    50                  55                  60

Tyr Ala Cys Val Ile Arg Ser Pro Asn Leu Asn Lys Thr Gly Tyr Leu
65                  70                  75                  80

Asn Val Thr Ile His Lys Lys Pro Pro Ser Cys Asn Ile Pro Asp Tyr
                85                  90                  95

Leu Met Tyr Ser Thr Val Arg Gly Ser Asp Lys Asn Phe Lys Ile Thr
            100                 105                 110

Cys Pro Thr Ile Asp Leu Tyr Asn Trp Thr Ala Pro Val Gln Trp Phe
        115                 120                 125

Lys Asn Cys Lys Ala Leu Gln Glu Pro Arg Phe Arg Ala His Arg Ser
    130                 135                 140

Tyr Leu Phe Ile Asp Asn Val Thr His Asp Asp Glu Gly Asp Tyr Thr
145                 150                 155                 160

Cys Gln Phe Thr His Ala Glu Asn Gly Thr Asn Tyr Ile Val Thr Ala
                165                 170                 175

Thr Arg Ser Phe Thr Val Glu Glu Lys Gly Phe Ser Met Phe Pro Val
            180                 185                 190

Ile Thr Asn Pro Pro Tyr Asn His Thr Met Glu Val Glu Ile Gly Lys
        195                 200                 205
```

-continued

```
Pro Ala Ser Ile Ala Cys Ser Ala Cys Phe Gly Lys Gly Ser His Phe
    210                 215                 220

Leu Ala Asp Val Leu Trp Gln Ile Asn Lys Thr Val Val Gly Asn Phe
225                 230                 235                 240

Gly Glu Ala Arg Ile Gln Glu Glu Glu Gly Arg Asn Glu Ser Ser Ser
                245                 250                 255

Asn Asp Met Asp Cys Leu Thr Ser Val Leu Arg Ile Thr Gly Val Thr
            260                 265                 270

Glu Lys Asp Leu Ser Leu Glu Tyr Asp Cys Leu Ala Leu Asn Leu His
        275                 280                 285

Gly Met Ile Arg His Thr Ile Arg Leu Arg Arg Lys Gln Pro Ile Asp
    290                 295                 300

His Arg Ser Glu Arg Cys Asp Asp Trp Gly Leu Asp Thr Met Arg Gln
305                 310                 315                 320

Ile Gln Val Phe Glu Asp Glu Pro Ala Arg Ile Lys Cys Pro Leu Phe
                325                 330                 335

Glu His Phe Leu Lys Tyr Asn Tyr Ser Thr Ala His Ser Ser Gly Leu
            340                 345                 350

Thr Leu Ile Trp Tyr Trp Thr Arg Gln Asp Arg Asp Leu Glu Glu Pro
        355                 360                 365

Ile Asn Phe Arg Leu Pro Glu Asn Arg Ile Ser Lys Glu Lys Asp Val
    370                 375                 380

Leu Trp Phe Arg Pro Thr Leu Leu Asn Asp Thr Gly Asn Tyr Thr Cys
385                 390                 395                 400

Met Leu Arg Asn Thr Thr Tyr Cys Ser Lys Val Ala Phe Pro Leu Glu
                405                 410                 415

Val Val Gln Lys Asp Ser Cys Phe Asn Ser Ala Met Arg Phe Pro Val
            420                 425                 430

His Lys Met Tyr Ile Glu His Gly Ile His Lys Ile Thr Cys Pro Asn
        435                 440                 445

Val Asp Gly Tyr Phe Pro Ser Ser Val Lys Pro Ser Val Thr Trp Tyr
    450                 455                 460

Lys Gly Cys Thr Glu Ile Val Asp Phe His Asn Val Leu Pro Glu Gly
465                 470                 475                 480

Met Asn Leu Ser Phe Phe Ile Pro Leu Val Ser Asn Asn Gly Asn Tyr
                485                 490                 495

Thr Cys Val Val Thr Tyr Pro Glu Asn Gly Arg Leu Phe His Leu Thr
            500                 505                 510

Arg Thr Val Thr Val Lys Val Val Gly Ser Pro Lys Asp Ala Leu Pro
        515                 520                 525

Pro Gln Ile Tyr Ser Pro Asn Asp Arg Val Val Tyr Glu Lys Glu Pro
    530                 535                 540

Gly Glu Glu Leu Val Ile Pro Cys Lys Val Tyr Phe Ser Phe Ile Met
545                 550                 555                 560

Asp Ser His Asn Glu Val Trp Trp Thr Ile Asp Gly Lys Lys Pro Asp
                565                 570                 575

Asp Val Thr Val Asp Ile Thr Ile Asn Glu Ser Val Ser Tyr Ser Ser
            580                 585                 590

Thr Glu Asp Glu Thr Arg Thr Gln Ile Leu Ser Ile Lys Lys Val Thr
        595                 600                 605

Pro Glu Asp Leu Arg Arg Asn Tyr Val Cys His Ala Arg Asn Thr Lys
    610                 615                 620
```

Gly Glu Ala Glu Gln Ala Ala Lys Val Lys Gln Lys Val Ile Pro Pro
625 630 635 640

Arg Tyr Thr Val Glu Ser Gly Glu Pro Arg Gly Pro Thr Ile Lys Pro
645 650 655

Cys Pro Pro Cys Lys Cys Pro Ala Pro Asn Leu Leu Gly Gly Pro Ser
660 665 670

Val Phe Ile Phe Pro Pro Lys Ile Lys Asp Val Leu Met Ile Ser Leu
675 680 685

Ser Pro Ile Val Thr Cys Val Val Val Asp Val Ser Glu Asp Asp Pro
690 695 700

Asp Val Gln Ile Ser Trp Phe Val Asn Asn Val Glu Val His Thr Ala
705 710 715 720

Gln Thr Gln Thr His Arg Glu Asp Tyr Asn Ser Thr Leu Arg Val Val
725 730 735

Ser Ala Leu Pro Ile Gln His Gln Asp Trp Met Ser Gly Lys Glu Phe
740 745 750

Lys Cys Lys Val Asn Asn Lys Asp Leu Pro Ala Pro Ile Glu Arg Thr
755 760 765

Ile Ser Lys Pro Lys Gly Ser Val Arg Ala Pro Gln Val Tyr Val Leu
770 775 780

Pro Pro Pro Glu Glu Glu Met Thr Lys Lys Gln Val Thr Leu Thr Cys
785 790 795 800

Met Val Thr Asp Phe Met Pro Glu Asp Ile Tyr Val Glu Trp Thr Asn
805 810 815

Asn Gly Lys Thr Glu Leu Asn Tyr Lys Asn Thr Glu Pro Val Leu Asp
820 825 830

Ser Asp Gly Ser Tyr Phe Met Tyr Ser Lys Leu Arg Val Glu Lys Lys
835 840 845

Asn Trp Val Glu Arg Asn Ser Tyr Ser Cys Ser Val Val His Glu Gly
850 855 860

Leu His Asn His His Thr Thr Lys Ser Phe Ser Arg Thr Pro Gly Lys
865 870 875 880

<210> SEQ ID NO 327
<211> LENGTH: 876
<212> TYPE: PRT
<213> ORGANISM: Artificial Sequence
<220> FEATURE:
<223> OTHER INFORMATION: hST2-hL1RAcP-hFc

<400> SEQUENCE: 327

Lys Phe Ser Lys Gln Ser Trp Gly Leu Glu Asn Glu Ala Leu Ile Val
1 5 10 15

Arg Cys Pro Arg Gln Gly Lys Pro Ser Tyr Thr Val Asp Trp Tyr Tyr
20 25 30

Ser Gln Thr Asn Lys Ser Ile Pro Thr Gln Glu Arg Asn Arg Val Phe
35 40 45

Ala Ser Gly Gln Leu Leu Lys Phe Leu Pro Ala Ala Val Ala Asp Ser
50 55 60

Gly Ile Tyr Thr Cys Ile Val Arg Ser Pro Thr Phe Asn Arg Thr Gly
65 70 75 80

Tyr Ala Asn Val Thr Ile Tyr Lys Lys Gln Ser Asp Cys Asn Val Pro
85 90 95

Asp Tyr Leu Met Tyr Ser Thr Val Ser Gly Ser Glu Lys Asn Ser Lys
100 105 110

-continued

```
Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
    210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
        275                 280                 285

Asn Leu His Gly Leu Arg Arg His Thr Val Arg Leu Ser Arg Lys Asn
    290                 295                 300

Pro Ile Asp His His Ser Ser Glu Arg Cys Asp Asp Trp Gly Leu Asp
305                 310                 315                 320

Thr Met Arg Gln Ile Gln Val Phe Glu Asp Glu Pro Ala Arg Ile Lys
                325                 330                 335

Cys Pro Leu Phe Glu His Phe Leu Lys Phe Asn Tyr Ser Thr Ala His
            340                 345                 350

Ser Ala Gly Leu Thr Leu Ile Trp Tyr Trp Thr Arg Gln Asp Arg Asp
        355                 360                 365

Leu Glu Glu Pro Ile Asn Phe Arg Leu Pro Glu Asn Arg Ile Ser Lys
    370                 375                 380

Glu Lys Asp Val Leu Trp Phe Arg Pro Thr Leu Leu Asn Asp Thr Gly
385                 390                 395                 400

Asn Tyr Thr Cys Met Leu Arg Asn Thr Thr Tyr Cys Ser Lys Val Ala
                405                 410                 415

Phe Pro Leu Glu Val Val Gln Lys Asp Ser Cys Phe Asn Ser Pro Met
            420                 425                 430

Lys Leu Pro Val His Lys Leu Tyr Ile Glu Tyr Gly Ile Gln Arg Ile
        435                 440                 445

Thr Cys Pro Asn Val Asp Gly Tyr Phe Pro Ser Ser Val Lys Pro Thr
    450                 455                 460

Ile Thr Trp Tyr Met Gly Cys Tyr Lys Ile Gln Asn Phe Asn Asn Val
465                 470                 475                 480

Ile Pro Glu Gly Met Asn Leu Ser Phe Leu Ile Ala Leu Ile Ser Asn
                485                 490                 495

Asn Gly Asn Tyr Thr Cys Val Val Thr Tyr Pro Glu Asn Gly Arg Thr
            500                 505                 510

Phe His Leu Thr Arg Thr Leu Thr Val Lys Val Val Gly Ser Pro Lys
        515                 520                 525

Asn Ala Val Pro Pro Val Ile His Ser Pro Asn Asp His Val Val Tyr
```

```
    530                 535                 540

Glu Lys Glu Pro Gly Glu Glu Leu Leu Ile Pro Cys Thr Val Tyr Phe
545                 550                 555                 560

Ser Phe Leu Met Asp Ser Arg Asn Glu Val Trp Trp Thr Ile Asp Gly
                565                 570                 575

Lys Lys Pro Asp Asp Ile Thr Ile Asp Val Thr Ile Asn Glu Ser Ile
            580                 585                 590

Ser His Ser Arg Thr Glu Asp Glu Thr Arg Thr Gln Ile Leu Ser Ile
        595                 600                 605

Lys Lys Val Thr Ser Glu Asp Leu Lys Arg Ser Tyr Val Cys His Ala
    610                 615                 620

Arg Ser Ala Lys Gly Glu Val Ala Lys Ala Ala Lys Val Lys Gln Lys
625                 630                 635                 640

Val Pro Ala Pro Arg Tyr Thr Val Glu Asp Lys Thr His Thr Cys Pro
                645                 650                 655

Pro Cys Pro Ala Pro Glu Leu Leu Gly Gly Pro Ser Val Phe Leu Phe
            660                 665                 670

Pro Pro Lys Pro Lys Asp Thr Leu Met Ile Ser Arg Thr Pro Glu Val
        675                 680                 685

Thr Cys Val Val Val Asp Val Ser His Glu Asp Pro Glu Val Lys Phe
    690                 695                 700

Asn Trp Tyr Val Asp Gly Val Glu Val His Asn Ala Lys Thr Lys Pro
705                 710                 715                 720

Arg Glu Glu Gln Tyr Asn Ser Thr Tyr Arg Val Val Ser Val Leu Thr
                725                 730                 735

Val Leu His Gln Asp Trp Leu Asn Gly Lys Glu Tyr Lys Cys Lys Val
            740                 745                 750

Ser Asn Lys Ala Leu Pro Ala Pro Ile Glu Lys Thr Ile Ser Lys Ala
        755                 760                 765

Lys Gly Gln Pro Arg Glu Pro Gln Val Tyr Thr Leu Pro Pro Ser Arg
    770                 775                 780

Asp Glu Leu Thr Lys Asn Gln Val Ser Leu Thr Cys Leu Val Lys Gly
785                 790                 795                 800

Phe Tyr Pro Ser Asp Ile Ala Val Glu Trp Glu Ser Asn Gly Gln Pro
                805                 810                 815

Glu Asn Asn Tyr Lys Thr Thr Pro Pro Val Leu Asp Ser Asp Gly Ser
            820                 825                 830

Phe Phe Leu Tyr Ser Lys Leu Thr Val Asp Lys Ser Arg Trp Gln Gln
        835                 840                 845

Gly Asn Val Phe Ser Cys Ser Val Met His Glu Ala Leu His Asn His
    850                 855                 860

Tyr Thr Gln Lys Ser Leu Ser Leu Ser Pro Gly Lys
865                 870                 875


<210> SEQ ID NO 328
<211> LENGTH: 310
<212> TYPE: PRT
<213> ORGANISM: Artificial Sequence
<220> FEATURE:
<223> OTHER INFORMATION: human ST2 extracellular domain

<400> SEQUENCE: 328

Lys Phe Ser Lys Gln Ser Trp Gly Leu Glu Asn Glu Ala Leu Ile Val
1               5                   10                  15

Arg Cys Pro Arg Gln Gly Lys Pro Ser Tyr Thr Val Asp Trp Tyr Tyr
```

```
            20                  25                  30

Ser Gln Thr Asn Lys Ser Ile Pro Thr Gln Glu Arg Asn Arg Val Phe
        35                  40                  45

Ala Ser Gly Gln Leu Leu Lys Phe Leu Pro Ala Ala Val Ala Asp Ser
    50                  55                  60

Gly Ile Tyr Thr Cys Ile Val Arg Ser Pro Thr Phe Asn Arg Thr Gly
65                  70                  75                  80

Tyr Ala Asn Val Thr Ile Tyr Lys Lys Gln Ser Asp Cys Asn Val Pro
                85                  90                  95

Asp Tyr Leu Met Tyr Ser Thr Val Ser Gly Ser Glu Lys Asn Ser Lys
            100                 105                 110

Ile Tyr Cys Pro Thr Ile Asp Leu Tyr Asn Trp Thr Ala Pro Leu Glu
        115                 120                 125

Trp Phe Lys Asn Cys Gln Ala Leu Gln Gly Ser Arg Tyr Arg Ala His
    130                 135                 140

Lys Ser Phe Leu Val Ile Asp Asn Val Met Thr Glu Asp Ala Gly Asp
145                 150                 155                 160

Tyr Thr Cys Lys Phe Ile His Asn Glu Asn Gly Ala Asn Tyr Ser Val
                165                 170                 175

Thr Ala Thr Arg Ser Phe Thr Val Lys Asp Glu Gln Gly Phe Ser Leu
            180                 185                 190

Phe Pro Val Ile Gly Ala Pro Ala Gln Asn Glu Ile Lys Glu Val Glu
        195                 200                 205

Ile Gly Lys Asn Ala Asn Leu Thr Cys Ser Ala Cys Phe Gly Lys Gly
    210                 215                 220

Thr Gln Phe Leu Ala Ala Val Leu Trp Gln Leu Asn Gly Thr Lys Ile
225                 230                 235                 240

Thr Asp Phe Gly Glu Pro Arg Ile Gln Gln Glu Glu Gly Gln Asn Gln
                245                 250                 255

Ser Phe Ser Asn Gly Leu Ala Cys Leu Asp Met Val Leu Arg Ile Ala
            260                 265                 270

Asp Val Lys Glu Glu Asp Leu Leu Leu Gln Tyr Asp Cys Leu Ala Leu
        275                 280                 285

Asn Leu His Gly Leu Arg Arg His Thr Val Arg Leu Ser Arg Lys Asn
    290                 295                 300

Pro Ile Asp His His Ser
305                 310


<210> SEQ ID NO 329
<211> LENGTH: 306
<212> TYPE: PRT
<213> ORGANISM: Artificial Sequence
<220> FEATURE:
<223> OTHER INFORMATION: mouse ST2 extracellular domain

<400> SEQUENCE: 329

Ser Lys Ser Ser Trp Gly Leu Glu Asn Glu Ala Leu Ile Val Arg Cys
1               5                   10                  15

Pro Gln Arg Gly Arg Ser Thr Tyr Pro Val Glu Trp Tyr Tyr Ser Asp
            20                  25                  30

Thr Asn Glu Ser Ile Pro Thr Gln Lys Arg Asn Arg Ile Phe Val Ser
        35                  40                  45

Arg Asp Arg Leu Lys Phe Leu Pro Ala Arg Val Glu Asp Ser Gly Ile
    50                  55                  60

Tyr Ala Cys Val Ile Arg Ser Pro Asn Leu Asn Lys Thr Gly Tyr Leu
```

```
65                  70                  75                  80

Asn Val Thr Ile His Lys Lys Pro Pro Ser Cys Asn Ile Pro Asp Tyr
                85                  90                  95

Leu Met Tyr Ser Thr Val Arg Gly Ser Asp Lys Asn Phe Lys Ile Thr
            100                 105                 110

Cys Pro Thr Ile Asp Leu Tyr Asn Trp Thr Ala Pro Val Gln Trp Phe
        115                 120                 125

Lys Asn Cys Lys Ala Leu Gln Glu Pro Arg Phe Arg Ala His Arg Ser
    130                 135                 140

Tyr Leu Phe Ile Asp Asn Val Thr His Asp Asp Glu Gly Asp Tyr Thr
145                 150                 155                 160

Cys Gln Phe Thr His Ala Glu Asn Gly Thr Asn Tyr Ile Val Thr Ala
                165                 170                 175

Thr Arg Ser Phe Thr Val Glu Glu Lys Gly Phe Ser Met Phe Pro Val
            180                 185                 190

Ile Thr Asn Pro Pro Tyr Asn His Thr Met Glu Val Glu Ile Gly Lys
        195                 200                 205

Pro Ala Ser Ile Ala Cys Ser Ala Cys Phe Gly Lys Gly Ser His Phe
    210                 215                 220

Leu Ala Asp Val Leu Trp Gln Ile Asn Lys Thr Val Val Gly Asn Phe
225                 230                 235                 240

Gly Glu Ala Arg Ile Gln Glu Glu Glu Gly Arg Asn Glu Ser Ser Ser
                245                 250                 255

Asn Asp Met Asp Cys Leu Thr Ser Val Leu Arg Ile Thr Gly Val Thr
            260                 265                 270

Glu Lys Asp Leu Ser Leu Glu Tyr Asp Cys Leu Ala Leu Asn Leu His
        275                 280                 285

Gly Met Ile Arg His Thr Ile Arg Leu Arg Arg Lys Gln Pro Ile Asp
    290                 295                 300

His Arg
305


<210> SEQ ID NO 330
<211> LENGTH: 339
<212> TYPE: PRT
<213> ORGANISM: Artificial Sequence
<220> FEATURE:
<223> OTHER INFORMATION: human IL1RAcP extracellular domain

<400> SEQUENCE: 330

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Phe Asn Tyr Ser Thr Ala His Ser Ala Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Pro Met Lys Leu Pro Val His Lys
```

```
        115                 120                 125

Leu Tyr Ile Glu Tyr Gly Ile Gln Arg Ile Thr Cys Pro Asn Val Asp
    130                 135                 140

Gly Tyr Phe Pro Ser Ser Val Lys Pro Thr Ile Thr Trp Tyr Met Gly
145                 150                 155                 160

Cys Tyr Lys Ile Gln Asn Phe Asn Asn Val Ile Pro Glu Gly Met Asn
                165                 170                 175

Leu Ser Phe Leu Ile Ala Leu Ile Ser Asn Asn Gly Asn Tyr Thr Cys
            180                 185                 190

Val Val Thr Tyr Pro Glu Asn Gly Arg Thr Phe His Leu Thr Arg Thr
        195                 200                 205

Leu Thr Val Lys Val Val Gly Ser Pro Lys Asn Ala Val Pro Pro Val
    210                 215                 220

Ile His Ser Pro Asn Asp His Val Val Tyr Glu Lys Glu Pro Gly Glu
225                 230                 235                 240

Glu Leu Leu Ile Pro Cys Thr Val Tyr Phe Ser Phe Leu Met Asp Ser
                245                 250                 255

Arg Asn Glu Val Trp Trp Thr Ile Asp Gly Lys Lys Pro Asp Asp Ile
            260                 265                 270

Thr Ile Asp Val Thr Ile Asn Glu Ser Ile Ser His Ser Arg Thr Glu
        275                 280                 285

Asp Glu Thr Arg Thr Gln Ile Leu Ser Ile Lys Lys Val Thr Ser Glu
    290                 295                 300

Asp Leu Lys Arg Ser Tyr Val Cys His Ala Arg Ser Ala Lys Gly Glu
305                 310                 315                 320

Val Ala Lys Ala Ala Lys Val Lys Gln Lys Val Pro Ala Pro Arg Tyr
                325                 330                 335

Thr Val Glu


<210> SEQ ID NO 331
<211> LENGTH: 339
<212> TYPE: PRT
<213> ORGANISM: Artificial Sequence
<220> FEATURE:
<223> OTHER INFORMATION: mouse IL1RAcP extracellular domain

<400> SEQUENCE: 331

Ser Glu Arg Cys Asp Asp Trp Gly Leu Asp Thr Met Arg Gln Ile Gln
1               5                   10                  15

Val Phe Glu Asp Glu Pro Ala Arg Ile Lys Cys Pro Leu Phe Glu His
            20                  25                  30

Phe Leu Lys Tyr Asn Tyr Ser Thr Ala His Ser Ser Gly Leu Thr Leu
        35                  40                  45

Ile Trp Tyr Trp Thr Arg Gln Asp Arg Asp Leu Glu Glu Pro Ile Asn
    50                  55                  60

Phe Arg Leu Pro Glu Asn Arg Ile Ser Lys Glu Lys Asp Val Leu Trp
65                  70                  75                  80

Phe Arg Pro Thr Leu Leu Asn Asp Thr Gly Asn Tyr Thr Cys Met Leu
                85                  90                  95

Arg Asn Thr Thr Tyr Cys Ser Lys Val Ala Phe Pro Leu Glu Val Val
            100                 105                 110

Gln Lys Asp Ser Cys Phe Asn Ser Ala Met Arg Phe Pro Val His Lys
        115                 120                 125

Met Tyr Ile Glu His Gly Ile His Lys Ile Thr Cys Pro Asn Val Asp
    130                 135                 140
```

Gly Tyr Phe Pro Ser Ser Val Lys Pro Ser Val Thr Trp Tyr Lys Gly
145 150 155 160

Cys Thr Glu Ile Val Asp Phe His Asn Val Leu Pro Glu Gly Met Asn
165 170 175

Leu Ser Phe Phe Ile Pro Leu Val Ser Asn Asn Gly Asn Tyr Thr Cys
180 185 190

Val Val Thr Tyr Pro Glu Asn Gly Arg Leu Phe His Leu Thr Arg Thr
195 200 205

Val Thr Val Lys Val Val Gly Ser Pro Lys Asp Ala Leu Pro Pro Gln
210 215 220

Ile Tyr Ser Pro Asn Asp Arg Val Val Tyr Glu Lys Glu Pro Gly Glu
225 230 235 240

Glu Leu Val Ile Pro Cys Lys Val Tyr Phe Ser Phe Ile Met Asp Ser
245 250 255

His Asn Glu Val Trp Trp Thr Ile Asp Gly Lys Lys Pro Asp Asp Val
260 265 270

Thr Val Asp Ile Thr Ile Asn Glu Ser Val Ser Tyr Ser Ser Thr Glu
275 280 285

Asp Glu Thr Arg Thr Gln Ile Leu Ser Ile Lys Lys Val Thr Pro Glu
290 295 300

Asp Leu Arg Arg Asn Tyr Val Cys His Ala Arg Asn Thr Lys Gly Glu
305 310 315 320

Ala Glu Gln Ala Ala Lys Val Lys Gln Lys Val Ile Pro Pro Arg Tyr
325 330 335

Thr Val Glu

<210> SEQ ID NO 332
<211> LENGTH: 227
<212> TYPE: PRT
<213> ORGANISM: Artificial Sequence
<220> FEATURE:
<223> OTHER INFORMATION: human IgG1 Fc

<400> SEQUENCE: 332

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Ser Arg Asp Glu Leu Thr Lys Asn Gln Val Ser
130 135 140

Leu Thr Cys Leu Val Lys Gly Phe Tyr Pro Ser Asp Ile Ala Val Glu
145 150 155 160

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 333
<211> LENGTH: 233
<212> TYPE: PRT
<213> ORGANISM: Artificial Sequence
<220> FEATURE:
<223> OTHER INFORMATION: mouse IgG2a Fc

<400> SEQUENCE: 333

Glu Pro Arg Gly Pro Thr Ile Lys Pro Cys Pro Pro Cys Lys Cys Pro
1               5                   10                  15

Ala Pro Asn Leu Leu Gly Gly Pro Ser Val Phe Ile Phe Pro Pro Lys
            20                  25                  30

Ile Lys Asp Val Leu Met Ile Ser Leu Ser Pro Ile Val Thr Cys Val
        35                  40                  45

Val Val Asp Val Ser Glu Asp Asp Pro Asp Val Gln Ile Ser Trp Phe
    50                  55                  60

Val Asn Asn Val Glu Val His Thr Ala Gln Thr Gln Thr His Arg Glu
65                  70                  75                  80

Asp Tyr Asn Ser Thr Leu Arg Val Val Ser Ala Leu Pro Ile Gln His
                85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230


<210> SEQ ID NO 334
<211> LENGTH: 167
<212> TYPE: PRT
<213> ORGANISM: Artificial Sequence
<220> FEATURE:
<223> OTHER INFORMATION: M.fascicularis IL-33-6His

<400> SEQUENCE: 334
```

```
Ser Ile Thr Gly Ile Ser Pro Ile Thr Glu Ser Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Lys Lys Lys Asp Lys Val
        35                  40                  45

Leu Leu Ser Tyr Tyr Glu Ser Gln His Pro Ser Ser Glu Ser Gly Asp
    50                  55                  60

Gly Val Asp Gly Lys Met Leu Met Val Thr Leu Ser Pro Thr Lys Asp
65                  70                  75                  80

Phe Trp Leu Gln Ala Asn Asn Lys Glu His Ser Val Glu Leu His Lys
                85                  90                  95

Cys Glu Lys Pro Leu Pro Asp Gln Ala Phe Phe Val Leu His Asn Arg
            100                 105                 110

Ser Phe Asn Cys Val Ser Phe Glu Cys Lys Thr Asp Pro Gly Val Phe
        115                 120                 125

Ile Gly Val Lys Asp Asn His Leu Ala Leu Ile Lys Val Asp Tyr Ser
    130                 135                 140

Glu Asn Leu Gly Ser Glu Asn Ile Leu Phe Lys Leu Ser Glu Ile Leu
145                 150                 155                 160

Glu His His His His His His
                165


<210> SEQ ID NO 335
<211> LENGTH: 117
<212> TYPE: PRT
<213> ORGANISM: Artificial Sequence
<220> FEATURE:
<223> OTHER INFORMATION: HCVR-mouse surrogate IL-4R Ab

<400> SEQUENCE: 335

Glu Val Gln Leu Gln Gln Ser Gly Pro Glu Leu Val Lys Pro Gly Ala
1               5                   10                  15

Ser Val Arg Met Ser Cys Lys Ala Ser Gly Tyr Thr Phe Thr Asp Tyr
            20                  25                  30

Asn Ile His Trp Val Lys Gln Ser His Gly Lys Ser Leu Glu Trp Ile
        35                  40                  45

Gly Tyr Ile Tyr Pro Asn Asn Gly Asp Asn Gly Tyr Asn Gln Lys Phe
    50                  55                  60

Arg Gly Lys Ala Thr Leu Thr Val Asp Lys Ser Ser Ser Thr Ala Tyr
65                  70                  75                  80

Met Glu Leu Arg Ser Leu Thr Ser Asp Asp Ser Ala Val Tyr Tyr Cys
                85                  90                  95

Ala Arg Gly Arg Leu Arg Tyr Phe Asp Val Trp Gly Thr Gly Thr Thr
            100                 105                 110

Val Thr Val Ser Ser
        115


<210> SEQ ID NO 336
<211> LENGTH: 111
<212> TYPE: PRT
<213> ORGANISM: Artificial Sequence
<220> FEATURE:
<223> OTHER INFORMATION: LCVR-mouse surrogate IL-4R Ab

<400> SEQUENCE: 336

Asn Ile Val Leu Thr Gln Ser Pro Ala Ser Leu Ala Val Ser Leu Gly
```

```
1               5                   10                  15

Gln Arg Ala Thr Ile Ser Cys Arg Ala Ser Glu Ser Val Asp Asn Tyr
            20                  25                  30

Gly His Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Leu Asp
65                  70                  75                  80

Pro Val Glu Ala Asp Asp Ala Ala Thr Tyr Tyr Cys Gln Gln Tyr Asn
                85                  90                  95

Glu Asp Pro Pro Thr Phe Gly Ser Gly Thr Lys Leu Glu Ile Lys
            100                 105                 110


<210> SEQ ID NO 337
<211> LENGTH: 124
<212> TYPE: PRT
<213> ORGANISM: Artificial Sequence
<220> FEATURE:
<223> OTHER INFORMATION: Dupilumab HCVR

<400> SEQUENCE: 337

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120


<210> SEQ ID NO 338
<211> LENGTH: 112
<212> TYPE: PRT
<213> ORGANISM: Artificial Sequence
<220> FEATURE:
<223> OTHER INFORMATION: Dupilumab LCVR

<400> SEQUENCE: 338

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110


<210> SEQ ID NO 339
<211> LENGTH: 8
<212> TYPE: PRT
<213> ORGANISM: Artificial Sequence
<220> FEATURE:
<223> OTHER INFORMATION: Dupilumab HCDR1

<400> SEQUENCE: 339

Gly Phe Thr Phe Arg Asp Tyr Ala
1               5


<210> SEQ ID NO 340
<211> LENGTH: 8
<212> TYPE: PRT
<213> ORGANISM: Artificial Sequence
<220> FEATURE:
<223> OTHER INFORMATION: Dupilumab HCDR2

<400> SEQUENCE: 340

Ile Ser Gly Ser Gly Gly Asn Thr
1               5


<210> SEQ ID NO 341
<211> LENGTH: 18
<212> TYPE: PRT
<213> ORGANISM: Artificial Sequence
<220> FEATURE:
<223> OTHER INFORMATION: Dupilumab HCDR3

<400> SEQUENCE: 341

Ala Lys Asp Arg Leu Ser Ile Thr Ile Arg Pro Arg Tyr Tyr Gly Leu
1               5                   10                  15

Asp Val


<210> SEQ ID NO 342
<211> LENGTH: 11
<212> TYPE: PRT
<213> ORGANISM: Artificial Sequence
<220> FEATURE:
<223> OTHER INFORMATION: Dupilumab LCDR1

<400> SEQUENCE: 342

Gln Ser Leu Leu Tyr Ser Ile Gly Tyr Asn Tyr
1               5                   10


<210> SEQ ID NO 343
<211> LENGTH: 3
<212> TYPE: PRT
<213> ORGANISM: Artificial Sequence
<220> FEATURE:
<223> OTHER INFORMATION: Dupilumab LCDR2

<400> SEQUENCE: 343

Leu Gly Ser
1


<210> SEQ ID NO 344
<211> LENGTH: 9
<212> TYPE: PRT
<213> ORGANISM: Artificial Sequence
<220> FEATURE:
```

-continued

<223> OTHER INFORMATION: Dupilumab LCDR3

<400> SEQUENCE: 344

Met Gln Ala Leu Gln Thr Pro Tyr Thr
1 5

<210> SEQ ID NO 345
<211> LENGTH: 451
<212> TYPE: PRT
<213> ORGANISM: Artificial Sequence
<220> FEATURE:
<223> OTHER INFORMATION: Dupilumab heavy chain

<400> SEQUENCE: 345

Glu Val Gln Leu Val Glu Ser Gly Gly Gly Leu Glu Gln Pro Gly Gly
1 5 10 15

Ser Leu Arg Leu Ser Cys Ala Gly Ser Gly Phe Thr Phe Arg Asp Tyr
20 25 30

Ala Met Thr Trp Val Arg Gln Ala Pro Gly Lys Gly Leu Glu Trp Val
35 40 45

Ser Ser Ile Ser Gly Ser Gly Gly Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Arg Leu Ser Ile Thr Ile Arg Pro Arg Tyr Tyr Gly Leu
100 105 110

Asp Val Trp Gly Gln Gly Thr Thr Val Thr Val Ser Ser Ala Ser Thr
115 120 125

Lys Gly Pro Ser Val Phe Pro Leu Ala Pro Cys Ser Arg Ser Thr Ser
130 135 140

Glu Ser Thr Ala Ala Leu Gly Cys Leu Val Lys Asp Tyr Phe Pro Glu
145 150 155 160

Pro Val Thr Val Ser Trp Asn Ser Gly Ala Leu Thr Ser Gly Val His
165 170 175

Thr Phe Pro Ala Val Leu Gln Ser Ser Gly Leu Tyr Ser Leu Ser Ser
180 185 190

Val Val Thr Val Pro Ser Ser Ser Leu Gly Thr Lys Thr Tyr Thr Cys
195 200 205

Asn Val Asp His Lys Pro Ser Asn Thr Lys Val Asp Lys Arg Val Glu
210 215 220

Ser Lys Tyr Gly Pro Pro Cys Pro Pro Cys Pro Ala Pro Glu Phe Leu
225 230 235 240

Gly Gly Pro Ser Val Phe Leu Phe Pro Pro Lys Pro Lys Asp Thr Leu
245 250 255

Met Ile Ser Arg Thr Pro Glu Val Thr Cys Val Val Val Asp Val Ser
260 265 270

Gln Glu Asp Pro Glu Val Gln Phe Asn Trp Tyr Val Asp Gly Val Glu
275 280 285

Val His Asn Ala Lys Thr Lys Pro Arg Glu Glu Gln Phe Asn Ser Thr
290 295 300

Tyr Arg Val Val Ser Val Leu Thr Val Leu His Gln Asp Trp Leu Asn
305 310 315 320

Gly Lys Glu Tyr Lys Cys Lys Val Ser Asn Lys Gly Leu Pro Ser Ser
325 330 335

```
Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450


<210> SEQ ID NO 346
<211> LENGTH: 219
<212> TYPE: PRT
<213> ORGANISM: Artificial Sequence
<220> FEATURE:
<223> OTHER INFORMATION: Dupilumab light chain

<400> SEQUENCE: 346

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 347
```

<211> LENGTH: 207
<212> TYPE: PRT
<213> ORGANISM: Artificial Sequence
<220> FEATURE:
<223> OTHER INFORMATION: human IL-4Ralpha

<400> SEQUENCE: 347

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
    50                  55                  60

Met Asp Asp Val Val Ser Ala Asp Asn Tyr Thr Leu Asp Leu Trp Ala
65                  70                  75                  80

Gly Gln Gln Leu Leu Trp Lys Gly Ser Phe Lys Pro Ser Glu His Val
                85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205

<210> SEQ ID NO 348
<211> LENGTH: 270
<212> TYPE: PRT
<213> ORGANISM: Artificial Sequence
<220> FEATURE:
<223> OTHER INFORMATION: hIL33_O95760 (prior to proteolytic processing)

<400> SEQUENCE: 348

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Glu Val Cys Pro Met Tyr Phe Met Lys Leu Arg
        35                  40                  45

Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr

```
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270


<210> SEQ ID NO 349
<211> LENGTH: 159
<212> TYPE: PRT
<213> ORGANISM: Artificial Sequence
<220> FEATURE:
<223> OTHER INFORMATION: hIL33_mature_PEPTIDE (after proteolytic
      processing)

<400> SEQUENCE: 349

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
            100                 105                 110

His Ser Asn Cys Val Ser Phe Glu Cys Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr
145                 150                 155


<210> SEQ ID NO 350
<211> LENGTH: 12
<212> TYPE: PRT
<213> ORGANISM: Artificial Sequence
<220> FEATURE:
<223> OTHER INFORMATION: Amino Acid residues 1-12 of SEQ ID NO: 349;
      also corresponds to residues 112-123 of SEQ ID NO: 348
      (Uniprot O95760)
```

<400> SEQUENCE: 350

Ser Ile Thr Gly Ile Ser Pro Ile Thr Glu Tyr Leu
1               5                   10

<210> SEQ ID NO 351
<211> LENGTH: 87
<212> TYPE: PRT
<213> ORGANISM: Artificial Sequence
<220> FEATURE:
<223> OTHER INFORMATION: Amino Acid residues 50-94 of SEQ ID NO: 349; also corresponds to residues 161-205 of SEQ ID NO: 348 (Uniprot O95760)

<400> SEQUENCE: 351

Ile Thr Glu Tyr Leu Ala Ser Leu Ser Thr Tyr Asn Asp Gln Ser Ile
1               5                   10                  15

Thr Phe Ala Leu Glu Asp Glu Ser Tyr Glu Ile Tyr Val Glu Asp Leu
            20                  25                  30

Lys Lys Asp Glu Lys Lys Asp Lys Val Leu Leu Ser Tyr Tyr Glu Ser
        35                  40                  45

Gln His Pro Ser Asn Glu Ser Gly Asp Gly Val Asp Gly Lys Met Leu
    50                  55                  60

Met Val Thr Leu Ser Pro Thr Lys Asp Phe Trp Leu His Ala Asn Asn
65                  70                  75                  80

Lys Glu His Ser Val Glu Leu
                85

<210> SEQ ID NO 352
<211> LENGTH: 556
<212> TYPE: PRT
<213> ORGANISM: Artificial Sequence
<220> FEATURE:
<223> OTHER INFORMATION: Human ST2 (See GenBank accession number NP_057316)

<400> SEQUENCE: 352

Met Gly Phe Trp Ile Leu Ala Ile Leu Thr Ile Leu Met Tyr Ser Thr
1               5                   10                  15

Ala Ala Lys Phe Ser Lys Gln Ser Trp Gly Leu Glu Asn Glu Ala Leu
            20                  25                  30

Ile Val Arg Cys Pro Arg Gln Gly Lys Pro Ser Tyr Thr Val Asp Trp
        35                  40                  45

Tyr Tyr Ser Gln Thr Asn Lys Ser Ile Pro Thr Gln Glu Arg Asn Arg
    50                  55                  60

Val Phe Ala Ser Gly Gln Leu Leu Lys Phe Leu Pro Ala Ala Val Ala
65                  70                  75                  80

Asp Ser Gly Ile Tyr Thr Cys Ile Val Arg Ser Pro Thr Phe Asn Arg
                85                  90                  95

Thr Gly Tyr Ala Asn Val Thr Ile Tyr Lys Lys Gln Ser Asp Cys Asn
            100                 105                 110

Val Pro Asp Tyr Leu Met Tyr Ser Thr Val Ser Gly Ser Glu Lys Asn
        115                 120                 125

Ser Lys Ile Tyr Cys Pro Thr Ile Asp Leu Tyr Asn Trp Thr Ala Pro
    130                 135                 140

Leu Glu Trp Phe Lys Asn Cys Gln Ala Leu Gln Gly Ser Arg Tyr Arg
145                 150                 155                 160

Ala His Lys Ser Phe Leu Val Ile Asp Asn Val Met Thr Glu Asp Ala
                165                 170                 175

Gly Asp Tyr Thr Cys Lys Phe Ile His Asn Glu Asn Gly Ala Asn Tyr
180 185 190

Ser Val Thr Ala Thr Arg Ser Phe Thr Val Lys Asp Glu Gln Gly Phe
195 200 205

Ser Leu Phe Pro Val Ile Gly Ala Pro Ala Gln Asn Glu Ile Lys Glu
210 215 220

Val Glu Ile Gly Lys Asn Ala Asn Leu Thr Cys Ser Ala Cys Phe Gly
225 230 235 240

Lys Gly Thr Gln Phe Leu Ala Ala Val Leu Trp Gln Leu Asn Gly Thr
245 250 255

Lys Ile Thr Asp Phe Gly Glu Pro Arg Ile Gln Gln Glu Glu Gly Gln
260 265 270

Asn Gln Ser Phe Ser Asn Gly Leu Ala Cys Leu Asp Met Val Leu Arg
275 280 285

Ile Ala Asp Val Lys Glu Glu Asp Leu Leu Leu Gln Tyr Asp Cys Leu
290 295 300

Ala Leu Asn Leu His Gly Leu Arg Arg His Thr Val Arg Leu Ser Arg
305 310 315 320

Lys Asn Pro Ile Asp His His Ser Ile Tyr Cys Ile Ile Ala Val Cys
325 330 335

Ser Val Phe Leu Met Leu Ile Asn Val Leu Val Ile Ile Leu Lys Met
340 345 350

Phe Trp Ile Glu Ala Thr Leu Leu Trp Arg Asp Ile Ala Lys Pro Tyr
355 360 365

Lys Thr Arg Asn Asp Gly Lys Leu Tyr Asp Ala Tyr Val Val Tyr Pro
370 375 380

Arg Asn Tyr Lys Ser Ser Thr Asp Gly Ala Ser Arg Val Glu His Phe
385 390 395 400

Val His Gln Ile Leu Pro Asp Val Leu Glu Asn Lys Cys Gly Tyr Thr
405 410 415

Leu Cys Ile Tyr Gly Arg Asp Met Leu Pro Gly Glu Asp Val Val Thr
420 425 430

Ala Val Glu Thr Asn Ile Arg Lys Ser Arg Arg His Ile Phe Ile Leu
435 440 445

Thr Pro Gln Ile Thr His Asn Lys Glu Phe Ala Tyr Glu Gln Glu Val
450 455 460

Ala Leu His Cys Ala Leu Ile Gln Asn Asp Ala Lys Val Ile Leu Ile
465 470 475 480

Glu Met Glu Ala Leu Ser Glu Leu Asp Met Leu Gln Ala Glu Ala Leu
485 490 495

Gln Asp Ser Leu Gln His Leu Met Lys Val Gln Gly Thr Ile Lys Trp
500 505 510

Arg Glu Asp His Ile Ala Asn Lys Arg Ser Leu Asn Ser Lys Phe Trp
515 520 525

Lys His Val Arg Tyr Gln Met Pro Val Pro Ser Lys Ile Pro Arg Lys
530 535 540

Ala Ser Ser Leu Thr Pro Leu Ala Ala Gln Lys Gln
545 550 555

<210> SEQ ID NO 353
<211> LENGTH: 570
<212> TYPE: PRT
<213> ORGANISM: Artificial Sequence
<220> FEATURE:

<223> OTHER INFORMATION: Human IL-1RAcP (See GenBank accession number Q9NPH3)

<400> SEQUENCE: 353

```
Met Thr Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Leu Ala Cys Gly Phe Gly Ala Thr Val
        355                 360                 365

Leu Leu Val Val Ile Leu Ile Val Val Tyr His Val Tyr Trp Leu Glu
    370                 375                 380

Met Val Leu Phe Tyr Arg Ala His Phe Gly Thr Asp Glu Thr Ile Leu
385                 390                 395                 400
```

Asp Gly Lys Glu Tyr Asp Ile Tyr Val Ser Tyr Ala Arg Asn Ala Glu
405 410 415

Glu Glu Glu Phe Val Leu Leu Thr Leu Arg Gly Val Leu Glu Asn Glu
420 425 430

Phe Gly Tyr Lys Leu Cys Ile Phe Asp Arg Asp Ser Leu Pro Gly Gly
435 440 445

Ile Val Thr Asp Glu Thr Leu Ser Phe Ile Gln Lys Ser Arg Arg Leu
450 455 460

Leu Val Val Leu Ser Pro Asn Tyr Val Leu Gln Gly Thr Gln Ala Leu
465 470 475 480

Leu Glu Leu Lys Ala Gly Leu Glu Asn Met Ala Ser Arg Gly Asn Ile
485 490 495

Asn Val Ile Leu Val Gln Tyr Lys Ala Val Lys Glu Thr Lys Val Lys
500 505 510

Glu Leu Lys Arg Ala Lys Thr Val Leu Thr Val Ile Lys Trp Lys Gly
515 520 525

Glu Lys Ser Lys Tyr Pro Gln Gly Arg Phe Trp Lys Gln Leu Gln Val
530 535 540

Ala Met Pro Val Lys Lys Ser Pro Arg Arg Ser Ser Ser Asp Glu Gln
545 550 555 560

Gly Leu Ser Tyr Ser Ser Leu Lys Asn Val
565 570

<210> SEQ ID NO 354
<211> LENGTH: 449
<212> TYPE: PRT
<213> ORGANISM: Artificial Sequence
<220> FEATURE:
<223> OTHER INFORMATION: HC OF H4H9675P

<400> SEQUENCE: 354

Glu Val Gln Leu Val Glu Ser Gly Gly Asn Leu Glu Gln Pro Gly Gly
1 5 10 15

Ser Leu Arg Leu Ser Cys Thr Ala Ser Gly Phe Thr Phe Ser Arg Ser
20 25 30

Ala Met Asn Trp Val Arg Arg Ala Pro Gly Lys Gly Leu Glu Trp Val
35 40 45

Ser Gly Ile Ser Gly Ser Gly Gly Arg Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Ser Ala Glu Asp Thr Ala Ala Tyr Tyr Cys
85 90 95

Ala Lys Asp Ser Tyr Thr Thr Ser Trp Tyr Gly Gly Met Asp Val Trp
100 105 110

Gly His Gly Thr Thr Val Thr Val Ser Ser Ala Ser Thr Lys Gly Pro
115 120 125

Ser Val Phe Pro Leu Ala Pro Cys Ser Arg Ser Thr Ser Glu Ser Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

-continued

Val Pro Ser Ser Ser Leu Gly Thr Lys Thr Tyr Thr Cys Asn Val Asp
195 200 205

His Lys Pro Ser Asn Thr Lys Val Asp Lys Arg Val Glu Ser Lys Tyr
210 215 220

Gly Pro Pro Cys Pro Pro Cys Pro Ala Pro Glu Phe Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser Gln Glu Asp
260 265 270

Pro Glu Val Gln Phe Asn Trp Tyr Val Asp Gly Val Glu Val His Asn
275 280 285

Ala Lys Thr Lys Pro Arg Glu Glu Gln Phe Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Gly Leu Pro Ser Ser Ile Glu Lys
325 330 335

Thr Ile Ser Lys Ala Lys Gly Gln Pro Arg Glu Pro Gln Val Tyr Thr
340 345 350

Leu Pro Pro Ser Gln Glu Glu Met Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Arg Leu Thr Val Asp Lys
405 410 415

Ser Arg Trp Gln Glu Gly Asn Val Phe Ser Cys Ser Val Met His Glu
420 425 430

Ala Leu His Asn His Tyr Thr Gln Lys Ser Leu Ser Leu Ser Leu Gly
435 440 445

Lys

<210> SEQ ID NO 355
<211> LENGTH: 214
<212> TYPE: PRT
<213> ORGANISM: Artificial Sequence
<220> FEATURE:
<223> OTHER INFORMATION: LC OF H4H9675P

<400> SEQUENCE: 355

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Phe Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Ile Tyr Tyr Cys Gln Gln Ala Asn Ser Val Pro Ile
85 90 95

```
Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 356
<211> LENGTH: 166
<212> TYPE: PRT
<213> ORGANISM: Artificial Sequence
<220> FEATURE:
<223> OTHER INFORMATION: HUMAN IL-33 WITH HEXA-HIS TAG (AMINO ACIDS
      112-270 OF GENBANK ACCESSION NO. O95760)

<400> SEQUENCE: 356

Met Ser Ile Thr Gly Ile Ser Pro Ile Thr Glu Tyr Leu Ala Ser Leu
1               5                   10                  15

Ser Thr Tyr Asn Asp Gln Ser Ile Thr Phe Ala Leu Glu Asp Glu Ser
            20                  25                  30

Tyr Glu Ile Tyr Val Glu Asp Leu Lys Lys Asp Glu Lys Lys Asp Lys
        35                  40                  45

Val Leu Leu Ser Tyr Tyr Glu Ser Gln His Pro Ser Asn Glu Ser Gly
    50                  55                  60

Asp Gly Val Asp Gly Lys Met Leu Met Val Thr Leu Ser Pro Thr Lys
65                  70                  75                  80

Asp Phe Trp Leu His Ala Asn Asn Lys Glu His Ser Val Glu Leu His
                85                  90                  95

Lys Cys Glu Lys Pro Leu Pro Asp Gln Ala Phe Phe Val Leu His Asn
            100                 105                 110

Met His Ser Asn Cys Val Ser Phe Glu Cys Lys Thr Asp Pro Gly Val
        115                 120                 125

Phe Ile Gly Val Lys Asp Asn His Leu Ala Leu Ile Lys Val Asp Ser
    130                 135                 140

Ser Glu Asn Leu Cys Thr Glu Asn Ile Leu Phe Lys Leu Ser Glu Thr
145                 150                 155                 160

His His His His His His
                165


<210> SEQ ID NO 357
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: n is g or a
<222> LOCATION: (26) .. (26)
```

-continued

```
<400> SEQUENCE: 357

tataccatca caaagcctct cattanactt tgaatccaat gagtattact a            51


<210> SEQ ID NO 358
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: n is g or t
<222> LOCATION: (26) .. (26)

<400> SEQUENCE: 358

ccaatctttt ctcatgaaga caccancatg acctcttatt cttatttata t            51
```